US011305011B2

(12) United States Patent
Micklethwaite et al.

(10) Patent No.: US 11,305,011 B2
(45) Date of Patent: Apr. 19, 2022

(54) KAPPA MYELOMA ANTIGEN CHIMERIC ANTIGEN RECEPTORS AND USES THEREOF

(71) Applicant: HaemaLogix Pty. LTD., Eveleigh (AU)

(72) Inventors: Kenneth Micklethwaite, Westmead (AU); Rosanne Dunn, Eveleigh (AU); David Gottlieb, Westmead (AU); Grant Logan, Westmead (AU)

(73) Assignee: HAEMALOGIX PTY. LTD., Eveleigh (AU)

( * ) Notice: Subject to any disclaimer, the term of this patent is extended or adjusted under 35 U.S.C. 154(b) by 438 days.

(21) Appl. No.: 15/568,271

(22) PCT Filed: Apr. 25, 2016

(86) PCT No.: PCT/US2016/029203
§ 371 (c)(1),
(2) Date: Oct. 20, 2017

(87) PCT Pub. No.: WO2016/172703
PCT Pub. Date: Oct. 27, 2016

(65) Prior Publication Data
US 2018/0228892 A1    Aug. 16, 2018

Related U.S. Application Data

(60) Provisional application No. 62/158,407, filed on May 7, 2015, provisional application No. 62/151,968, filed on Apr. 23, 2015.

(51) Int. Cl.
| | | |
|---|---|---|
| *A61K 39/395* | (2006.01) | |
| *C07K 16/30* | (2006.01) | |
| *A61K 38/20* | (2006.01) | |
| *C07K 14/725* | (2006.01) | |
| *C07K 14/705* | (2006.01) | |
| *C07K 16/28* | (2006.01) | |
| *C12N 5/0783* | (2010.01) | |
| *A61K 35/17* | (2015.01) | |
| *C07K 14/54* | (2006.01) | |
| *A61K 39/00* | (2006.01) | |

(52) U.S. Cl.
CPC ............ *A61K 39/395* (2013.01); *A61K 35/17* (2013.01); *A61K 38/204* (2013.01); *C07K 14/5412* (2013.01); *C07K 14/5434* (2013.01); *C07K 14/7051* (2013.01); *C07K 14/70521* (2013.01); *C07K 16/2887* (2013.01); *C07K 16/2896* (2013.01); *C07K 16/30* (2013.01); *C12N 5/0636* (2013.01); *A61K 2039/505* (2013.01); *C07K 2317/53* (2013.01); *C07K 2317/56* (2013.01); *C07K 2319/035* (2013.01); *C12N 2510/00* (2013.01)

(58) Field of Classification Search
None
See application file for complete search history.

(56) References Cited

U.S. PATENT DOCUMENTS

| 7,344,715 B2 | 3/2008 | Raison et al. |
| 7,556,803 B2 | 7/2009 | Raison et al. |
| 2009/0068199 A1* | 3/2009 | Chessler ............ C07K 16/2863 514/1.1 |
| 2010/0330046 A1* | 12/2010 | Comer ................. A61K 38/208 424/93.7 |
| 2012/0114555 A1 | 5/2012 | Hutchinson et al. |
| 2013/0280285 A1 | 10/2013 | Schönfeld et al. |

FOREIGN PATENT DOCUMENTS

| CN | 1551783 A | 12/2004 |
| JP | 2005-504018 A | 2/2005 |
| JP | 2012-522811 A | 9/2012 |
| WO | WO 2003/004056 A1 | 1/2003 |
| WO | WO 2004/050836 A2 | 6/2004 |
| WO | WO 2010/115238 A1 | 10/2010 |
| WO | WO 2014/100689 A1 | 6/2014 |
| WO | WO 2014/190273 A1 | 11/2014 |
| WO | WO 2015/009740 A2 | 1/2015 |
| WO | WO 2015/164739 A1 | 10/2015 |
| WO | WO 2016/172703 A2 | 10/2016 |

OTHER PUBLICATIONS

Pegram et al (Blood, 119(18):4133-4141, 2012).*
Regenmortel, Marc, (Epitope Mapping Protocols, 2009).*
Airoldi, et al. "Constitutive expression of IL-12Rβ2 on human multiple myeloma cells delineates a novel therapeutic target." Blood (2008); 112(3): 750-759.
Armour, et al., "Differential binding to human FcgammaRIIa and FcgammaRIIb receptors by human IgG wildtype and mutant antibodies." Mol Immunol. (2003); 40(9): 585-593.
Bird et al., "Single-chain antigen-binding proteins." Science (1988); 242 (4877): 423-426.
Chinnasamy, et al, "Local delivery of interleukin-12 using T cells targeting VEGF receptor-2 eradicates multiple vascularized tumors in mice." Clin Cancer Res. (2012); 18(6): 1672-1683.
Chung, et al., "Characterization of the chicken beta-globin insulator." Proc Natl Acad Sci USA. (1997); 94(2): 575-580.
Clemenceau, et al., "In Vitro and In Vivo Comparison of Lymphocytes Transduced with a Human CD 16 or with a Chimeric Antigen Receptor Reveals Potential Off-Target Interactions due to the IgG2 CH2-CH3 CAR-Spacer." J Immunol Res. (2015); 2015: 482089.

(Continued)

*Primary Examiner* — Brad Duffy
(74) *Attorney, Agent, or Firm* — Cooley LLP

(57) ABSTRACT

The present invention provides compositions and methods for treating KMA-expressing malignancies including chimeric antigen receptors (CARs) and T cells containing CARs (CAR T-cells). The invention also provides methods and compositions comprising CAR T-cells co-expressing other anti-tumoral agents including cytokines and antibodies.

18 Claims, 16 Drawing Sheets

Specification includes a Sequence Listing.

(56) References Cited

OTHER PUBLICATIONS

Demartis, A, et al., "Interleukin 6 receptor superantagonists are potent inducers of human multiple myeloma cell death." Cancer Res. (1996); 56(18): 4213-4218.
Fiering, et al., "Single cell assay of a transcription factor reveals a threshold in transcription activated by signals emanating from the T-cell antigen receptor." Genes Dev. (1990); 4(10): 1823-1834.
Garfall, et al., "Immunotherapy with Chimeric Antigen Receptors for Multiple Myeloma." Discovery Medicine (2014); 17(91): 37-46.
Goodnow, et al., "Structural analysis of the myeloma-associated membrane antigen KMA." J Immunol. (1985); 135(2): 1276-1280.
Goodwin, et al., "The 3'-flanking sequence of the bovine growth hormone gene contains novel elements required for efficient and accurate polyadenylation." J Biol Chem. (1992); 267(23): 16330-16334.
Hombach and Abken, "Costimulation by chimeric antigen receptors revisited the T cell antitumor response benefits from combined CD28-OX40 signalling." International Journal of Cancer (2011); 129(12): 2935-2944.
Hombach et al., "Adoptive immunotherapy with genetically engineered T cells: modification of the IgG1 Fc 'spacer' domain in the extracellular moiety of chimeric antigen receptors avoids 'off-target' activation and unintended initiation of an innate immune response." Gene Ther. (2010);17(10): 1206-1213.
Hudecek, et al., "The nonsignaling extracellular spacer domain of chimeric antigen receptors is decisive for in vivo antitumor activity." Cancer Immunol Res. (2015); 3(2): 125-135.
Huston et al., "Protein engineering of antibody binding sites: recovery of specific activity in an anti-digoxin single-chain Fv analogue produced in *Escherichia coli*." Proc Natl Acad Sci U.S.A. (1988); 85(16): 5879-5883.
Hutchinson, et al., "Characterization of a unique conformational epitope on free immunoglobulin kappa light chains that is recognized by an antibody with therapeutic potential." Mol. Immunol. (2011); 48 (9-10): 1245-1252.
International Preliminary Reporton Patentability for International Application No. PCT/US2016/029203, dated Oct. 24, 2017, 8 pages.
International Search Report and Written Opinion for International Application No. PCT/US2016/029203, dated Oct. 14, 2016, 13 pages.
John, et al., "Truncated galectin-3 inhibits tumor growth and metastasis in orthotopic nude mouse model of human breast cancer." Clin Cancer Res. (2003); 9(6): 2374-2383.
Miller, et al., "Cloning of DNA complementary to bovine prolactin mRNA. Endocrinology." (1980); 107(3): 851-853.
Miller, et al., "Molecular cloning of DNA complementary to bovine growth hormone Mrna." J Biol Chem. (1980); 255(16): 7521-7524.
Mirandola, et al., "Galectin-3C inhibits tumor growth and increases the anticancer activity of bortezomib in a murine model of human multiple myeloma." PLoS One (2011); 6(7): e21811.
Pegram, et al., "Tumor-targeted t cells modified to secrete IL-12 eradicate systemic tumors without need for prior conditioning." Blood (2012); 119(180): 4133-4141.
Philip, et al., "A Highly Compact Epitope-Based Marker-Suicide Gene for More Convenient and Safer T-Cell Adoptive Immunotherapy," ASH Annual Meeting Abstracts (2010); 116(21): 1473.
Ramanayake, et al., "Low-cost generation of Good Manufacturing Practice-grade CD19-specific chimeric antigen receptor-expressing T cells using piggyBac gene transfer and patient-derived materials." Cytotherapy (2015); 17(9): 1251-1267.

Rossig, et al., "Adoptive cellular immunotherapy with CD19-specific T cells." Klin Padiatr. (2005); 217(6): 351-356.
Savino, et al., "Generation of interleukin-6 receptor antagonists by molecular-modeling guided mutagenesis of residues important for gp130 activation." EMBO J. 1994; 13(6): 1357-1367.
Savino, et al., "Rational design of a receptor super-antagonist of human interleukin-6." EMBO J. (1994); 13(24): 5863-5870.
Shields, et al."High resolution mapping of the binding site on human IgG1 for Fc gamma RI, Fc gamma RII, Fc gamma RIII, and FcRn and design of IgG1 variants with improved binding to the Fc gamma R." J Biol Chem. (2001); 276(9): 6591-6604.
Sporeno, et al., "Human interleukin-6 receptor super-antagonists with high potency and wide spectrum on multiple myeloma cells." Blood. (1996); 87(11): 4510-4519.
Vera, et al., "T lymphocytes redirected against the κ light chain of human immunoglobulin efficiently kill mature B lymphocyte-derived malignant cells." Blood (2006); 108(12): 3890-3897.
Wang, et al. "Bortezomib and IL-12 produce synergetic anti-multiple myeloma effects with reduced toxicity to natural killer cells." Anticancer Drugs (2014); 25(3): 282-288.
Zhang, et al. "Improving adoptive T cell therapy by targeting and controlling IL-12 expression to the tumor environment." Mol. Ther. (2011); 19(4): 751-759.
Extended European Search Report for European Application No. 16784085.9, dated Oct. 30, 2018, 9 pages.
Invitation to Pay Additional Fees for International Application No. PCT/US2016/029203, dated Aug. 10, 2016, 2 pages.
[Author Unknown] ATCC Product Sheet, HP6053 (ATCC® CRL-1758™), Description: Organism: *Mus musculus* (B cell); *Mus musculus* (myeloma), mouse (B cell); mouse (myeloma) Isotype: IgG1, Year: 2007, 2 pages.
Asvadi, et al., "MDX-1097 induces antibody-dependent cellular cytotoxicity against kappa multiple myeloma cells and its activity is augmented by lenalidomide". Br J Haematol. (May 2015); 169(3): 333-343, and Supplemental Data, 21 pages. Epub Feb. 3, 2015.
Davila, et al., "Chimeric antigen receptors for the adoptive T cell therapy of hematologic malignancies". Int J Hematol. (Apr. 2014); 99(4): 361-371. Epub Dec. 6, 2013.
Hutchinson, et al., "Free Ig Light Chains Interact with Sphingomyelin and Are Found on the Surface of Myeloma Plasma Cells in an Aggregated Form". J Immunol (Oct. 1, 2010); 185(7): 4179-4188. Epub Sep. 3, 2010.
Long, et al., "4-1BB Costimulation Ameliorates T Cell Exhaustion Induced by Tonic Signaling of Chimeric Antigen Receptors". Nat Med. (Jun. 2015); 21(6): 581-590. Epub May 4, 2015.
Nakazawa, Yozo, "Gene-modified T-cell Therapy Using Chimeric Antigen Receptor". The Shinshu Medical Journal (2013); 61(4): 197-203, and Machine English translation, 15 pages.
[Author Unknown] Product sheet for Anti-Kappa (TB 28-2); BD biosciences (Oct. 2013); 8 pages.
Ocqueteau, Mauricio, et al. "Do myelomatous plasma cells really express surface immunoglobulins?." Haematologica (1996); 81.5: 460-463.
Patnaik, A., et al., "Phase I ficlatuzumab monotherapy or with erlotinib for refractory advanced solid tumours and multiple myeloma". British Journal of Cancer. (Jul. 15, 2014); 111(2): 272-280. Epub Jun. 5, 2014.

\* cited by examiner

Figure 6A, Figure 6B, Figure 6C

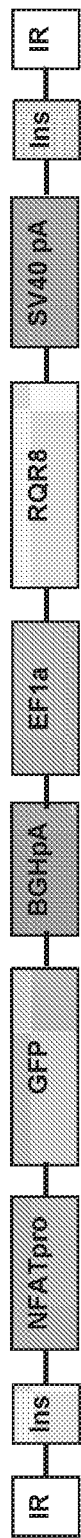
Figure 9
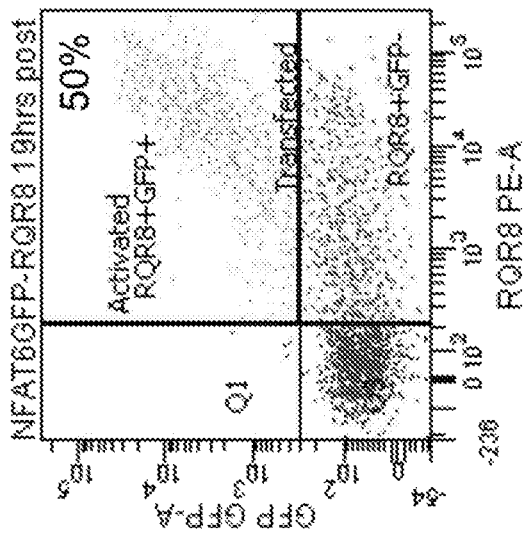
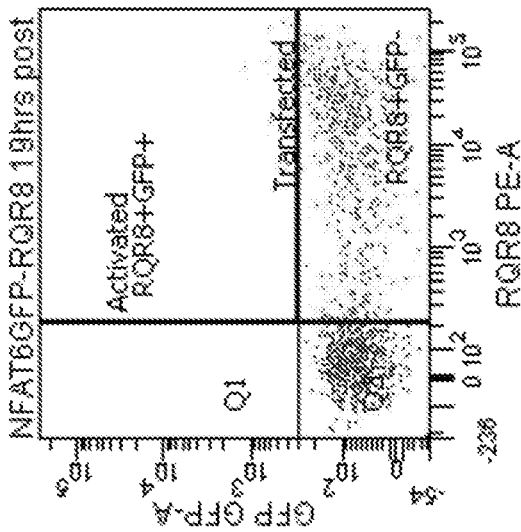
Figure 10

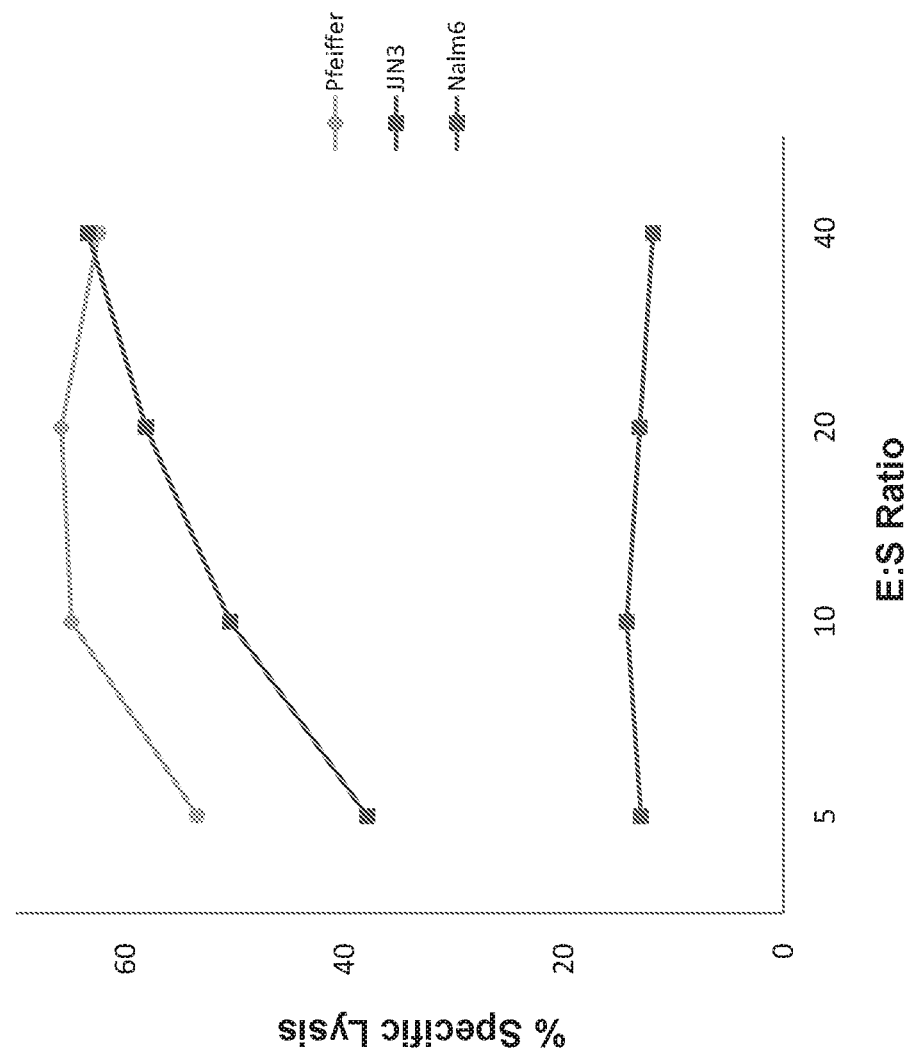

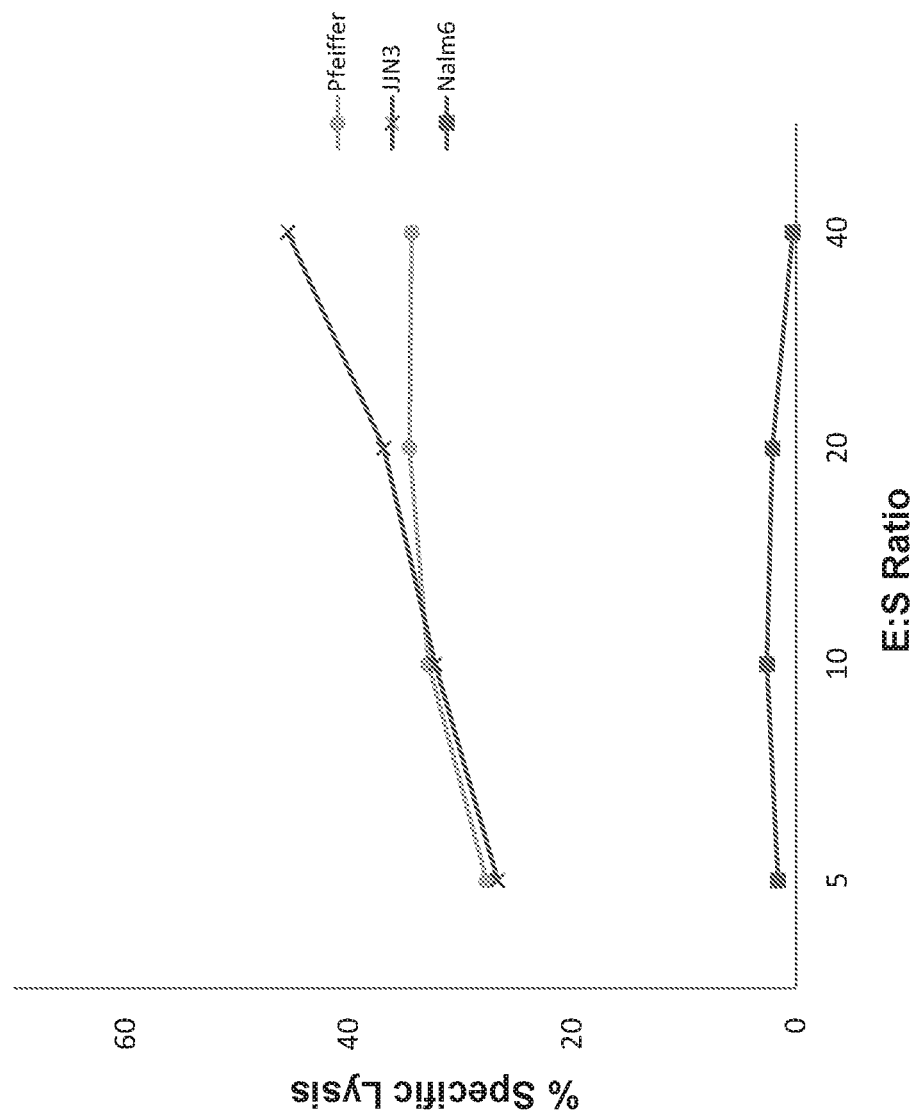

KAPPA MYELOMA ANTIGEN CHIMERIC ANTIGEN RECEPTORS AND USES THEREOF

CROSS-REFERENCE TO U.S. NON-PROVISIONAL APPLICATIONS

This application is a national phase of International Application No. PCT/US16/29203, filed Apr. 25, 2016, which claims priority from U.S. Provisional Application Ser. No. 62/151,968, filed Apr. 23, 2015, and U.S. Provisional Application Ser. No. 62/158,407, filed May 7, 2015 each of which is incorporated by reference herein in its entirety for all purposes.

STATEMENT REGARDING SEQUENCE LISTING

The contents of the text file submitted electronically herewith are incorporated herein by reference in their entirety: A computer readable format copy of the Sequence Listing (filename: HMLX_002_02US_2nd_Sub_SeqList_ST25.txt, date recorded: Nov. 4, 2021, file size 63.1 kilobytes).

BACKGROUND OF THE INVENTION

Multiple myeloma (MM) is a malignancy of bone marrow plasma cells which despite recent advances in therapy, remains incurable. Its clinical course is characterized by an initial response to therapy, followed by repeated relapse with eventual resistance to all forms of treatment. It is also associated with significant morbidity and disability both due to the disease itself and toxicity from available treatments.

Multiple myeloma is characterized by malignant plasma cells which secrete either a kappa or lambda light chain restricted monoclonal paraprotein. Kappa restriction occurs in 60% of myeloma patients and the expression of kappa myeloma antigen (KMA) is highly restricted to multiple myeloma and B-cell malignancies. KappaMab is a KMA-specific monoclonal antibody which has demonstrated safety and efficacy in phase I and II clinical trials.

Treatment with monoclonal antibodies alone is not curative with incomplete eradication of the tumor leading to eventual relapse. This may be due to inadequate penetration of antibody into the tumor (via passive diffusion), heterogeneity of antigen expression on tumor cells or resistance of tumor cells to mechanisms of antibody dependent cytotoxicity. Thus, there is a need for effective therapies with low toxicity which can provide long term disease cure.

Chimeric Antigen Receptor bearing T cells (CAR T-cells) represent a possible solution to this problem. CAR T-cells incorporate the antigen binding domain of monoclonal antibodies with one or more intracellular signaling domain(s) of T cells to produce a localized, tumor specific immune response. CAR T-cells have several advantages over monoclonal antibodies: they actively migrate into the tumor, proliferate in response to antigen bearing tumor cells, secrete factors that recruit other arms of the immune response and can survive long term to provide ongoing protection from relapse. Another benefit of a CAR-T cell over an antibody therapeutic targeting the same antigen is that the CAR T-cell may also be further modified to enhance safety and function. For example, a T cell can be modified to include expression of a homing receptor which enhances T cell specificity and the ability of the T cell(s) to infiltrate cancer cells or tumors or they may include an "off switch" that can function to eliminate cells when toxicity occurs. Furthermore, and importantly for the treatment of multiple myeloma and its related disorders, the T cell may be modified to express additional biologically active or pharmaceutically active molecules that may enhance the anti-tumor response, such as, for example, tumor suppressive cytokines. As described herein, the current inventors have designed novel CAR constructs which are able to specifically bind to a particular conformational KMA epitope expressed only on MM cells and have engineered CAR T-cells to express an extracellular antigen binding domain specific for this epitope and an intracellular T cell signaling domain alone or in combination with the expression of other anti-tumoral immune mediators.

SUMMARY OF THE INVENTION

The present invention is drawn to chimeric antigen receptors (CAR) that are specific for kappa myeloma antigen (KMA) but contain intracellular signaling domains capable of triggering an anti-KMA T cell response, T cells containing such CARs and method of treating multiple myeloma and related disorders by administering T cells expressing KMA-specific CARs. The resulting CAR T-cells are able to mediate a targeted immune response against cancer cells while avoiding unwanted side effects associated with systemic delivery of monoclonal antibodies and/or anti-tumoral cytokines.

In one embodiment, the chimeric antigen receptors (CARs) of the present invention comprise one or more intracellular signaling domains and an extracellular antigen binding domain that specifically recognizes kappa myeloma antigen (KMA). In one embodiment, the intracellular signaling domain is one or more co-stimulatory endodomains. In a further embodiment, the one or more co-stimulatory domain is one or more of a CD28 domain, a CD3ζ domain, a 4-1BB domain, or an OX-40 domain or combinations thereof. In one embodiment, the one or more co-stimulatory endodomains of the CAR comprises a CD3ζ domain and a CD28 domain. In another embodiment, the one or more co-stimulatory endodomains of the CAR comprises a CD3ζ domain, and an OX-40 domain. In still another embodiment, the one or more co-stimulatory endodomains of the CAR comprises a CD3ζ domain, a CD28 domain and an OX-40 domain. In still another embodiment, the one or more co-stimulatory endodomains of the CAR comprises a CD3ζ domain and a 4-1BB domain. In still another embodiment, the one or more co-stimulatory endodomains of the CAR comprises a CD3ζ domain, a CD28 domain and a 4-1BB domain. In still another embodiment, the one or more co-stimulatory endodomains of the CAR comprises a CD3ζ domain, a 4-1BB domain and an OX-40 domain.

In one embodiment, the extracellular binding domain comprises a single chain variable fragment (scFv) that specifically recognizes KMA. In still another embodiment, the scFv comprises the complemetarity determining regions (CDRs) derived from KappaMab. In still another embodiment the scFv comprises the VL CDRs of SEQ ID NOs: 6-8. In yet another embodiment, the scFV comprises the VL region of SEQ ID NO: 21. In still another embodiment the scFv comprises the VH CDRs of SEQ ID NOs: 3-5. In yet another embodiment, the scFV comprises the VH region of SEQ ID NO: 22. In still a further embodiment, the scFv comprises the VL CDRs of SEQ ID NOs: 6-8 and the VH CDRs of SEQ ID NOs: 3-5. In yet a further embodiment, the scFv comprises the VL region of SEQ ID NO: 21 and the VH region of SEQ ID NO: 22. In one embodiment, the VL chain of SEQ ID NO: 2 and VH chain of SEQ ID NO: 1 are attached via a glycine-serine linker. In one embodiment, the VL region of SEQ ID NO: 21 and VH region of SEQ ID NO: 22 are attached via a glycine-serine linker. In still another embodiment, the linker is a $(Gly_4Ser)_x$ where X is 1-5. In still another embodiment, the glycine-serine linker is a 15-20 amino acid linker. In still another embodiment, the linker is a 15 amino acid glycine serine linker and comprises $(Gly_4Ser)_3$. In one embodiment, the $(Gly_4Ser)_3$ linker is SEQ ID NO: 23. In one embodiment, the scFv is attached to the one or more intracellular signaling domains with a spacer. In still another embodiment, scFv is attached to the one or more intracellular domains by a spacer that comprises an immunoglobulin constant region. In one embodiment, the immunoglobulin constant region comprises one or more of an IgG hinge, an IgG CH2 and an IgG CH3 domain. In a particular embodiment, the immunoglobulin constant region comprises an immunoglobulin hinge domain. In still another embodiment, the immunoglobulin constant region comprises an immunoglobulin CH3 domain. In still another embodiment, the immunoglobulin constant region comprises an IgG CH2 domain. In still another embodiment, the scFv is attached to the one or more intracellular domains by a spacer that comprises a CD8a domain. In one embodiment, the spacer is attached to the scFV via a glycine-serine linker. In still another embodiment, the linker is a $(Gly_4Ser)_x$ where X is 1-5. In still another embodiment, the glycine-serine linker is a 15-20 amino acid linker. In still another embodiment, the linker is a 15 amino acid glycine serine linker and comprises $(Gly_4Ser)_3$. In one embodiment, the $(Gly_4Ser)_3$ linker is SEQ ID NO: 23.

In one embodiment, the invention provides T cells comprising chimeric antigen receptors (CAR T-cells). In one embodiment, the CAR T-cells comprise CARs comprising one or more intracellular signaling domains and an extracellular binding domain. In a particular embodiment, the extracellular binding domain specifically recognizes a kappa myeloma antigen. In one embodiment the CAR T-cells are further engineered to express one or more additional biological molecules. In one embodiment, the additional one or more molecules comprise IL-12 and/or SANT7 and/or Galectin −3C (GAL3C). In one embodiment, the CAR T-cells express a single chain polypeptide comprising one IL-12 p35 subunit and one IL-12 p40 subunit joined by a flexible linker. In one embodiment the IL-12 p35 and IL-12 p40 are joined by a $(G_4S)_3$ linker. In one embodiment the single chain IL-12 polypeptide forms a bioactive IL-12 p70 heterodimer. In one embodiment, the CAR T-cell expresses IL-12 and a selectable marker. In one embodiment, the one or more biological molecules is SANT7. In one embodiment, the CAR T-cell expresses GAL3C. In one embodiment, the CAR T-cell expresses GAL3C and a selectable marker. In one embodiment, the CAR T-cell expresses SANT7 and GAL3C. In one embodiment, the CAR T-cell expresses SANT7, GAL3C and a selectable marker. In one embodiment, the CAR T-cell expresses IL-12 and GAL3C. In one embodiment, the CAR T-cell expresses IL-12, GAL3C and a selectable marker. In one embodiment, the CAR T-cell expresses SANT7 and a selectable marker. In one embodiment, the CAR T-cell expresses IL-12, and SANT7. In one embodiment, the CAR T-cell expresses IL-12, SANT7 and a selectable marker. In one embodiment, the CAR T-cell expresses IL-12, SANT7 and GAL3C. In one embodiment, the CAR T-cell expresses IL-12, SANT7, GAL3C and a selectable marker.

In one embodiment, the CAR T-cells of the current invention also express a hepatocyte growth factor (HGF) binding protein that is capable of inhibiting HGF signaling and effector function. In one aspect, the HGF binding protein is an antibody or fragment thereof.

In one aspect, the current invention provides a method for producing a genetically modified T cell comprising introducing an expression vector encoding a CAR comprising one or more intracellular signaling domains and an extracellular antigen binding domain into a T cell. In a particular embodiment, the extracellular antigen binding domain specifically recognizes KMA. In one embodiment, the expression vector is a transposable vector expression system. In certain embodiments, the expression vector is a PiggyBac transposon expression vector. In another embodiment the expression vector is a viral vector. In one embodiment the viral vector is a lentiviral vector or a retroviral vector. In one embodiment, the expression vector is introduced into the cells by electroporation. In one embodiment, the one or more intracellular signaling domains in the CAR is one or more co-stimulatory endodomains. In a further embodiment, the one or more co-stimulatory domain is one or more of a CD28 domain, a CD3ζ domain, a 4-1BB domain, or an OX-40 domain or combinations thereof. In one embodiment, the one or more co-stimulatory endodomains of the CAR comprises a CD3ζ domain and a CD28 domain. In another embodiment, the one or more co-stimulatory endodomains of the CAR comprises a CD3ζ domain, and an OX-40 domain. In still another embodiment, the one or more co-stimulatory endodomains of the CAR comprises a CD3ζ domain, a CD28 domain and an OX-40 domain. In still another embodiment, the one or more co-stimulatory endodomains of the CAR comprises a CD3ζ domain and a 4-1BB domain. In still another embodiment, the one or more co-stimulatory endodomains of the CAR comprises a CD3ζ domain, a CD28 domain and a 4-1BB domain. In still another embodiment, the one or more co-stimulatory endodomains of the CAR comprises a CD3ζ domain, a 4-1BB domain and an OX-40 domain. In one embodiment, the extracellular binding domain comprises a single chain variable fragment (scFv) that specifically recognizes KMA. In still another embodiment, the scFv comprises the complemetarity determining regions (CDRs) derived from KappaMab. In still another embodiment the scFv comprises the VL CDRs of SEQ ID NOs: 6-8. In yet another embodiment, the scFV comprises the VL region of SEQ ID NO: 21. In still another embodiment the scFv comprises the VH CDRs of SEQ ID NOs: 3-5. In yet another embodiment, the scFV comprises the VH region of SEQ ID NO: 22. In still a further embodiment, the scFv comprises the VL CDRs of SEQ ID NOs: 6-8 and the VH CDRs of SEQ ID NOs: 3-5. In yet a further embodiment, the scFv comprises the VL region of SEQ ID NO: 21 and the VH region of SEQ ID NO: 22. In one embodiment, the VL chain of SEQ ID NO: 2 and VH chain of SEQ ID NO: 1 are attached via a glycine-serine linker. In one embodiment, the VL region of SEQ ID NO: 21 and VH region of SEQ ID NO: 22 are attached via a glycine-serine linker. In still another embodiment, the glycine-serine linker is a 15-20 amino acid linker. In still another embodiment, the linker is a 15 amino acid glycine serine linker and comprises $(Gly_4Ser)_3$. In one embodiment, the $(Gly_4Ser)_3$ linker is SEQ ID NO: 23. In one embodiment, the scFv is attached to the one or more intracellular signaling domains with a spacer. In still another embodiment, scFv is attached to the one or more intracellular domains by a spacer that comprises an immunoglobulin constant region. In one embodiment, the immunoglobulin constant region comprises one or more of an IgG hinge, an IgG CH2 and an IgG CH3 domain. In a particular embodiment, the immunoglobulin constant region comprises an immunoglobulin hinge domain. In still another embodiment, the immunoglobulin constant region comprises an immunoglobulin CH3 domain. In still another embodiment, the immunoglobulin constant region comprises an IgG CH2 domain. In still another embodiment, the scFv is attached to the one or more intracellular domains by a spacer that comprises a CD8a domain. In one embodiment, the spacer is attached to the scFV via a glycine-serine linker. In still another embodiment, the linker is a $(Gly_4Ser)_x$ where X is 1-5. In still another embodiment, the glycine-serine linker is a 15-20 amino acid linker. In still another embodiment, the linker is a 15 amino acid glycine serine linker and comprises $(Gly_4Ser)_3$. In one embodiment, the $(Gly_4Ser)_3$ linker is SEQ ID NO: 23. In one embodiment the method further comprises introducing one or more additional expression vectors engineered to express one or more additional biological molecules. In one embodiment, the additional one or more molecules comprise IL-12 and/or SANT7 and/or GAL3C. In one embodiment, the one or more additional expression vectors comprise a sequence encoding a single chain polypeptide comprising one IL-12 p35 subunit and one IL-12 p40 subunit joined by a flexible linker. In one embodiment the IL-12 p35 and IL-12 p40 are joined by a $(G_4 5)_3$ linker. In one embodiment the sequence encoding a single chain IL-12 polypeptide encodes a bioactive IL-12 p70 heterodimer. In one embodiment, the expression vector expressing the one or more biologically active agents also comprises a selectable marker. In one embodiment the expression vector comprises a sequence encoding a single chain IL-12 polypeptide comprising IL-12 p35 and IL-12 p40 joined with a flexible linker and a selectable marker joined to the single chain IL-12 with a 2A ribosomal skip. In one embodiment, the one or more biological molecules is SANT7. In one embodiment, the expression vector expressing one or more biologically active agents comprises SANT7 and a selectable marker. In one embodiment the sequence encoding SANT7 and the selectable marker are joined by a 2A ribosomal skip sequence. In one embodiment, the expression vector expressing one or more biologically active agents comprises GAL3c and a selectable marker. In one embodiment, the sequence encoding GAL3C and the selectable marker are joined by a ribosomal skip sequence. In one embodiment, the CAR T-cell comprises IL-12, SANT7 and a selectable marker. In one embodiment, the sequence encoding the IL-12 is linked to the selectable marker via a 2A ribosomal skip and the sequence encoding SANT7 is connected to the sequence encoding IL-12 by an additional 2A ribosomal skip. In one embodiment, the CAR T-cell comprises GAL3C, SANT7 and a selectable marker. In one embodiment, the sequence encoding the GAL3C is linked to the selectable marker via a 2A ribosomal skip and the sequence encoding SANT7 is connected to the sequence encoding GAL3C by an additional 2A ribosomal skip. In one embodiment, the CAR T-cell comprises IL-12, GAL3C and a selectable marker. In one embodiment, the sequence encoding the IL-12 is linked to the selectable marker via a 2A ribosomal skip and the sequence encoding GAL3C is connected to the sequence encoding IL-12 by an additional 2A ribosomal skip. In one embodiment, the CAR T-cell comprises GAL3C, SANT7, IL-12 and a selectable marker. In one embodiment, the sequence encoding each of GAL3C, SANT7, IL-12 and the selectable marker are connected via 2A ribosomal skip sequences.

In one embodiment, a method for treating a KMA-expressing malignancy is provided. In one embodiment, the KMA-expressing malignancy is a B cell malignancy. In a further embodiment, the B-cell malignancy is multiple myeloma, Waldenstroms macroglobulinemia, diffuse large B cell lymphoma (DLBCL), or amyloidosis. In a particular embodiment, the method includes administering to a subject with multiple myeloma, Waldenstroms macroglobulinemia, diffuse large B cell lymphoma (DLBCL), amyloidosis or another B cell malignancy expressing KMA genetically modified T cells engineered to express one or more intracellular signaling domains and an extracellular antigen binding domain that specifically recognizes KMA. In one embodiment, the one or more intracellular signaling domains in the CAR is one or more co-stimulatory endodomains. In a further embodiment, the one or more co-stimulatory domain is one or more of a CD28 domain, a CD3ζ domain, a 4-1BB domain, or an OX-40 domain or combinations thereof. In one embodiment, the one or more co-stimulatory endodomains of the CAR comprises a CD3ζ domain and a CD28 domain. In another embodiment, the one or more co-stimulatory endodomains of the CAR comprises a CD3ζ domain, and an OX-40 domain. In still another embodiment, the one or more co-stimulatory endodomains of the CAR comprises a CD3ζ domain, a CD28 domain and an OX-40 domain. In still another embodiment, the one or more co-stimulatory endodomains of the CAR comprises a CD3ζ domain and a 4-1BB domain. In still another embodiment, the one or more co-stimulatory endodomains of the CAR comprises a CD3ζ domain, a CD28 domain and a 4-1BB domain. In still another embodiment, the one or more co-stimulatory endodomains of the CAR comprises a CD3ζ domain, a 4-1BB domain and an OX-40 domain. In one embodiment, the extracellular binding domain comprises a single chain variable fragment (scFv) that specifically recognizes KMA. In still another embodiment, the scFv comprises the complemetarity determining regions (CDRs) derived from KappaMab. In still another embodiment the scFv comprises the VL CDRs of SEQ ID NOs: 6-8. In yet another embodiment, the scFV comprises the VL region of SEQ ID NO: 21. In still another embodiment the scFv comprises the VH CDRs of SEQ ID NOs: 3-5. In yet another embodiment, the scFV comprises the VH region of SEQ ID NO: 22. In still a further embodiment, the scFv comprises the VL CDRs of SEQ ID NOs: 6-8 and the VH CDRs of SEQ ID NOs: 3-5. In yet a further embodiment, the scFv comprises the VL region of SEQ ID NO: 21 and the VH region of SEQ ID NO: 22. In one embodiment, the VL chain of SEQ ID NO: 2 and VH chain of SEQ ID NO: 1 are attached via a glycine-serine linker. In one embodiment, the VL region of SEQ ID NO: 21 and VH region of SEQ ID NO: 22 are attached via a glycine-serine linker. In still another embodiment, the linker is a $(Gly_4Ser)_x$ where X is 1-5. In still another embodiment, the glycine-serine linker is a 15-20 amino acid linker. In still another embodiment, the linker is a 15 amino acid glycine serine linker and comprises $(Gly_4Ser)_3$. In one embodiment, the $(Gly_4Ser)_3$ linker is SEQ ID NO: 23. In one embodiment, the scFv is attached to the one or more intracellular signaling domains with a spacer. In still another embodiment, scFv is attached to the one or more intracellular domains by a spacer that comprises an immunoglobulin constant region. In one embodiment, the immunoglobulin constant region comprises one or more of an IgG hinge, an IgG CH2 and an IgG CH3 domain. In a particular embodiment, the immunoglobulin constant region comprises an immunoglobulin hinge domain. In still another embodiment, the immunoglobulin constant region comprises an immunoglobulin CH3 domain. In still another embodiment, the immunoglobulin constant region comprises an IgG CH2 domain. In still another embodiment, the scFv is attached to the one or more intracellular domains by a spacer that comprises a CD8α domain. In one embodiment, the spacer is attached to the scFV via a glycine-serine linker. In still another embodiment, the linker is a (Gly$_4$Ser)$_x$ where X is 1-5. In still another embodiment, the glycine-serine linker is a 15-20 amino acid linker. In still another embodiment, the linker is a 15 amino acid glycine serine linker and comprises (Gly$_4$Ser)$_3$. In one embodiment, the (Gly$_4$Ser)$_3$ linker is SEQ ID NO: 23. In another embodiment, the genetically modified T cells are further engineered to express one or more additional biological molecules. In one embodiment, the additional one or more molecules comprise IL-12 and/or SANT7 and or GAL3C. In one embodiment, the CAR T-cells express a single chain polypeptide comprising one IL-12 p35 subunit and one IL-12 p40 subunit joined by a flexible linker. In one embodiment the IL-12 p35 and IL-12 p40 are joined by a (G$_4$S)$_3$ linker. In one embodiment the single chain IL-12 polypeptide forms a bioactive IL-12 p70 heterodimer. In one embodiment, the CAR T-cell expresses IL-12 and a selectable marker. In one embodiment, the one or more biological molecules is SANT7. In one embodiment, the CAR T-cell expresses SANT7 and a selectable marker. In one embodiment the selectable marker is GAL3C. In one embodiment, the CAR T-cell expresses GAL3C and a selectable marker. In one embodiment, the CAR T-cell expresses IL-12, SANT7 and a selectable marker. In one embodiment, the CAR T-cell expresses IL-12, GAL3C and a selectable marker. In one embodiment, the CAR T-cell expresses SANT7, GAL3C and a selectable marker. In one embodiment, the CAR T-cell expresses IL-12, SANT7, GAL3C and a selectable marker.

In a further embodiment, the method includes further administering to a patient with multiple myeloma, Waldenstroms macroglobulinemia, diffuse large B cell lymphoma (DLBCL), amyloidosis or another B cell malignancy expressing KMA an HGF binding protein. In one embodiment, the HGF binding protein is an antibody or fragment thereof. In one embodiment, an expression vector comprising the HGF binding protein is co-transfected with the expression vector encoding the CAR construct into a T cell such that the resulting CAR T-cell also expresses the HGF binding protein.

In another embodiment, the method includes administering one or more additional biologically or pharmaceutically active agents. In one embodiment, the one or more additional pharmaceutically active agent is a chemotherapeutic agent. In another embodiment, the one or more pharmaceutically active agent is an immunomodulatory drug. In a particular embodiment, the immunomodulatory drug is thalidomide or an analog thereof. In still another embodiment, the thalidomide analog is actimid, lenalidomide, or pomalidomide. In still another embodiment, the additional pharmaceutically active agent is a histone deacetylase inhibitor. In still another embodiment, the histone deacetylase inhibitor is panobinostat, vorinostat, trichostatin A, depsipeptides, phenylbutyrate, valproic acid, belinostat, LAQ824, entinostat, CI944, or mocetinostat. In still another embodiment, the one or more additional biological or pharmaceutically active agents is administered before, during or after treatment with said genetically modified T cells. In still another embodiment, the genetically modified T cells are administered intravenously. In still another embodiment, the generically modified T cells are derived from said patient. In still another embodiment, the genetically modified T cells are not derived from said patient.

In one embodiment, the CAR T-cells of the current invention are administered before, during or after an allogenic stem cell transplant. In still another embodiment, the the CAR T-cells of the current invention are administered before during or after an allogenic stem cell transplant.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIG. 1A shows a single chain variable fragment (scFv) consisting of the parent antibody's light chain variable region (VL) joined to the heavy chain variable region (VH) by a polypeptide linker confers antigen specificity to the CAR. A flexible hinge connects the scFv to the transmembrane and the intracellular signaling domain of a co-stimulatory molecule such as CD28, 4-1 BB or OX-40 followed by CD3 zeta. FIG. 1B shows T-cells transduced with the CAR are activated on encountering tumor cells bearing the target antigen (Ag) leading to tumor cell lysis.

FIG. 4A is flow cytometry analysis of KMA expression on various cell lines; FIG. 4B is interferon-gamma (IFNγ) expression of KMA.CAR-28z transduced (upper plots) and non-transduced (lower plots) CD8$^+$ T cells. FIG. 4C shows the specific lysis of KMA positive and negative cell lines by KMA.CAR-28z transduced T cells.

FIGS. 6A-6C shows the optimization of KMA.CAR FIG. 6A show the initial KMA.CAR-28z construct; FIG. 6B shows constructs with Ig heavy chain hinge and CH3 or hinge alone FIG. 6C shows constructs combining optimal hinge region (opti) with combinations of various costimulatory molecule endodomains and CD3 zeta.

FIG. 8A shows expansion of total cells in CAR T-cell cultures with (left) and without (right) the addition of the KMA expressing JJN3 cell line.

FIG. 8B CAR expression as measured by GFP in cultures with (top plots) and without (bottom plots) the KMA expressing JJN3 cell line. hCH2CH3=KM.CAR_hCH2CH3_28z T-cells;

hCH2CH3mut=KM.CAR_hCH2CH3mut_28TM_41BBz T-cells; h=KM.CAR_h_28TM_41BBz T-cells; CD8a=KM.CAR_8a_28TM_41BBz T-cells.

FIG. 9 shows the structure of the activation inducible transposon casette. IR=inverted repeats; Ins=Insulator flanking the two ends of the gene insert; NFATpro=activation inducible promoter; BGHpA=bovine growth hormone polyadenylation signal; EF1α=human elongation factor-1 alpha promoter; RQR8=marker; SV40=simian virus late polyadenylation signal.

FIG. 10 shows expression of eGFP under activation induced promoter control. Transduced PBMCs stimulated with PMA and Ionomycin (right plot) were assessed for co-expression of RQR8 (x-axis) and eGFP (y-axis) and compared to unstimulated controls (left plot). Transduced cells did not express eGFP in the absence of stimulation. Fifty percent of transduced cells expressed eGFP with stimulation.

Figure 11:

FIG. 11 shows the structure of the activation inducible transposon cassette with CAR and biological. IR=inverted repeats; Ins=Insulator flanking the two ends of the gene insert; NFATpro=activation inducible promoter; BGHpA=bovine growth hormone polyadenylation signal; EFla=human elongation factor-1 alpha promoter; SV40=simian virus late polyadenylation signal.

FIGS. 12A-12B shows KMA-specific interferon-gamma production and cytotoxicity of KM.CAR_hCH2CH3_28z T-cells (FIG. 12A) or KM.CAR_h_28TM_41BBz T-cells (FIG. 12B) standard chromium release assay with KMA+ and KMA− cell lines. KMA positive cell lines used included JJN3, Pfeiffer, NCI-H929, while KMA negative cell lines included Nalm-6 and Molt

DETAILED DESCRIPTION OF THE INVENTION

Unless defined otherwise, all technical and scientific terms used herein have the same meaning as commonly understood by one of ordinary skill in the art to which the invention pertains. Although any methods and material similar or equivalent to those described herein can be used in the practice for testing of the present invention, the preferred materials and methods are described herein. In describing and claiming the present invention, the following definitions will be used. It will also be understood that the terminology used herein is not meant to be limiting but rather is used herein for the purpose of describing particular embodiments.

The articles "a" and "an" are used herein to refer to one or more than one (i.e. to at least one or to one or more) of the grammatical object of the article.

The term "expression vector" as used herein refers to a vector comprising a recombinant nucleic acid sequence comprising at least one expression control sequence operatively linked to the nucleic acid sequence to be expressed. An expression vector comprises all necessary cis acting elements required for expression. Examples of expression vectors include, but are not limited to, plasmids, cosmids, and viruses that encode the recombinant polynucleotide to be expressed. In some embodiments, the expression vector comprises transposable elements that are capable of integrating into the genome, for example, the PiggyBac expression system. In some embodiments, the expression vector is a viral vector that allows for integration of the expression vector contents into the host genome, for example retroviral and lentiviral vectors.

By "chimeric antigen receptor" or "CAR" is meant an engineered receptor that includes an extracellular antigen binding domain and an intracellular signaling domain. While the most common type of CAR comprises a single-chain variable fragment (scFv) derived from a monoclonal antibody fused to a transmembrane and intracellular domain of a T cell co-receptor, such as the CD3ζ chain, the invention described herein is not limited to these domains. Rather, as used herein "chimeric antigen receptor" or "CAR" refers to any receptor engineered to express and extracellular antigen binding domain fused or linked to any intracellular signaling molecule.

As used herein the term "CAR-T cell" refers to a T lymphocyte that has been genetically engineered to express a CAR. The definition of CAR T-cells encompasses all classes and subclasses of T-lymphocytes including CD4−, CD8+ T cells as well as effector T cells, memory T cells, regulatory T cells, and the like. The T lymphocytes that are genetically modified may be "derived" or "obtained" from the subject who will receive the treatment using the generically modified T cells or they may "derived" or "obtained" from a different subject.

By "intracellular signaling domain" is meant the portion of the CAR that is found or is engineered to be found inside the T cell. The "intracellular signaling domain" may or may not also contain a "transmembrane domain" which anchors the CAR in the plasma membrane of a T cell. In one embodiment, the "transmembrane domain" and the "intracellular signaling domain" are derived from the same protein (e.g. CD3ζ) in other embodiments; the intracellular signaling domain and the transmembrane domain are derived from different proteins (e.g. the transmembrane domain of a CD3ζ and intracellular signaling domain of a CD28 molecule, or vice versa).

By "co-stimulatory endodomain" is meant an intracellular signaling domain or fragment thereof that is derived from a T cell costimulatory molecule. A non-limiting list of T cell costimulatory molecules include CD3, CD28, OX-40, 4-1BB, CD27, CD270, CD30 and ICOS. The co-stimulatory endodomain may or may not include a transmembrane domain from the same or different co-stimulatory endodomain.

By "extracellular antigen binding domain" is meant the portion of the CAR that specifically recognizes and binds to the antigen of interest. The "extracellular binding domain" may be derived from a monoclonal antibody. For example, the "extracellular binding domain" may include all or part of an Fab domain from a monoclonal antibody. In certain embodiments, the "extracellular binding domain" includes the complementarity determining regions of a particular monoclonal antibody. In still another embodiment, the "extracellular binding domain" is a single-chain variable fragment (scFv).

By "single-chain variable fragment" or "scFv" is meant a fusion protein of the variable heavy (VH) and variable light (VL) chains of an antibody with a peptide linker between the VL and VH. The linker length and composition vary depending on the antibody portions used, but generally are between about 10 and about 25 amino acids in length. In some embodiments, the peptide linker is a glycine rich to provide for flexibility. In some embodiments, the linker also includes serine and/or threonine which may, without being bound by theory, aid in solubility. In some embodiments, the linker is an amino acid with SEQ ID NO: 23. ScFvs are designed to retain the antigen binding specificity of the parent antibody from which their variable chains were derived despite lacking the immunoglobulin heavy chain. In some embodiments, only the complementary determining regions (CDRs) from the VH and VL are used in the scFV. In some embodiments, the entire VL and VH chains are used.

The term "antibody" as used herein refers to an immunoglobulin molecule which specifically binds to an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, New York; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). As used herein the term "antibody" also encompasses antibody fragments.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

As used herein the term "complementarity determining region" or "CDR" refers to the part of the two variable chains of antibodies (heavy and light chains) that recognize and bind to the particular antigen. The CDRs are the most variable portion of the variable chains and provide the antibody with its specificity. There are three CDRs on each of the variable heavy (VH) and variable light (VL) chains and thus there are a total of six CDRs per antibody molecule.

By "KappaMab" is meant the monoclonal antibody previously termed IST-1097 or MDX-1097. Furthermore, as used herein KappaMab may refer to the full antibody sequence of the KappaMab antibody (See e.g. U.S. Pat. Nos. 7,344,715 and 7,556,803 each of which are hereby incorporated by reference in their entireties.) Additionally, the term "KappaMab" as used herein is used to encompass any polypeptide containing the CDR sequences of SEQ ID NOs: 3-8 and/or the VL sequence of SEQ ID NO: 2 and the VH sequence of SEQ ID NO: 1. The term "KappaMab" as used herein can encompass any polypeptide containing the VL sequence of SEQ ID NO: 21 and the VH sequence of SEQ ID NO: 22. In the compositions and methods of the current invention, KappaMab may include the full monoclonal antibody or any antigen binding fragment thereof including Fab and scFv.

The term "antigen" or "Ag" as used herein is defined as a molecule that is recognized by an immune cell receptor (e.g. a T cell receptor, B cell receptor/Immunogloblulin). In some embodiments, an antigen is a molecule that elicits an immune response. This immune response may involve either antibody production, or the activation of specific immunologically-competent cells, release of cytotoxic mediators or immunostimulatory or regulatory cytokines. The skilled artisan will understand that any macromolecule, including virtually all proteins or peptides, can serve as an antigen.

As used herein the term "specifically binds" or "specifically recognizes" as used in connections with an antibody, antibody fragment or CAR refers to a an antibody, antibody fragment or CAR which recognizes a specific antigen but does not substantially recognize or bind other molecules in a sample.

By "ribosomal skip" is meant an alternative mechanism of translation in which a specific peptide prevents the ribosome of a cell from covalently linking a new inserted amino acid and instead allows it to continue translation thus resulting in a co-translational cleavage of the polyprotein. This process is induced by a "2A ribosomal skip" element or cis-acting hydrolase element (e.g. CHYSEL sequence). In some embodiments, this sequence comprises a non-conserved amino acid sequence with a strong alpha-helical propensity followed by the consensus sequence –D(V/I)ExNPG P, where x=any amino acid. The apparent cleavage occurs between the G and P. In some embodiments, the ribosomal skip element is a 2A ribosomal skip element. The 2A ribosomal skip element can be a 5' T2A ribosomal skip element.

As used herein "immunomodulatory drug" or "IMiD" is a class of drugs that constitute thalidomide and its analogs. Thalidomide analogs include lenalidomide, pomalidomide and apremilast.

As used herein the term "histone deacetyalse inhibitor" or "HDAC inhibitor" or "HDI" refers to a class of compounds that interferes with the function of histone deacetylase. Examples of HDIs include, but are not limited to, hyroxamic acids including, for example, trichostatin A, vorinostat (SAHA), belinostat (PXD101), LAQ824, panobinostat (LBH589); cyclic tripeptides, including for example, depsipeptides and tapoxin B; benzamides, including for example, entinostat (MS-275), CI994 and mocetinostat (MGCD0103); electrophilic ketones; and aliphatic compounds, such as for example, phenylbutyrate and valproic acid.

Kappa Myeloma Antigen and Antibodies

Figure 3:
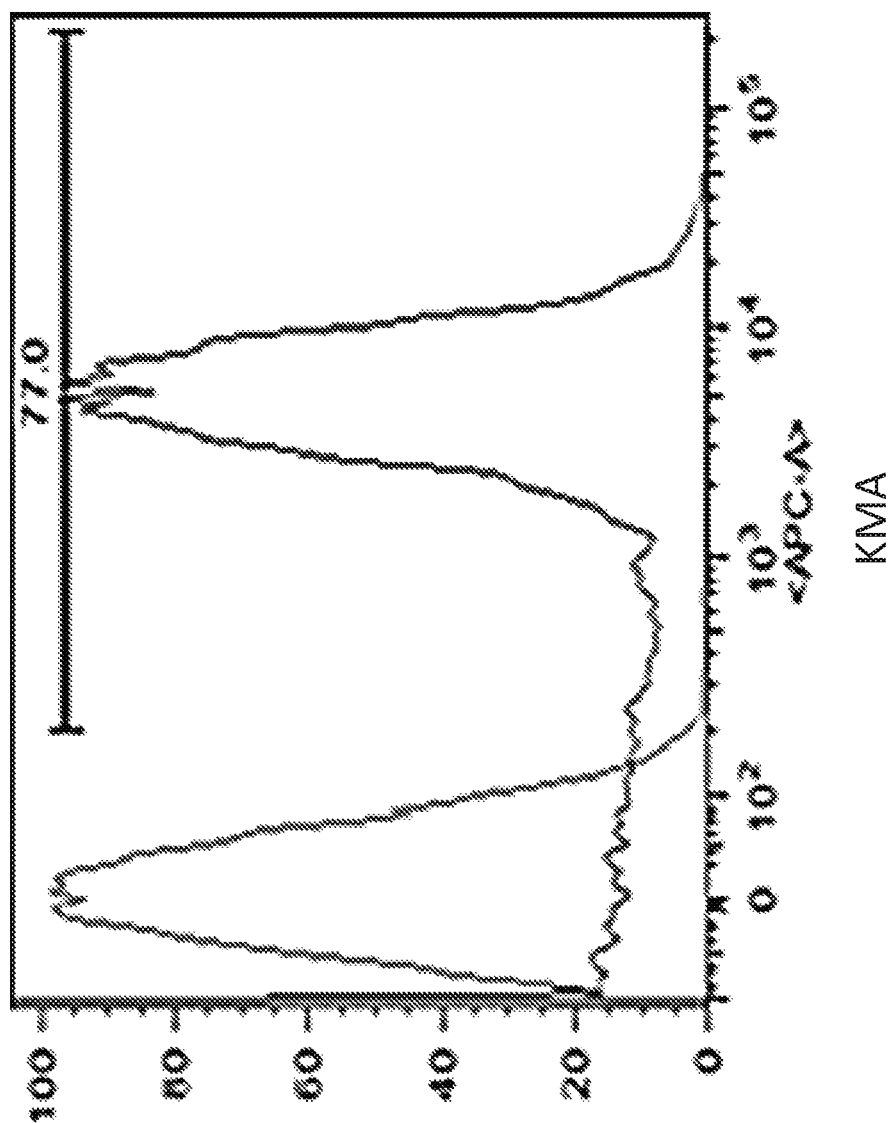
FIG. 3 shows KMA expression on primary myeloma cells.

Kappa myeloma antigen or KMA is a cell membrane antigen that is found on the surface of myeloma cells. Specifically, KMA consists of free kappa light chains expressed in non-covalent association with actin on the cell membrane (Goodnow et al. (1985) J. Immunol. 135:1276). While any antibody that specifically binds to KMA may be used in accordance with the present invention, in a preferred embodiment the KappaMab monoclonal antibody will be used as a basis for the extracellular antigen binding domain of the CARs of the current invention. The monoclonal antibody designated KappaMab (formally designated IST-1097, also known as MDX-1097) binds to a conformational epitope in the switch region of human kappa free light chain that is only available when the kappa chain is not associated with a heavy chain and therefore does not bind to intact kappa-chain containing IgG, IgM, IgE or IgA (Hutchinson et al. (2011) Mol. Immunol.). Typical expression of KMA on primary myeloma cells derived from patient bone marrow biopsies is shown by KappaMab binding in FIG. 3. The KappaMab antibody can comprise the VH chain of SEQ ID NO: 1 and the VL chain of SEQ ID NO: 2. More specifically the KappaMab VH chain can comprise the CDRs of SEQ ID NO: 3-5 and the VL CDRs of SEQ ID NO: 6-8. Additionally, the KappaMab can comprise VH region of SEQ ID NO: 22 and a VL region of SEQ ID NO: 21.

Chimeric Antigen Receptors

Figure 1:
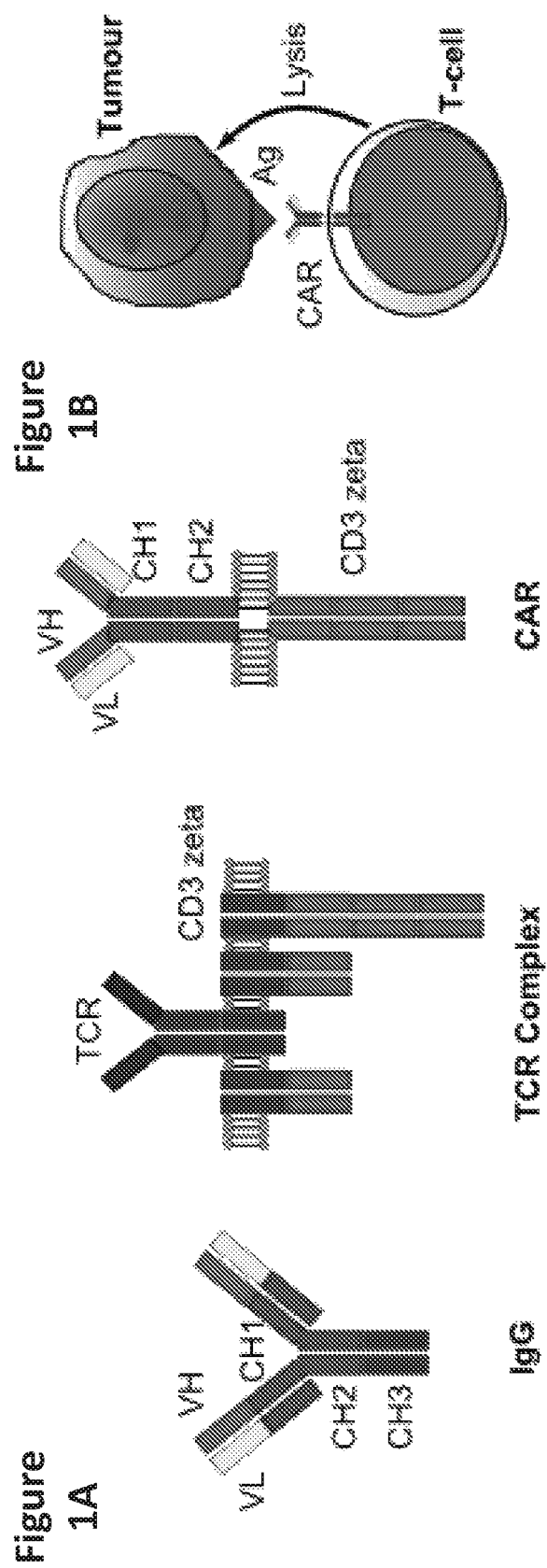
FIGS. 1A-1B shows the structural relationship of CARs to Immunoglobulin (IgG) and the T-cell receptor (TCR)
Figure 2:
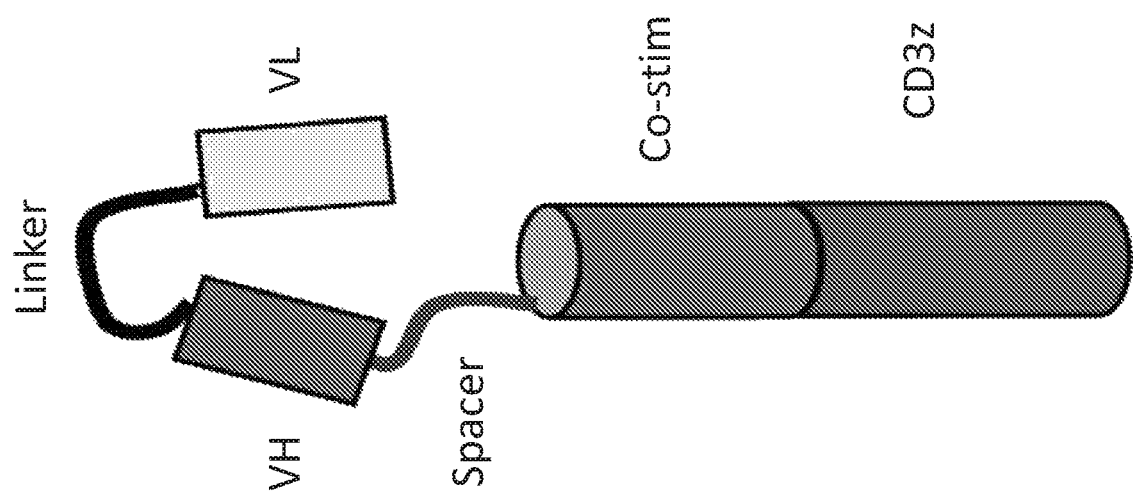
FIG. 2 shows the structural determinants of chimeric antigen receptor function.

Chimeric antigen receptors (CARs) are artificial receptors consisting of the tumor antigen binding regions of monoclonal antibodies and the intracellular activating portion of the T cell receptor complex in a single polypeptide chain held together by a series of linker(s) and spacer(s) (FIGS. 1A-1B). Most commonly, CARs are fusion proteins of single-chain variable fragments (ScFv) fused to the CD3ζ transmembrane domain. However, other intracellular signaling domains such as CD28, 41-BB and Ox40 may be used in various combinations to give the desired intracellular signal. In some embodiments, the CARs provided herein comprise an Ig Heavy Chain Leader peptide. The leader peptide can be SEQ ID NO: 20.

I. Extracellular Antigen Binding Domain

In one embodiment, the CAR of the current invention comprises an extracellular antigen binding domain from a monoclonal antibody that is specific for one or more KMA epitopes expressed on MM cells. In one embodiment, the CAR of the current invention comprises an extracellular antigen binding domain from KappaMab. In one embodiment, the extracellular binding domain comprises the VL CDRs of SEQ ID NOs: 6-8 and VH CDRs of SEQ ID NOs: 3-5. In a particular embodiment, the extracellular binding domain is a scFv comprising the VL (SEQ ID NO: 2) and VH (SEQ ID NO: 1) domains of KappaMab. In another embodiment, the extracellular binding domain is a scFv comprising the VL (SEQ ID NO: 21) and VH (SEQ ID NO: 22) domains of KappaMab.

II. Linker Between VL and VH Domains of KappaMab scFv

In a further embodiment, the KappaMab VL is linked to the KappaMab VH via a flexible linker. Specifically, the flexible linker is a glycine/serine linker of about 10-30 amino acids (for example 30, 25, 20, 19, 18, 17, 16, 15, 14, 13, 12, 11, 10, 9, 8, 7, 6, or 5 amino acids) and comprises the structure $(Gly_4Ser)_3$. In a particular embodiment the linker is 15 amino acids in length. Linker length is an important determinant of a CAR. Without being bound by theory, shorter linkers may enhance affinity but can also lead to intracellular multimer formation thus impairing expression of the CAR whereas longer linkers tend to decrease antigen affinity by moving the VL and VH CDRs further apart in space.

III. Spacers Between Extracellular Antigen Binding Domain and Intracellular Signaling Domain The extracellular antigen binding domain (e.g. KappaMab scFv) is linked to the intracellular signaling domain by the use of a "spacer". The spacer is designed to be flexible enough to allow for orientation of the antigen binding domain in such a way as facilitates antigen recognition and binding. The spacer may derive from immunoglobulins themselves and can include the IgG1 hinge region or the CH2 and/or CH3 region of an IgG. Alternatively, the hinge may comprise all or part of a CD8a chain. The length and flexibility of the spacer(s) is dependent on both the antigen recognition domain as well as the intracellular binding regions and what may be functional and/or optimal for one CAR construct may not be for another CAR. In certain instances the spacer may be designated herein as "opti" (See FIGS. 6A-6C) to signify that optimal spacer identity and length varies depending on the extracellular binding portion used and the intracellular signaling domains selected. In certain embodiment, an IgG hinge alone is used. In other embodiments, the IgG hinge is used together with all or part of IgG CH2 domain. In other embodiments, the IgG hinge is used together with all or part of an IgG CH3 domain. In other embodiments the IgG hinge is used together with all or part of both an IgG CH2 and CH3 domain. In other embodiments, all or part of an IgG CH2 domain is used. In other embodiments, all or part of an IgG CH3 domain is used. In still other embodiments all or part of both an IgG CH2 and CH3 domain is used. In one embodiment, the hinge, CH2 and CH3 domains used in any of the constructs provided herein comprises a C to P mutation in the hinge region at amino acid position 103 of Uniprot P01857). In one embodiment, the hinge, CH2 and CH3 domains used in any of the constructs provided herein is SEQ ID NO: 24. In another embodiment, the hinge is used together with all or part of both an IgG CH2 and CH3 domain, wherein mutations are introduced at amino acids important for CH2 interaction with Fc-receptors. These mutations may mediate improved survival post infusion by decreasing Fc interaction with CAR T-cells provided herein. An example of these mutations can be seen in the KM.CAR_hCH2CH3mut_28TM_41BBz construct shown in Example 3 as provided herein. In a further embodiment still, a CD8α polypeptide is used. In a further embodiment, the spacer (e.g., derived from immunoglobulin domains as described herein) can be attached to the scFV via a flexible linker. Specifically, the flexible linker is a glycine/serine linker of about 10-30 amino acids (for example 30, 25, 20, 19, 18, 17, 16, 15, 14, 13, 12, 11, 10, 9, 8, 7, 6, or 5 amino acids) and comprises the structure $(Gly_4Ser)_x$ where X is 1-5. In other embodiments, the glycine/serine linker comprises $(Gly_4Ser)_3$.

IV. Intracellular Signaling Domain

The intracellular signaling domain comprises all or part of the CD3ζ chain. CD3ζ, also known as CD247, together with either the CD4 or CD8 T cell co-receptor is responsible for coupling extracellular antigen recognition to intracellular signaling cascades. In one embodiment, the CD3ζ used in any of the constructs provided herein is SEQ ID NO: 26.

In addition to the including of the CD3ζ signaling domain, the inclusion of co-stimulatory molecules has been shown to enhance CAR T-cell activity in murine models and clinical trials. Several have been investigated including CD28, 4-1BB, ICOS, CD27, CD270, CD30 and OX-40. The CAR of the current invention, in addition to including the KappaMab scFv, flexible linker, optimal hinge and CD3ζ chain also include one or more additional costimulatory domains from CD28, 4-1BB, ICOS, CD27, CD270, CD30 and/or OX-40, for example. These co-stimulatory domains are selected based on the desired functionality of the resulting CAR T-cell. Exemplary combinations are shown, for example, in FIGS. 6A-6C. In addition to altering the length of the extracellular hinge, the inclusion of particular combinations of costimulatory domains (e.g. CD28, OX-40, 4-1BB) also enhances the proliferation and survival of CAR T-cells in vivo. In one embodiment, the CD28 domain used in any of the constructs provided herein is SEQ ID NO: 25.

Co-Expression of Biologically Active Molecules

The CAR T-cells of the current invention have the added benefit, when compared to the use of the KappaMAb alone to be further modifiable to contain additional biologically active molecules to enhance the anti-tumor function and/or safety of the compositions. In one embodiment, the CAR T-cells may be further genetically modified to produce antitumor cytokines which allow for focused delivery to the tumor microenvironment/cancer cells, while avoiding systemic toxicity. Examples of additional biologically active molecules which may enhance the anti-tumor response of the CAR T-cells of the current invention include, without limitation, IL-12, the carbohydrate binding protein Galectin-3 (GAL3) or it's truncated form, GAL3C, and the cytokine receptor super antagonist SANT7. In another embodiment, CAR T-cells of the current invention may also be co-transduced with a plasmid that expresses a hepatocyte growth factor (HGF) binding protein. In one embodiment, the hepatocyte growth factor protein is an antibody or fragment thereof that is able to bind to and inhibit the function of HGF.

IL-12 is a potent tumor suppressor cytokine, decreasing tumor growth and angiogenesis and enhancing the tumor specific immune response. Multiple myeloma cells retain expression of the IL-12 receptor and administration of IL-12 to myeloma bearing mice decreases tumor progression as a single agent and acts synergistically with the proteasome inhibitor bortezomib (Airoldi, et al. (2008) Blood, 112(3): 750-759; Wang, et al. (2014) Anticancer Drugs, 25(3): 282-288). Expression of IL-12 by CAR T-cells dramatically enhances their ability to eradicate solid tumors but this approach has not yet been investigated in multiple myeloma (Pegram, (2012) Blood, 119(180:4133-4141 and Zhang, et al. (2011) Mol. Ther. 19(4):751-759).

SANT7 is a cytokine receptor super-antagonist. It is an analogue of IL-6 that has been genetically modified to enhance its binding to the IL-6 receptor α-subunit 70-fold, with virtually no interaction with the gp130 signaling subunit. SANT7 induces apoptosis in IL-6 dependent myeloma cell lines in-vitro, overcomes stroma mediated resistance to dexamethasone in in-vitro and murine model and combined with NFκB inhibitors, completely overcomes resistance to apoptosis. IL-6 is a cytokine which plays a role in the growth and survival of a variety of tumors including multiple myeloma, lung cancer, colorectal cancer, breast cancer and others. Binding of IL-6 to its receptor activates the JAK-STAT pathway, with subsequent phosphorylation of STAT3 which modulates expression of apoptosis related genes such as BCL-XL and p53, causing resistance to apoptosis. IL-6 also promotes down-regulation of the IL-12 receptor on myeloma cells, decreasing IL-12's tumor suppressive properties. (Airoldi, et al. (2008) *Blood*, 112(3):750-759). The IL-6 receptor is upregulated in myeloma and elevated systemic levels of IL-6 correlate with a poor prognosis. (Rawstron, et al. (2000) *Blood* 96(12) 3880-3886; Ludwig, et al. (1991) *Blood*, 77(12):2794-2795). Monoclonal antibodies to IL-6 have been developed for clinical use, however, although early clinical trials in myeloma showed measurable biological effects, the antibodies appeared to form complexes with circulating IL-6, leading to reduced clearance and potentially limiting their efficacy. (Bataille, et al. (1995) *Blood*, 86(2): 685-691). Recently, the chimeric IL-6 specific monoclonal antibody Siltuximab has been assessed in phase I and II clinical trials in relapsed and refractory multiple myeloma. There were no responses to Siltuximab alone, but hematological toxicity was common with more than half experiencing therapy related infections.

Galectin-3 is a carbohydrate binding protein which may play a role in tumour adhesion and invasion. A truncated form of Galectin-3, Gal3C, acts as a dominant negative form and can inhibit myeloma cell growth and invasion. A Gal3C construct for activation inducible secretion was designed based on John et al (2003) *Clin Cancer Res.*, 9(6):2374-83 and Mirandola et al. (2011) *PLoS One*, 6(7):e21811. This consists of the 143 amino acid carboxy terminal which retains its carbohydrate binding properties, but lacks the N-terminal amino acids required for ligand crosslinking. The construct also contains the CD8-alpha leader peptide to direct secretion and a 6× His tag for detection.

In certain embodiments, in addition to expression vectors containing the CAR construct described above, T cells are further modified with one or more expression vectors comprising IL-12, SANT7 and/or GAL3C. Specifically, expression constructs expressing a single chain IL-12 comprising the IL-12 p35 subunit linked to the IL-12 p40 subunit are particularly useful in that the resulting protein is a fully bioactive IL-12 p70 heterodimer, however, expressed as a single polypeptide. In one embodiment, the single chain IL-12 construct, termed Flexi-12, is described, for example in Anderson, et al. (1997) Hum. Gene Ther. 8(9):1125-35 is used. The IL-12 single chain construct may be expressed in the same expression vector as the CAR construct or it may expressed in a separate expression vector and co-transduced into the T cell. Similarly, T cells transduced with the CAR construct described above, may be co-transduced with an additional expression vector comprising SANT7 and/or GAL3C, alternatively, one expression vector may be used to transduce T cells with both of SANT7 and GAL3C either alone or in combination and the CAR construct described above. In another embodiment three expression vectors may be used, one expressing the CAR construct, one expressing the single chain IL-12 construct and one expressing the SANT7 construct. A similar strategy may be used to co-express GAL3C with IL-12 and/or SANT7. Alternatively, the IL-12, GAL3C and/or SANT7 construct may be expressed via a single expression vector while the CAR construct is expressed by its own expression vector. One of skill in the art will appreciate the different combinations and possibilities for expressing these molecules in the same T cell.

HGF Binding Protein

Hepatocyte growth factor (HGF) and its receptor, MET have been implicated in cancer development and progression, in particular in tumor invasion and progression to metastatic disease. Multiple myeloma cells express both HGF and MET, thus creating both an autocrine and paracrine loop whereas normal plasma cells do not express HGF (Zhan et al. (2002); Borset, et al. (1996). Furthermore, HGF concentrations are significantly increased in the blood and bone marrow of plasma patients with multiple myeloma and high serum HGF levels correlate with advanced stage disease and extensive bone lesions (Seidel et al. (1998); Wader, et al. (2008); Alexandrakis, et al. (2003). Furthermore, serum biomarker analysis of patients in a phase I trial with KappaMab shows statistically significant dose related decrease in serum HGF after treatment with KappaMab compared to control. In order to enhance this reduction in serum HGF, in certain embodiments an HGF binding protein will be expressed in the CAR T-cells of the current invention. In a particular embodiment, the HGF binding protein expressed is an antibody or fragment thereof. In a particular embodiment, the anti-HGF binding protein is an antibody, a diabody, a scFv or an Fab. In one embodiment, the HGF binding protein is expressed in the same expression vector as the CAR construct. In a further embodiment, the HGF binding protein is expressed in a separate expression vector but is co-transduced with the CAR construct. In still a further embodiment, the CAR-T cell expresses the CAR, an HGF binding protein and IL-12. In still a further embodiment, the CAR-T cell expresses the CAR, an HGF binding protein and SANT7. In still a further embodiment, the CAR-T cell expresses the CAR, an HGF binding protein and GAL3C. In still a further embodiment, the CAR-T cell expresses the CAR, an HGF binding protein and IL-12 and GAL3C. In still a further embodiment, the CAR-T cell expresses the CAR, an HGF binding protein and SANT7 and GAL3C. In still another embodiment, the CAR-T cell expresses the CAR, an anti-HGF binding protein, IL-12 and SANT7. In still a further embodiment, the CAR-T cell expresses the CAR, an HGF binding protein, IL-12, SANT7 and GAL3C.

Methods of Producing the CAR T-Cells of the Present Invention

In one aspect, methods are provided for generating CAR T-cells expressing the CAR(s) described herein and optionally one or more anti-tumoral cytokine (e.g. IL-12 and/or SANT7) and/or one or more HGF binding protein. One of skill in the art will readily understand that while preferred methods of constructing expression vectors containing the CARs and anti-tumoral cytokines/antibodies of the present invention are described herein, that any methods which are able to transduce T cells to express these constituents may be used.

In one embodiment, T cells are obtained from the blood of a subject by venous puncture, aspiration of bone marrow, steady state leukapheresis or cytokine primed leukapheresis and subsequent isolation of peripheral blood mononuclear cells including T cells using density gradient separation. In certain embodiments, after lysing red blood cells, T cells are sorted by flow cytometry or purified using antibodies to antigens expressed on T cells and magnetic beads to obtain a population of pure T cells. In a particular embodiment, T cells are sorted based on their expression of CD3 to obtain a whole T cell fraction. In another embodiment T cells are sorted based on their expression of CD4 or CD8 to obtain a population of either CD4$^+$ T cells or CD8$^+$ T cells. In a particular embodiment, T cells are obtained from the subject in need of CAR T-cell therapy. In another embodiment, T cells are obtained from a donor subject who is not the intended recipient of CAR T-cell therapy.

In one embodiment, separated T cells are cultured in vivo under conditions suitable for their survival and are transduced with expression vectors containing the sequences necessary for expression of the CARs described herein and/or IL-12, SANT7, GAL3C and/or an HGF binding protein. In one embodiment, the expression vector is a transposable vector expression system. In a particular embodiment, the expression vector is a PiggyBac transposon expression plasmid or a viral vector (e.g. retroviral vector or lentiviral vector). In one embodiment, the PiggyBac transposon expression plasmid is inducible such as, for example, the PiggyBac transposon plasmid described in the Examples provided herein. In one embodiment, the PiggyBac transposon expression plasmid comprises a constitutively active promoter and/or an activation inducible promoter. The constitutively active promoter can be an elongation factor 1 alpha (EF1alpha) promoter. The activation inducible promoter can be a (NFAT pro) promoter. In one aspect, a PiggyBac expression plasmid is used and produces permanent integration of the CAR by cutting and pasting the CAR, IL-12, SANT-7, GAL3C and/or HGF binding protein coding sequences into the T cell's genome. In a particular embodiment, the expression vectors of the current invention further comprise a detectable marker which allows for identification of T cells that have been successfully transduced with the one or more expression vectors. In one embodiment, the detectable marker is chosen from the group consisting of a cell surface marker such as CD34 or CD20 or another surface protein, a fluorophore such as fluorescein isothiocyanate or any other fluorescent dye that emits light when excited to a higher energy state including by a laser, and an antibiotic resistance cassette such as kanamycin resistance, ampicillin resistance or any other cassette that confers resistance to an antibiotic substance contained in medium in which transduced T cells are to be cultured. In one embodiment, the detectable marker is a green fluorescence protein (GFP). The GFP can be an enhanced GFP, such as, for example, the constructs shown in the Examples provided herein. In a particular embodiment, each expression vector used (e.g. one expression vector comprising a CAR, and one comprising an IL-12, GAL3C and/or SANT-7 and one comprising an HGF binding protein) comprises a unique detectable marker. In one embodiment, the expression vectors are transduced into the T cell by a method suitable for the expression vector(s) selected. In one embodiment, the PiggyBac expression vector is transduced into T cells by electroporation.

After introduction of the appropriate expression vectors, T cells may be cultured and expanded in vitro by co-culture with autologous peripheral blood mononuclear cells (PBMCs) and the appropriate growth factors and further screened for the presence of the one or more detectable markers. T cells expressing the appropriate detectable markers for the expression vectors chosen may then be sorted and purified for use in the methods of the current invention.

Methods of Treating KMA-Expressing Malignancies

In one aspect, methods are provided for treating subjects in need thereof with the CAR T-cells provided herein. In a particular aspect, the subject in need thereof is a human subject who has been diagnosed with or is suspected of having a malignancy that expresses KMA, for example a B cell malignancy expressing KMA. In certain embodiments, a patient has or is suspected of having multiple myeloma (MM), Waldenstroms macroglobulinemia, diffuse large B cell lymphoma (DLBCL), or amyloidosis. Methods for diagnosing B cell malignancies expressing KMA, for example, multiple myeloma (MINI) Waldenstroms macroglobulinemia, diffuse large B cell lymphoma (DLBCL), and amyloidosis are known in the art, and as such are not described in detail herein. The CAR T-cells may be used alone or in combination with other therapeutically effective agents for the treatment of multiple myeloma (MM) Waldenstroms macroglobulinemia, diffuse large B cell lymphoma (DLBCL), amyloidosis or another B cell malignancy expressing KMA. In certain aspects, the CAR T-cells of the current invention are administered in a pharmaceutical formulation suitable for intravenous delivery.

In certain aspects, the CAR T-cells of the current invention are administered before, during or after one or more immunomodulatory drugs. In a particular aspect, the one or more immunomodulatory drugs is thalidomide or a thalidomide analog such as, for example, lenolidomide or pomalidomide.

In certain aspects of the invention, the CAR T-cells of the current invention act synergistically when administered with one or more immunomodulatory drugs.

In a further embodiment, the CAR T-cells of the current invention are administered before, during or after treatment with one or more histone deacetylase inhibitors such as panobinostat, vorinostat, trichostatin A, depsipeptides, phenylbutyrate, valproic acid, belinostat, LAQ824, entinostat, CI944 or mocetinostat.

In certain aspects of the invention, the CAR T-cells of the current invention act synergistically when administered in combination with one or more histone deacetylase inhibitors.

In certain aspects of the invention, the CAR T-cells of the current invention act synergistically when administered in combination with intermediate or high dose chemotherapy and following administration of autologous or allogenic human blood stem cells.

In one embodiment, the CAR T-cells of the current invention are administered before, during or after an allogenic stem cell transplant. In still another embodiment, the CAR T-cells of the current invention are administered before during or after an allogenic stem cell transplant. Without being bound by theory, the CAR T-cells of the present invention, when administered in combination with an autologous or allogeneic stem cell transplant prevent the appearance of minimal residual disease that may occur by incomplete ablation of the bone marrow prior to stem cell transplant or by reemergence of malignant B cell clones expressing KMA.

All patents, patent applications, and publications cited herein are expressly incorporated by reference in their entirety for all purposes.

EXAMPLES

The invention is further described in detail by reference to the following experimental examples. These examples are provided for the purposes of illustration only and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can using the preceding description and following examples, make and utilize the compounds of the present invention and practice the claimed methods. The following working examples, therefore, specifically point out the preferred embodiments of the present invention and are not to be construed as limiting in any way the remainder of the disclosure.

Example 1

Generation of KMA.CAR-28z

Figures 6A, 6B, 6C:
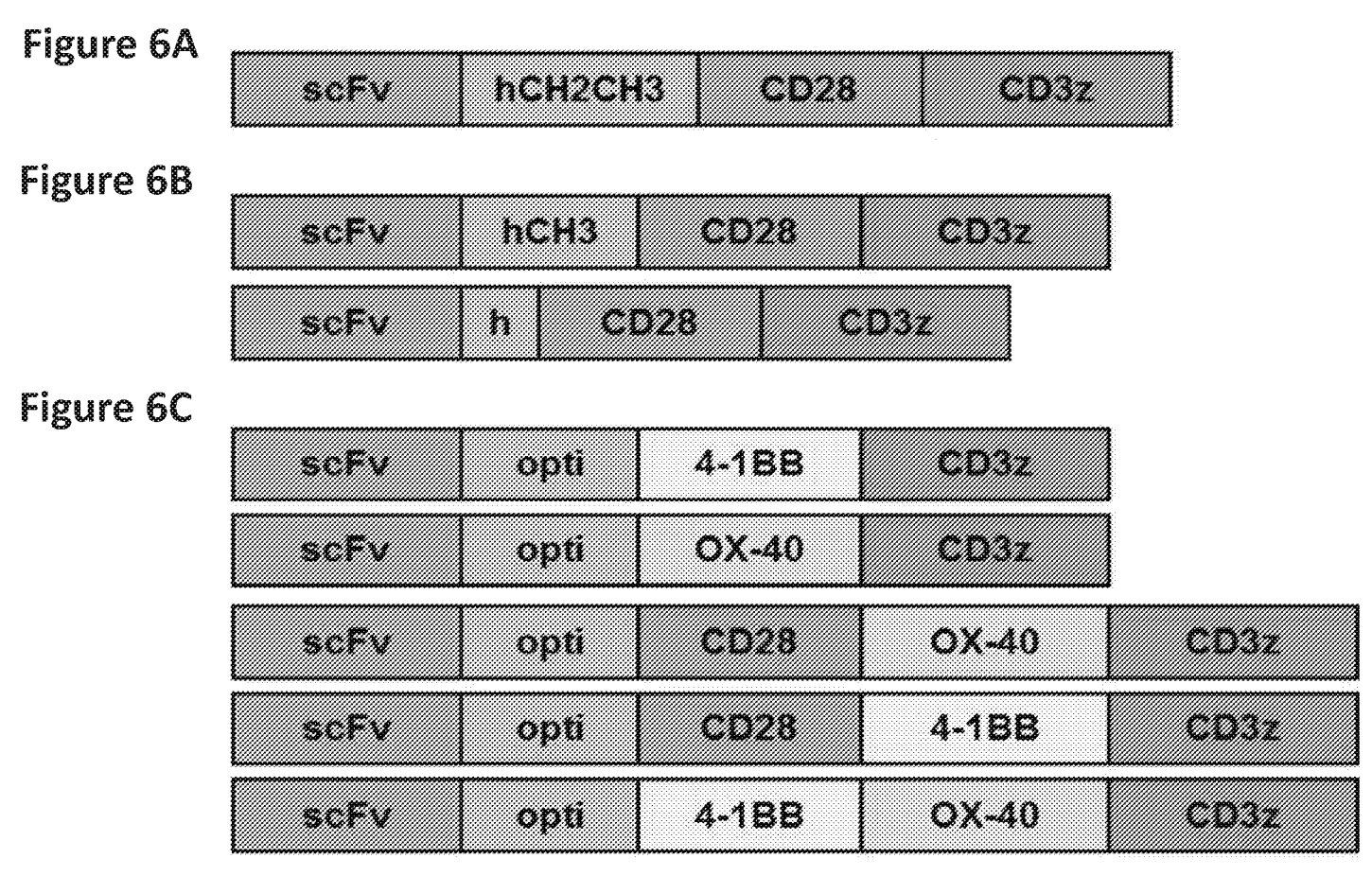

Based on the nucleotide sequence coding for the variable regions of KappaMab (SEQ ID NOS: 9 and 10), a scFv was designed and cloned into a CAR construct containing an immunoglobulin heavy chain hinge, a CD28 co-stimulatory domain and the CD3-zeta endodomain (FIG. 6A). The construct was designed in Clone Manage 9 (Sci-Ed Software) using the genetic sequence of the antibody variable regions provided byHaemalogix Pty Ltd. The amino acid sequence from 5' to 3' of portions of this construct(i.e., KM.CAR-hCH2CH3-28z; FIG. 6A) are as follows:

The Ig heavy chain leader peptide (Uniprot P01764) is
(SEQ ID NO: 20)
MEFGLSWLFLVAILKGVQCSR.

The KappaMab antibody light chain variable region is
(SEQ ID NO: 21)
DIVMTQSQKFMSTSVGDRVSVTCKASQNVGTNVAWYQQKPGQSPKALIYS
TSYRYSGVPDRFTGSGSGTDFTLTISNVQSEDLAEYFCQQYNSYPYTFGG
GTKLEIK.

The heavy chain variable region is
(SEQ ID NO: 22)
EVQLQQSGAELVKPGASVKLSCTASGFNIKDTYMHWVKQRPEQGLEWIGR
IDPANGNTKYDPKFQGKATIIADTSSNTAYLQLSSLTSEDTAVYYCARGV
YHDYDGDYWGQGTTLTVSSYVTVSS.

The (G$_4$S)$_3$ flexible linker is
(SEQ ID NO: 23)
GGGGSGGGGSGGGGS.

The hinge, CH2 and CH3 domains of IgG1 constant region with a C > P mutation in the hinge region at amino acid position 103 (Uniprot P01857) is
(SEQ ID NO: 24)
YVTVSSQDPAEPKSPDKTHTCPPCPAPELLGGPSVFLFPPKPKDTLMISR
TPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFF
LYSKLTVDKSRWQQGNVFSCSVMHEALHNHYTQKSLSLSPGKKDPK.

The transmembrane and intracellular domains of CD28 (Uniprot P10747) is
(SEQ ID NO: 25)
FWVLVVVGGVLACYSLLVTVAFIIFWVRSKRSRLLHSDYMNMTPRRPGPT
RKHYQPYAPPRDFAAYRS.

The intracellular domain of human CD3 zeta (Uniprot P20963) is
(SEQ ID NO: 26)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR.

The full length amino acid sequence as follows is
(SEQ ID NO: 27)
MEFGLSWLFLVAILKGVQCSRDIVMTQSQKFMSTSVGDRVSVTCKASQNV
GTNVAWYQQKPGQSPKALIYSTSYRYSGVPDRFTGSGSGTDFTLTISNVQ
SEDLAEYFCQQYNSYPYTFGGGTKLEIKGGGGSGGGGSGGGGSEVQLQQS
GAELVKPGASVKLSCTASGFNIKDTYMHWVKQRPEQGLEWIGRIDPANGN
TKYDPKFQGKATIIADTSSNTAYLQLSLTSEDTAVYYCARGVYHDYDGDY
WGQGTTLTVSSYVTVSSQDPAEPKSPDKTHTCPPCPAPELLGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTT
PPVLDSDGSFFLYSKLTVDKSRWQQGNVFScSVMHEALHNHYTQKSLSLS
PGKKDPKFWVLVVVGGVLACYSLLVTVAFIIFWVRSKRSRLLHSDYMNMT
PRRPGPTRKHYQPYAPPRDFAAYRSRVKFSRSADAPAYQQGQNQLYNELN
LGRREEYDVLDKRRGRDPEMGGKPRRKNPQEGLYNELQKDKMAEAYSEIG
MKGERRRGKGHDGLYQGLSTATKDTYDALHMQALPPR.

This amino acid sequence (SEQ ID NO: 27) is encoded by the following DNA sequence:

(SEQ ID NO: 28)
ATGGAGTTTGGGCTGAGCTGGCTTTTTCTTGTGGCTATTTTAAAAGGTGT
CCAGTGCTCTAGAGACATCGTCATGACCCAGTCTCAAAAATTCATGTCCA
CATCAGTAGGAGACAGGGTCAGCGTCACCTGCAAGGCCAGTCAGAATGTG
GGTACTAATGTAGCCTGGTATCAACAGAAACCAGGGCAATCTCCTAAAGC
ACTGATTTACTCGACATCCTACCGGTACAGTGGAGTCCCTGATCGCTTCA
CAGGCAGTGGATCTGGGACAGATTTCACTCTCACCATCAGCAATGTGCAG
TCTGAAGACTTGGCAGAGTATTTCTGTCAGCAATATAACAGCTATCCGTA

-continued

```
CACGTTCGGAGGGGGGACCAAGCTGGAAATAAAGGGTGGCGGTGGCTCGG

GCGGTGGTGGGTCGGGTGGCGGCGGATCTGAGGTGCAGCTGCAGCAGTCA

GGGGCGGAGCTTGTGAAGCCAGGGGCCTCAGTCAAGTTGTCCTGTACAGC

TTCTGGCTTCAACATTAAAGACACCTATATGCACTGGGTGAAGCAGAGGC

CTGAACAGGGCCTGGAGTGGATTGGAAGGATTGATCCTGCGAATGGTAAC

ACTAAATATGACCCGAAGTTCCAGGGCAAGGCCACTATAATAGCAGACAC

ATCCTCCAACACAGCCTACCTGCAGCTCAGCAGCCTGACATCTGAGGACA

CTGCCGTCTATTACTGTGCTAGGGGGGTCTACCATGATTACGACGGGGAC

TACTGGGGCCAAGGGACCACGCTCACCGTCTCCTCCTACGTCACCGTCTC

TTCACAGGATCCCGCCGAGCCCAAATCTCCTGACAAAACTCACACATGCC

CACCGTGCCCAGCACCTGAACTCCTGGGGGACCGTCAGTCTTCCTCTTC

CCCCCAAAACCCAAGGACACCCTCATGATCTCCCGGACCCCTGAGGTCAC

ATGCGTGGTGGTGGACGTGAGCCACGAAGACCCTGAGGTCAAGTTCAACT

GGTACGTGGACGGCGTGGAGGTGCATAATGCCAAGACAAAGCCGCGGGAG

GAGCAGTACAACAGCACGTACCGTGTGGTCAGCGTCCTCACCGTCCTGCA

CCAGGACTGGCTGAATGGCAAGGAGTACAAGTGCAAGGTCTCCAACAAAG

CCCTCCCAGCCCCCATCGAGAAAACCATCTCCAAAGCCAAAGGGCAGCCC

CGAGAACCACAGGTGTACACCCTGCCCCCATCCCGGGATGAGCTGACCAA

GAACCAGGTCAGCCTGACCTGCCTGGTCAAAGGCTTCTATCCCAGCGACA

TCGCCGTGGAGTGGGAGAGCAATGGGCAACCGGAGAACAACTACAAGACC

ACGCCTCCCGTGCTGGACTCCGACGGCTCCTTCTTCCTCTACAGCAAGCT

CACCGTGGACAAGAGCAGGTGGCAGCAGGGGAACGTCTTCTCATGCTCCG

TGATGCATGAGGCTCTGCACAACCACTACACGCAGAAGAGCCTCTCCCTG

TCTCCGGGTAAAAAAGATCCCAAATTTTGGGTGCTGGTGGTGGTTGGTGG

AGTCCTGGCTTGCTATAGCTTGCTAGTAACAGTGGCCTTTATTATTTTCT

GGGTGAGGAGTAAGAGGAGCAGGCTCCTGCACAGTGACTACATGAACATG

ACTCCCCGCCGCCCCGGGCCCACCCGCAAGCATTACCAGCCCTATGCCCC

ACCACGCGACTTCGCAGCCTATCGCTCCAGAGTGAAGTTCAGCAGGAGCG

CAGACGCCCCGCGTACCAGCAGGGCCAGAACCAGCTCTATAACGAGCTC

AATCTAGGACGAAGAGAGGAGTACGATGTTTTGGACAAGAGACGTGGCCG

GGACCCTGAGATGGGGGGAAAGCCGAGAAGGAAGAACCCTCAGGAAGGCC

TGTACAATGAACTGCAGAAAGATAAGATGGCGGAGGCCTACAGTGAGATT

GGGATGAAAGGCGAGCGCCGGAGGGGCAAGGGGCACGATGGCCTTTACCA

GGGTCTCAGTACAGCCACCAAGGACACCTACGACGCCCTTCACATGCAGG

CCCTGCCCCCTCGC.
```

In terms of constructing this construct, a gene sequence consisting of a 5' EcoRI restriction enzyme site, a 5' Kozak sequence, Leader Peptide, single chain variable fragment and a portion of the IgG1 constant region incorporating an AleI restriction enzyme site, was synthesised by GeneArt (ThermoFisher Scientific), sequence verified and then cloned into the pIRII-CAR.CD19-28z PiggyBac transposon expression plasmid. This was then introduced into donor T-cells from 2 normal donors by co-electroporation with the PiggyBac Transposase plasmid to mediate stable integration. The PiggyBac transposon/transposase system produces permanent integration of the CAR by cutting and pasting the gene of interest into the target cell genome. The PiggyBac expression system was chosen because it is capable of producing high levels of permanent genetic modification at a fraction of the cost of retroviral vectors. However, one of skill in the art will understand that other expression systems, including retroviral vectors could also be used in accordance with the current invention.

Figure 4A:
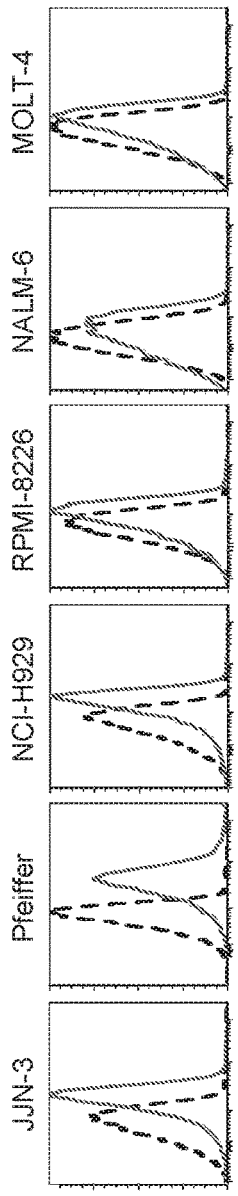
FIGS. 4A-4C shows KMA.CAR-28z function.

The KM.CAR-hCH2CH3-28z expressing T-cells were expanded according to our optimised protocols by co-culturing with autologous peripheral blood mononuclear (PBMC) feeder cells supplemented with interleukin-15 (IL-15) 10 ng/ml. After culturing for 3 weeks with replacement of PBMCs on a weekly basis and replenishment of IL-15 two to three times per week, T-cells were harvested and assessed for phenotype and CAR expression by flow cytometry, KMA-specific function by interferon gamma intracellular cytokine flow cytometry on stimulation with KMA+ and KMA− cell lines (FIG. 4A) and cytotoxicity of the same cell lines in a chromium release assay.

Figure 4B:
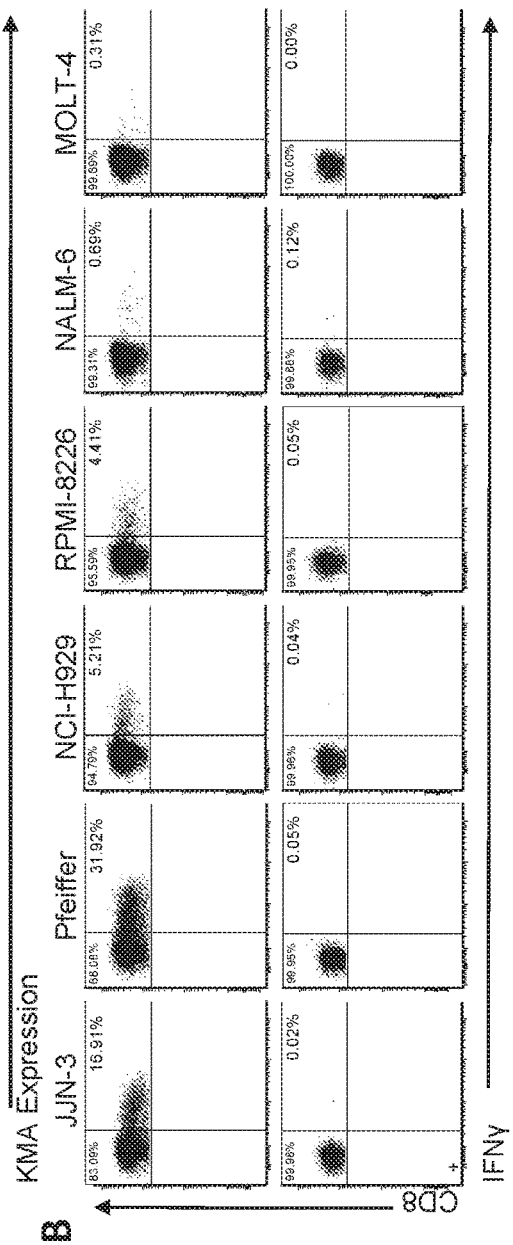
Figure 4C:
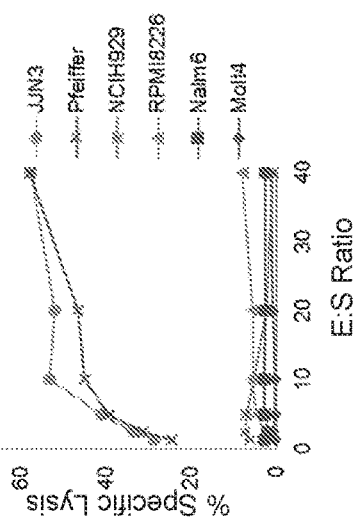

At the end of 3 weeks, the cultures were predominantly CAR expressing CD3$^+$ T-cells (55% and 70% of live cells), expressed interferon-gamma in response to KMA$^+$ myeloma and B-cell lines (FIG. 4B) and demonstrated KMA-specific cytotoxicity (FIG. 4C).

Example 2

Establishing a Human Myeloma Xenograft Murine Model

Figure 5A:
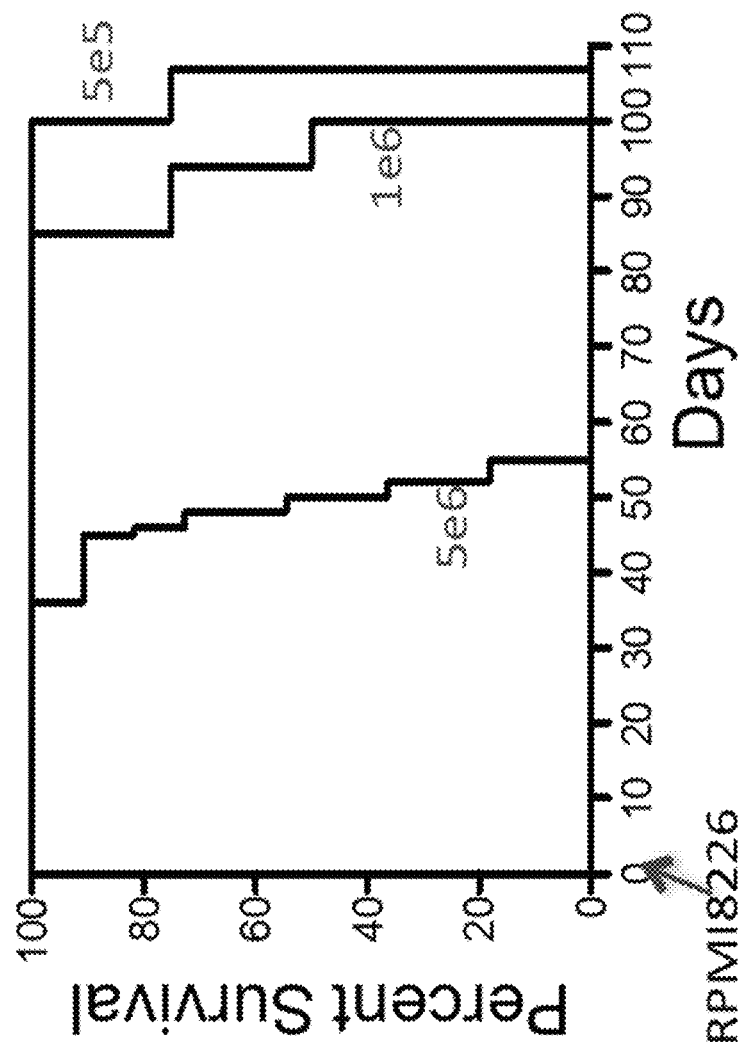
FIG. 5A shows RPMI-Rag mice injected with 5×10$^5$–5×10$^6$ myeloma cells
Figure 5B:
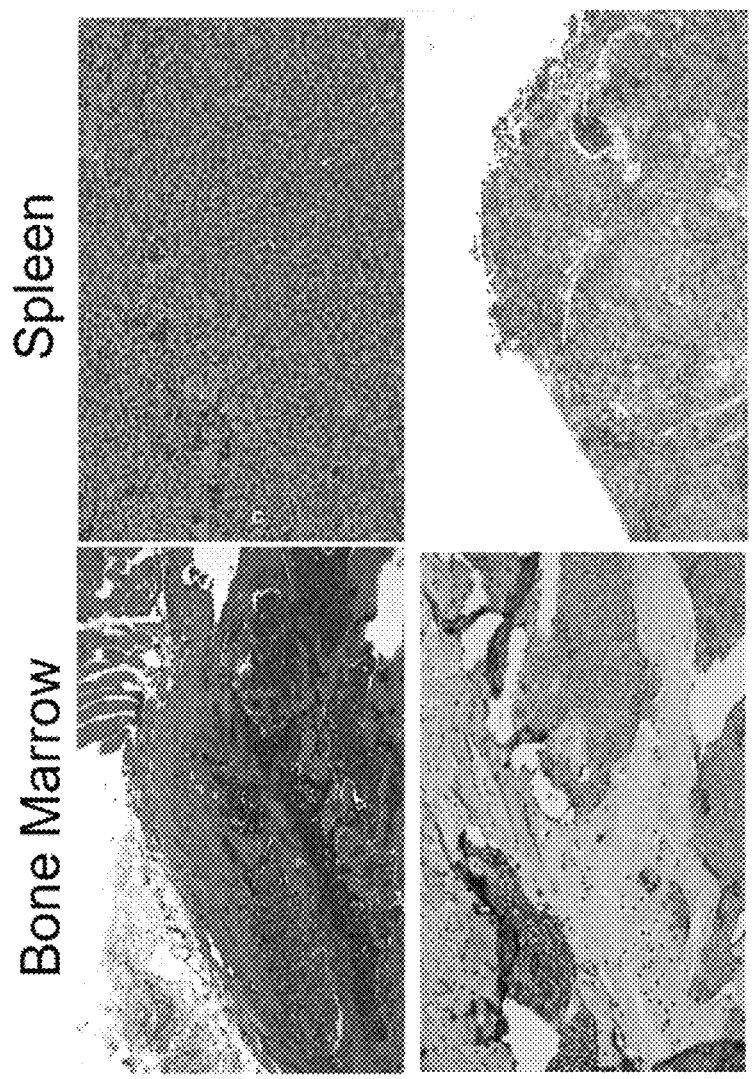
FIG. 5B shows infiltration of the bone marrow and spleen with CD138$^+$ RPMI9226 cells
Figure 5C:
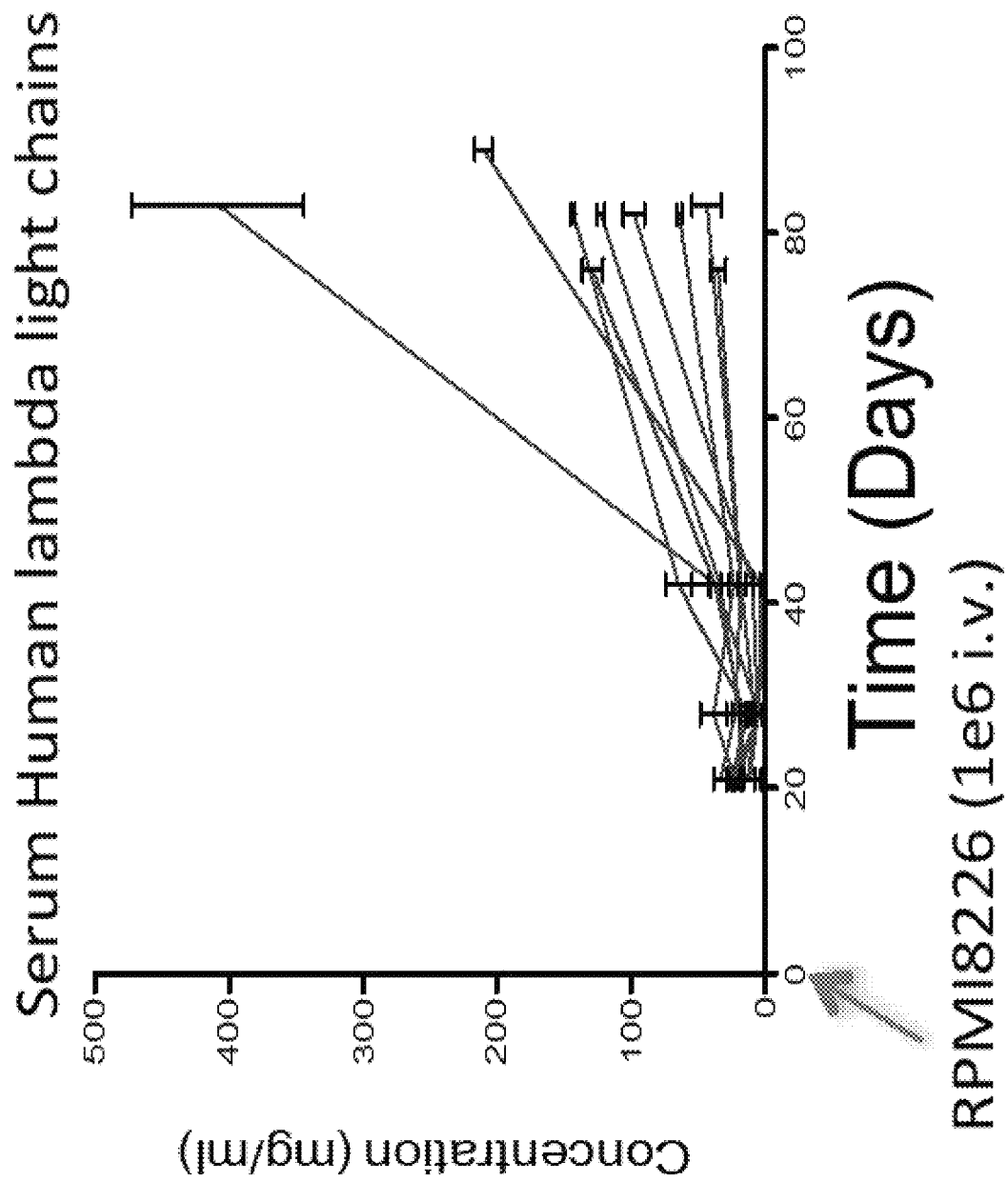
FIG. 5C shows elevated levels of serum human lambda light chain on progressive disease
Figure 5D:
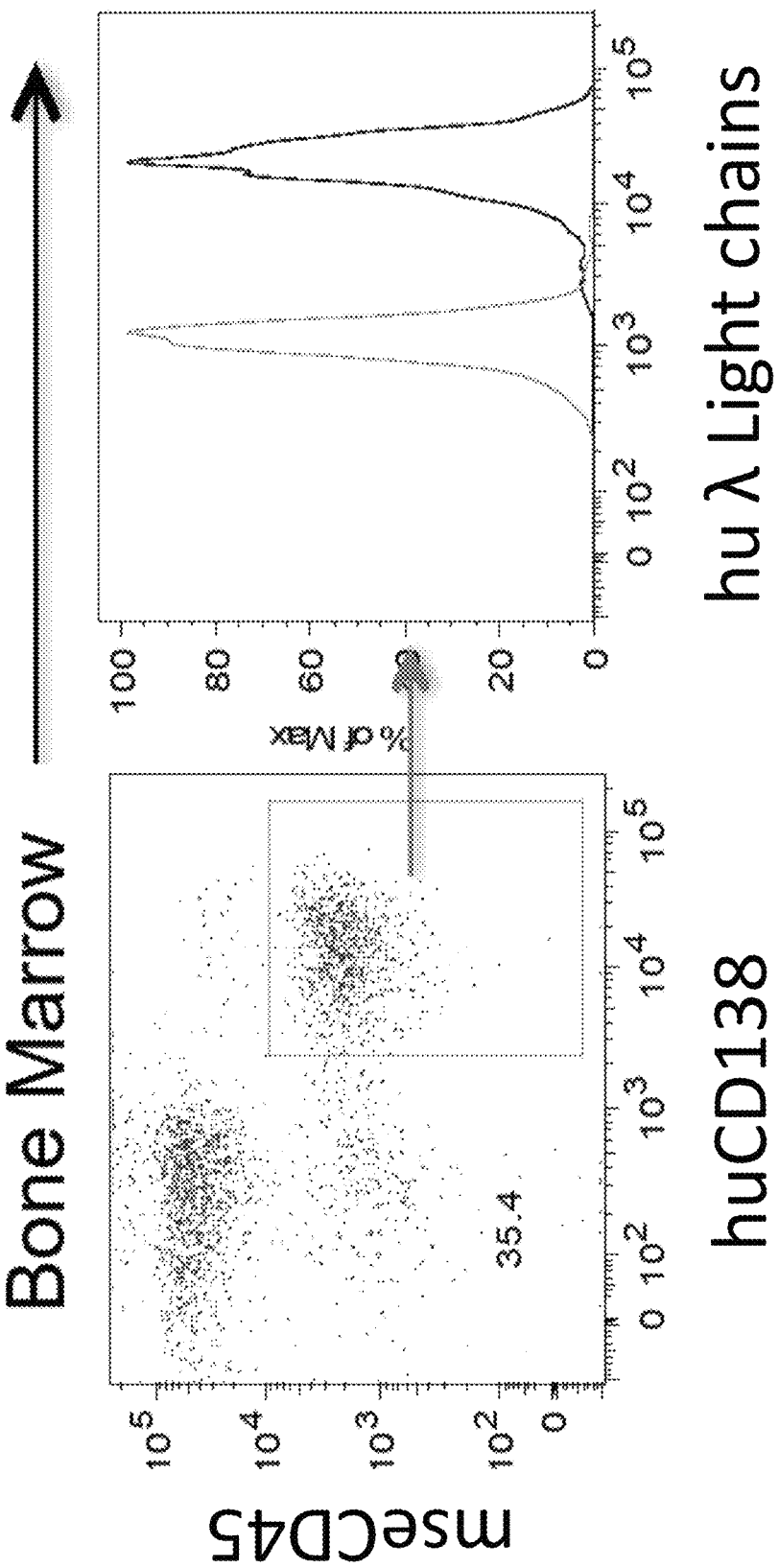
FIG. 5D shows CD138$^+$/cytoplasmic lambda light chain positive cells in the bone marrow
Figure 5E:
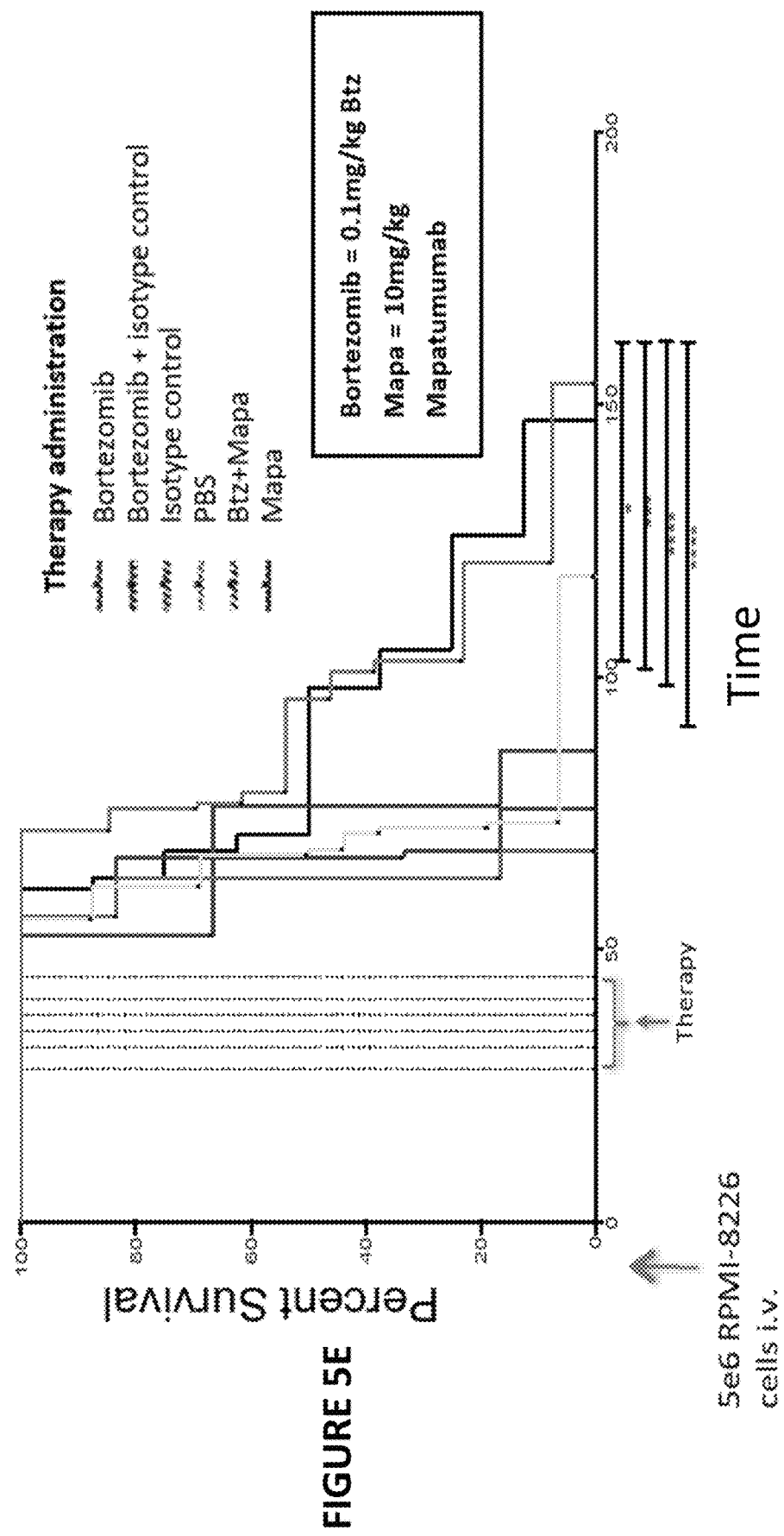
FIG. 5E shows RPMI-Rag mice as a therapeutic model.

A human myeloma to mouse xenotransplant model of multiple myeloma was established. RPMI8226 or alternative myeloma cell lines were inoculated i.v. into Rag2−/− γc−/− (BALB/c) mice to form the Rag MM model (FIGS. 5A-5D). The Rag2−/−γc−/− (BALB/c) mice lack mouse lymphocytes (T, B and NK cells) and are receptive hosts for human xenograft studies. This model has been used successfully to test novel therapeutics such as bortezomib in combination with a novel antibody (FIG. 5E). We will use this MINI model to test and further optimize the KMA.CAR T cells.

Example 3

Optimized KMA.CAR Constructs

Based on the construct described in Example 1, 6 CAR constructs containing the KM scFv described in Example 1 with variable length spacer regions and co-stimulatory endodomains (e.g., CD28 or 4-1BB (CD137-Uniport Q07011)) with the CD3 zeta endodomain were constructed (FIG. 2 & FIGS. 6B-6D). Varying the spacer length altered the distance between the T-cell and the target cell with a shorter spacer potentially enhancing target cell lysis. In all constructs, the CD28 transmembrane domain was used to ensure stable T-cell surface expression of the KMA.CARs. In all cases where components of the IgG1 heavy chain constant region was used as a spacer, a second (G4S)$_3$ flexible linker was placed between the scFv and the spacer region. These CARs were synthesised commercially by genscript and cloned into a pVAX1PB PiggyBac transposon plasmid for further testing.

3 of the 6 KM.CAR constructs contained aCD28 Costimulatory Endodomain and were as follows:

The first construct of this group was the KM.CAR_hCH3 28z construct, which contains only the hinge and CH3 domains of IgG1 heavy chain constant region as the spacer and whose nucleic acid sequence is as follows:

(SEQ ID NO: 29)
ATGGAGTTTGGGCTGAGCTGGCTTTTTCTTGTGGCTATTTTAAAAGGTGT

CCAGTGCTCTAGA GACATCGTCATGACCCAGTCTCAAAAATTCATGTCCA

CATCAGTAGGAGACAGGGTCAGCGTCACCTGCAAGGCCAGTCAGAATGTG

GGTACTAATGTAGCCTGGTATCAACAGAAACCAGGGCAATCTCCTAAAGC

ACTGATTTACTCGACATCCTACCGGTACAGTGGAGTCCCTGATCGCTTCA

CAGGCAGTGGATCTGGGACAGATTTCACTCTCACCATCAGCAATGTGCAG

TCTGAAGACTTGGCAGAGTATTTCTGTCAGCAATATAACAGCTATCCGTA

CACGTTCGGAGGGGGGACCAAGCTGGAAATAAAG GGTGGCGGTGGCTCGG

GCGGTGGTGGGTCGGGTGGCGGCGGATCT GAGGTGCAGCTGCAGCAGTCA

GGGGCGGAGCTTGTGAAGCCAGGGGCCTCAGTCAAGTTGTCCTGTACAGC

TTCTGGCTTCAACATTAAAGACACCTATATGCACTGGGTGAAGCAGAGGC

CTGAACAGGGCCTGGAGTGGATTGGAAGGATTGATCCTGCGAATGGTAAC

ACTAAATATGACCCGAAGTTCCAGGGCAAGGCCACTATAATAGCAGACAC

ATCCTCCAACACAGCCTACCTGCAGCTCAGCAGCCTGACATCTGAGGACA

CTGCCGTCTATTACTGTGCTAGGGGGGTCTACCATGATTACGACGGGGAC

TACTGGGGCCAAGGGACCACGCTCACCGTCTCCTCC GGTGGAGGCGGGTC

TGGGGGCGGAGGTTCAGGCGGGGGTGGTTCC GAGCCCAAATCTCCTGACA

AAACTCACACATGCCCAGGGCAGCCCCGAGAACCACAGGTGTACACCCTG

CCCCCATCCCGGGATGAGCTGACCAAGAACCAGGTCAGCCTGACCTGCCT

GGTCAAAGGCTTCTATCCCAGCGACATCGCCGTGGAGTGGGAGAGCAATG

GGCAGCCGGAGAACAACTACAAGACCACGCCTCCCGTGCTGGACTCCGAC

GGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACC

ACTACACACAGAAGAGCCTCTCCCTGTCTCCGGGTAAA TTTTGGGTGCT

GGTGGTGGTTGGTGGAGTCCTGGCTTGCTATAGCTTGCT

AGTAACAGTGGCCTTTATTTATTTTCTGGGTGAGGAGT

AAGAGGAGCAGGCTCCTGCACAGTGACTACATGAACA

TGACTCCCGCCGCCCCGGCCCACCCGCAAGCATTA

CCAGCCCTATGCCCACCACGCGACTTCGCAGCCTA

TCGCTCC AGAGTGAAGTTCAGCAGGAG

CGCAGACGCCCCGCGTACCAGCAGGGCCAGAACCAGCTCTATAACGAG

CTCAATCTAGGACGAAGAGAGGAGTACGATGTTTTGGACAAGAGACGTG

GCCGGGACCCTGAGATGGGGGAAAGCCGAGAAGGAAGAACCCTCAGGA

AGGCCTGTACAATGAACTGCAGAAAGATAAGATGGCGGAGGCCTACAGT

GAGATTGGGATGAAAGGCGAGCGCCGGAGGGGCAAGGGGCACGATGGCC

TTTACCAGGGTCTCAGTACAGCCACCAAGGACACCTACGACGCCCTTCA

CATGCAGGCCCTGCCCCCTCGC.

From 5' to 3', this construct (SEQ ID NO: 29) has a leader peptide, a KappaMab light chain variable region, a (G4S)₃ linker, a KappaMab heavy chain variable region, a second (G4S)₃ linker, an IgG1 hinge & CH3 constant region domains, a CD28 transmembrane and intracellular domains, and a CD3 zeta intracellular domain. A diagram of this construct is shown in FIG. 6B.

The second construct of this group is the KM.CAR_h_28z construct, which contains only the hinge domain of IgG1 heavy chain constant region as the spacer, and whose nucleic acid sequence is as follows:

(SEQ ID NO: 30)
ATGGAGTTTGGGCTGAGCTGGCTTTTTCTTGTGGCTATTTTAAAAGGTGT

CCAGTGCTCTAGA GACATCGTCATGACCCAGTCTCAAAAATTCATGTCCA

CATCAGTAGGAGACAGGGTCAGCGTCACCTGCAAGGCCAGTCAGAATGTG

GGTACTAATGTAGCCTGGTATCAACAGAAACCAGGGCAATCTCCTAAAGC

ACTGATTTACTCGACATCCTACCGGTACAGTGGAGTCCCTGATCGCTTCA

CAGGCAGTGGATCTGGGACAGATTTCACTCTCACCATCAGCAATGTGCAG

TCTGAAGACTTGGCAGAGTATTTCTGTCAGCAATATAACAGCTATCCGTA

CACGTTCGGAGGGGGGACCAAGCTGGAAATAAAG GGTGGCGGTGGCTCGG

GCGGTGGTGGGTCGGGTGGCGGCGGATCT GAGGTGCAGCTGCAGCAGTCA

GGGGCGGAGCTTGTGAAGCCAGGGGCCTCAGTCAAGTTGTCCTGTACAGC

TTCTGGCTTCAACATTAAAGACACCTATATGCACTGGGTGAAGCAGAGGC

CTGAACAGGGCCTGGAGTGGATTGGAAGGATTGATCCTGCGAATGGTAAC

ACTAAATATGACCCGAAGTTCCAGGGCAAGGCCACTATAATAGCAGACAC

ATCCTCCAACACAGCCTACCTGCAGCTCAGCAGCCTGACATCTGAGGACA

CTGCCGTCTATTACTGTGCTAGGGGGGTCTACCATGATTACGACGGGGAC

TACTGGGGCCAAGGGACCACGCTCACCGTCTCCTCC GGTGGAGGCGGGTC

TGGGGGCGGAGGTTCAGGCGGGGGTGGTTCC GAGCCCAAATCTCCTGACA

AAACTCACACATGCC CATTTTGGGTGCTGGTGGTGG

TTGGTGGAGTCCTGGCTTGCTATAGCTTGCTAGTAAC

AGTGGCCTTTATTATTTTCTGGGTGAGGAGTAAGAGGAG

CAGGCTCCTGCACAGTGACTACATGAACGCCGCCCCG

CATGACTCCCGGCCCACCCGCAAGCATTACCAGCCC

TATGCCCCACCACGCGACTTCGCAGCCTATCGCTCC AGAGTGAAGT

TCAGCAGGAGCGCAGACGCCCCCGCGTACCAGCAGGGCCAGAACCAGCT

CTATAACGAGCTCAATCTAGGACGAAGAGAGGAGTACGATGTTTTGGAC

AAGAGACGTGGCCGGGACCCTGAGATGGGGGAAAGCCGAGAAGGAAGA

ACCCTCAGGAAGGCCTGTACAATGAACTGCAGAAAGATAAGATGGCGGA

GGCCTACAGTGAGATTGGGATGAAAGGCGAGCGCCGGAGGGGCAAGGGG

CACGATGGCCTTTACCAGGGTCTCAGTACAGCCACCAAGGACACCTACG

ACGCCCTTCACATGCAGGCCCTGCCCCCTCGC.

From 5' to 3', this construct (SEQ ID NO: 30) has a leader peptide, a KappaMab light chain variable region, a (G4S)₃ linker, a KappaMab heavy chain variable region, a second (G45)₃ linker, an IgG1 hinge constant region domain, a CD28 transmembrane and intracellular domains, and a CD3 zeta intracellular domain. A diagram of this construct is shown in FIG. 6B.

The third construct of this group was the KM.CAR_CD8a_28z construct, which contains a CD8 alpha stalk (Uniprot P01732, amino acids 138-182) as the spacer, and whose nucleic sequence is as follows:

(SEQ ID NO: 31)
ATGGAGTTTGGGCTGAGCTGGCTTTTTCTTGTGGCTATTTTAAAAGG

TGTCCAGTGCTCTAGAGACATCGTCATGACCCAGTCTCAAAAATTCATGT

CCACATCAGTAGGAGACAGGGTCAGCGTCACCTGCAAGGCCAGTCAGAAT

GTGGGTACTAATGTAGCCTGGTATCAACAGAAACCAGGGCAATCTCCTAA

AGCACTGATTTACTCGACATCCTACCGGTACAGTGGAGTCCCTGATCGCT

TCACAGGCAGTGGATCTGGGACAGATTTCACTCTCACCATCAGCAATGTG

CAGTCTGAAGACTTGGCAGAGTATTTCTGTCAGCAATATAACAGCTATCC

GTACACGTTCGGAGGGGGGACCAAGCTGGAAATAAAG<u>GGTGGCGGTGGCT</u>

<u>CGGGCGGTGGTGGGTCGGGTGGCGGCGGATCT</u>GAGGTGCAGCTGCAGCAG

TCAGGGGCGGAGCTTGTGAAGCCAGGGGCCTCAGTCAAGTTGTCCTGTAC

AGCTTCTGGCTTCAACATTAAAGACACCTATATGCACTGGGTGAAGCAGA

GGCCTGAACAGGGCCTGGAGTGGATTGGAAGGATTGATCCTGCGAATGGT

AACACTAAATATGACCCGAAGTTCCAGGGCAAGGCCACTATAATAGCAGA

CACATCCTCCAACACAGCCTACCTGCAGCTCAGCAGCCTGACATCTGAGG

ACACTGCCGTCTATTACTGTGCTAGGGGGTCTACCATGATTACGACGGG

GACTACTGGGGCCAAGGGACCACGCTCACCGTCTCCTCC<u>ACCACGACGCC</u>

<u>AGCGCCGCGACCACCAACACCGGCGCCCACCATCGCGTCGCAGCCCCTGT</u>

<u>CCCTGCGCCCAGAGGCGTGCCGGCCAGCGGCGGGGGGCGCAGTGCACACG</u>

<u>AGGGGGCTGGACTTCGCCTGTG</u>ATTTTTGGGTGCTGGTGGTG

GTTGGTGGAGTCCTGGCTTGCTATAGCTTGCTAGTAA

CAGTGGCCTTTATTATTTTCTGGGTGAGGAGTAAGAGGA

GCAGGCTCCTGCACAGTGACTACATGAACATGACTCC

GGGCCCACCCGCAAGCATTACCAGCCCTATGCCCCGCCGCCCC

CACCACGCGACTTCGCAGCCTATCGCTCC<u>AGAGTGAAGTTCAGCAGG</u>

<u>AGCGCAGACGCCCCGCGTACCAGCAGGGCCAGAACCAGCTCTATAACG</u>

<u>AGCTCAATCTAGGACGAAGAGAGGAGTACGATGTTTTGGACAAGAGACG</u>

<u>TGGCCGGGACCCTGAGATGGGGGAAAGCCGAGAAGGAAGAACCCTCAG</u>

<u>GAAGGCCTGTACAATGAACTGCAGAAAGATAAGATGGCGGAGGCCTACA</u>

<u>GTGAGATTGGGATGAAAGGCGAGCGCCGGAGGGGCAAGGGGCACGATGG</u>

<u>CCTTTACCAGGGTCTCAGTACAGCCACCAAGGACACCTACGACGCCCTT</u>

<u>CACATGCAGGCCCTGCCCCCTCGC</u>.

From 5' to 3', this construct (SEQ ID NO: 31) has a leader peptide, a KappaMab light chain variable region, a (G4S)₃ linker, a KappaMab heavy chain variable region, a CD8 alpha stalk, a CD28 transmembrane and intracellular domains, and a CD3 zeta intracellular domain.

The remaining 3 constructs of the 6 KM.CAR constructs described in this example contained a 4-1BB (CD137) Costimulatory Endodomain and were as follows:

The first construct of this group is KM.CAR_h_28TM_41BBz, which contains only the hinge domain of IgG1 heavy chain constant region as the spacer and replaces the intracellular domain of CD28 with the intracellular domain of the 4-1BB co-stimulatory molecule, and whose nucleic acid sequence is as follows:

(SEQ ID NO: 32)
ATGGAGTTTGGGCTGAGCTGGCTTTTTCTTGTGGCTATTTTAAAAGG

TGTCCAGTGCTCTAGAGACATCGTCATGACCCAGTCTCAAAAATTCATG

TCCACATCAGTAGGAGACAGGGTCAGCGTCACCTGCAAGGCCAGTCAGA

ATGTGGGTACTAATGTAGCCTGGTATCAACAGAAACCAGGGCAATCTCC

TAAAGCACTGATTTACTCGACATCCTACCGGTACAGTGGAGTCCCTGAT

CGCTTCACAGGCAGTGGATCTGGGACAGATTTCACTCTCACCATCAGCA

ATGTGCAGTCTGAAGACTTGGCAGAGTATTTCTGTCAGCAATATAACAG

CTATCCGTACACGTTCGGAGGGGGGACCAAGCTGGAAATAAAG<u>GGTGGC</u>

<u>GGTGGCTCGGGCGGTGGTGGGTCGGGTGGCGGCGGATCT</u>GAGGTGCAGC

TGCAGCAGTCAGGGGCGGAGCTTGTGAAGCCAGGGGCCTCAGTCAAGTT

GTCCTGTACAGCTTCTGGCTTCAACATTAAAGACACCTATATGCACTGG

GTGAAGCAGAGGCCTGAACAGGGCCTGGAGTGGATTGGAAGGATTGATC

CTGCGAATGGTAACACTAAATATGACCCGAAGTTCCAGGGCAAGGCCAC

TATAATAGCAGACACATCCTCCAACACAGCCTACCTGCAGCTCAGCAGC

CTGACATCTGAGGACACTGCCGTCTATTACTGTGCTAGGGGGTCTACC

ATGATTACGACGGGGACTACTGGGGCCAAGGGACCACGCTCACCGTCTC

CTCC<u>GGTGGAGGCGGGTCTGGGGGCGGAGGTTCAGGCGGGGGTGGTTCC</u>

<u>GAGCCCAAATCTCCTGACAAAACTCACACATGCCCATTTTGGGTGCT</u>

<u>GGTGGTGGTTGGTGGAGTCCTGGCTTGCTATAGCTTGCTAGT</u>

<u>AACAGTGGCCTTTATTATTTTCTGGGTGAAACGGGGCA</u>

<u>GAAAGAAACTCCTGTATATATTCAAACAACCATTTAT</u>

<u>GAGACCAGTACAAACTACTCAAGAGGAAGATGGCTGT</u>

<u>AGCTGCCGATTTCCAGAAGAAGAAGAAGGAGGATGTGAACTG</u>

<u>AGAGTGAAGTTCAGCAGGAGCGCA</u>

<u>GACGCCCCGCGTACCAGCAGGGCCAGAACCAGCTCTATAACGAGCT</u>

<u>CAATCTAGGACGAAGAGAGGAGTACGATGTTTTGGACAAGAGACGTG</u>

<u>GCCGGGACCCTGAGATGGGGGAAAGCCGAGAAGGAAGAACCCTCAG</u>

<u>GAAGGCCTGTACAATGAACTGCAGAAAGATAAGATGGCGGAGGCCTA</u>

<u>CAGTGAGATTGGGATGAAAGGCGAGCGCCGGAGGGGCAAGGGGCACG</u>

<u>ATGGCCTTTACCAGGGTCTCAGTACAGCCACCAAGGACACCTACGAC</u>

<u>GCCCTTCACATGCAGGCCCTGCCCCCTCGC</u>.

From 5' to 3', this construct (SEQ ID NO: 32) has a leader peptide, a KappaMab light chain variable region, a (G4S)₃ linker, a KappaMab heavy chain variable region, a second (G4S)₃ linker, an IgG hinge constant region domain, a CD28 transmembrane domain, a 4-1BB intracellular domain, and a CD3 zeta intracellular domain.

The second construct of this group was KM.CAR_8a_28TM_41BBz, which contains the CD8 alpha stalk (Uniprot P01732, amino acids 138-182) as the spacer and replaces the intracellular domain of CD28 with the intracellular domain of the 4-1BB co-stimulatory molecule, and whose nucleic sequence is as follows:

(SEQ ID NO: 33)
ATGGAGTTTGGGCTGAGCTGGCTTTTTCTTGTGGCTATTTTAAAAGG
TGTCCAGTGCTCTAGAGACATCGTCATGACCCAGTCTCAAAAATTCATGT
CCACATCAGTAGGAGACAGGGTCAGCGTCACCTGCAAGGCCAGTCAGAAT
GTGGGTACTAATGTAGCCTGGTATCAACAGAAACCAGGGCAATCTCCTAA
AGCACTGATTTACTCGACATCCTACCGGTACAGTGGAGTCCCTGATCGCT
TCACAGGCAGTGGATCTGGGACAGATTTCACTCTCACCATCAGCAATGTG
CAGTCTGAAGACTTGGCAGAGTATTTCTGTCAGCAATATAACAGCTATCC
GTACACGTTCGGAGGGGGGACCAAGCTGGAAATAAAG<u>GGTGGCGGTGGCT</u>
<u>CGGGCGGTGGTGGGTCGGGTGGCGGCGGATCT</u>GAGGTGCAGCTGCAGCAG
TCAGGGGCGGAGCTTGTGAAGCCAGGGGCCTCAGTCAAGTTGTCCTGTAC
AGCTTCTGGCTTCAACATTAAAGACACCTATATGCACTGGGTGAAGCAGA
GGCCTGAACAGGGCCTGGAGTGGATTGGAAGGATTGATCCTGCGAATGGT
AACACTAAATATGACCCGAAGTTCCAGGGCAAGGCCACTATAATAGCAGA
CACATCCTCCAACACAGCCTACCTGCAGCTCAGCAGCCTGACATCTGAGG
ACACTGCCGTCTATTACTGTGCTAGGGGGGTCTACCATGATTACGACGGG
GACTACTGGGGCCAAGGGACCACGCTCACCGTCTCCTCCACCACGACGCC
AGCGCCGCGACCACCAACACCGGCGCCCACCATCGCGTCGCAGCCCCTGT
CCCTGCGCCCAGAGGCGTGCCGGCCAGCGGCGGGGGCGCAGTGCACACG
AGGGGGCTGGACTTCGCCTGTGATTTTTGGGTGCTGGTGGTGGTT
*GGTGGAGTCCTGGCTTGCTATAGCTTGCTAGTAACAGTGGCCTT*
*TATTATTTTCTGGGTGAAACGGGGCAGAAAGAAACT*
*CCTGTATATATTCAAACAACCATTTATGAGACCAGTACAA*
*ACTACTCAAGAGGAAGATGGCTGTACTGCCGATTTCCAGAAGAAG*
*AAGAAGGAGGATGTGAACTG*AGAGTGAAGTTCAGCAGGAGCGCAGA
CGCCCCCGCGTACCAGCAGGGCCAGAACCAGCTCTATAACGAGCTCAA
TCTAGGACGAAGAGAGGAGTACGATGTTTTGGACAAGAGACGTGGCCG
GGACCCTGAGATGGGGGAAAGCCGAGAAGGAAGAACCCTCAGGAAGG
CCTGTACAATGAACTGCAGAAAGATAAGATGGCGGAGGCCTACAGTGA
GATTGGGATGAAAGGCGAGCGCCGAGGGGCAAGGGGCACGATGGCCT
TTACCAGGGTCTCAGTACAGCCACCAAGGACACCTACGACGCCCTTCA
CATGCAGGCCCTGCCCCCTCGC.

From 5′ to 3′, this construct (SEQ ID NO: 33) has a leader peptide, a KappaMab light chain variable region, a (G4S)₃ linker, a KappaMab heavy chain variable region, a CD8 alpha stalk, a CD28 transmembrane domain, a 4-1BB intracellular domain, and a CD3 zeta intracellular domain.

The third construct of this group is KM.CAR_hCH2CH3mut_28TM_41BBz, which contains the hinge, CH2 and CH3 domains of IgG1 heavy chain constant region as the spacer, with mutations introduced at amino acids important for CH2 interaction with Fc-receptors (3-6) which may mediate reduced CAR T-cell survival in-vivo (3, 6, 7) by clearance of CAR T-cells in the reticuloendothelial system. The nucleic acid sequence is as follows:

(SEQ ID NO: 34)
ATGGAGTTTGGGCTGAGCTGGCTTTTTCTTGTGGCTATTTTAAAAGG
TGTCCAGTGCTCTAGAGACATCGTCATGACCCAGTCTCAAAAATTCAT
GTCCACATCAGTAGGAGACAGGGTCAGCGTCACCTGCAAGGCCAGTCA
GAATGTGGGTACTAATGTAGCCTGGTATCAACAGAAACCAGGGCAATC
TCCTAAAGCACTGATTTACTCGACATCCTACCGGTACAGTGGAGTCCC
TGATCGCTTCACAGGCAGTGGATCTGGGACAGATTTCACTCTCACCAT
CAGCAATGTGCAGTCTGAAGACTTGGCAGAGTATTTCTGTCAGCAATA
TAACAGCTATCCGTACACGTTCGGAGGGGGGACCAAGCTGGAAATAAA
<u>GGGTGGCGGTGGCTCGGGCGGTGGTGGGTCGGGTGGCGGCGGATCTGA</u>
GGTGCAGCTGCAGCAGTCAGGGGCGGAGCTTGTGAAGCCAGGGGCCTC
AGTCAAGTTGTCCTGTACAGCTTCTGGCTTCAACATTAAAGACACCTA
TATGCACTGGGTGAAGCAGAGGCCTGAACAGGGCCTGGAGTGGATTGG
AAGGATTGATCCTGCGAATGGTAACACTAAATATGACCCGAAGTTCCA
GGGCAAGGCCACTATAATAGCAGACACATCCTCCAACACAGCCTACCT
GCAGCTCAGCAGCCTGACATCTGAGGACACTGCCGTCTATTACTGTGC
TAGGGGGGTCTACCATGATTACGACGGGGACTACTGGGGCCAAGGGAC
CACGCTCACCGTCTCCTCC<u>GGTGGAGGCGGGTCTGGGGGCGGAGGTTC</u>
AGGCGGGGGTGGTTCCGAGCCCAAATCTCCTGACAAAACTCACACATG
CCCACCGTGCCCAGCACCT<u>CC</u>AGT<u>CGC</u>GGGACCGTCAGTCTTCCTCTT
CCCCCCAAAACCCAAGGACACCCTCATGATCG<u>CCC</u>CGGACCCCTGAGGT
CACATGCGTGGTGGTG<u>AA</u>C<u>G</u>TGAGCCACGAAGACCCTGAGGTCAAGTT
CAACTGGTACGTGGACGGCGTGGAGGTGCATAATGCCAAGACAAAGCC
GCGGGAGGAGCAGTAC<u>GCC</u>AGCACGTACCGTGTGGTCAGCGTCCTCAC
CGTCCTGCACCAGGACTGGCTGAATGGCAAGGAGTACAAGTGCAAGGT
CTCCAACAAAGCCCTCCCAGCCCCCATCGAGAAAACCATCTCCAAAGC
CAAAGGGCAGCCCCGAGAACCACAGGTGTACACCCTGCCCCCATCCCG
GGATGAGCTGACCAAGAACCAGGTCAGCCTGACCTGCCTGGTCAAAGG
CTTCTATCCCAGCGACATCGCCGTGGAGTGGGAGAGCAATGGGCAGCC
GGAGAACAACTACAAGACCACGCCTCCCGTGCTGGACTCCGACGGCTC
CTTCTTCCTCTACAGCAAGCTCACCGTGGACAAGAGCAGGTGGCAGCA
GGGGAACGTCTTCTCATGCTCCGTGATGCATGAGGCTCTGCACAACCA
CTACACACAGAAGAGCCTCTCCCTGTCTCCGGGTAAA*TTTGGGTGCT*
*GGTGGTGGTTGGTGGAGTCCTGGCTTGCTATAGCTTGCTAGTAA*
*CAGTGGCCTTTATTATTTTCTGGGTG*<u>AAACGGGGCAGAAAGAAA</u>

-continued

```
CTCCTGTATATATTCAAACAACCATTTATGAGACCAGTACAAAC

TACTCAAGAGGAAGATGGCTGTAGCTGCCGATTTCCAGAAGAAG

AAGAAGGAGGATGTGAACTGAGAGTGAAGTTCAGCAGGAGCGCAG

ACGCCCCGCGTACCAGCAGGGCCAGAACCAGCTCTATAACGAGCTCA

ATCTAGGACGAAGAGAGGAGTACGATGTTTTGGACAAGAGACGTGGCC

GGGACCCTGAGATGGGGGGAAAGCCGAGAAGGAAGAACCCTCAGGAAG

GCCTGTACAATGAACTGCAGAAAGATAAGATGGCGGAGGCCTACAGTC

AGATTGGGATGAAAGGCGAGCGCCGGAGGGGCAAGGGGCACGATGGCC

TTTACCAGGGTCTCAGTACAGCCACCAAGGACACCTACGACGCCCTTC

ACATGCAGGCCCTGCCCCCTCGC.
```

From 5' to 3', this construct (SEQ ID NO: 34) has a leader peptide, a KappaMab light chain variable region, a (G4S)$_3$ linker, a KappaMab heavy chain variable region, a second (G4S)$_3$ linker, a mutated IgG1 hinge, CH2 and CH3 constant region domains, a CD28 transmembrane domain, a 4-1BB intracellular domain, and a CD3 zeta intracellular domain. The mutated IgG1 hinge domain has, from 5' to 3', E233P, L234V, L235A, G236-, S254A, D265N, and N297A mutations highlighted within the shaded boxes of this construct (SEQ ID NO: 34). Mutations at these sites (E233P, L234V, L235A, G236-, S254A, D265N, N297A) may decrease Fc interaction with CAR T-cells, allowing improved survival post-infusion.

Addition of 2A ribosomal skip element and eGFP to KM.CARs

For ease of detection of T-cells expressing each of the CARs described above, an eGFP with a 5' T2A ribosomal skip element with overlapping sequences was synthesized with the CAR-CD3 zeta endodomain and the plasmid backbone. This was then cloned by restriction enzyme digestion and ligation into the CAR containing pVAX1 PB transposon plasmids to create the following—

28z Endodomain_2A_GFP Containing Constructs:
1. pVAX1PB KM.CAR_hCH2CH3_28z_2A_GFP
2. pVAX1PB KM.CAR_hCH3_28z_2A_GFP
3. pVAX1PB KM.CAR_h_28z_2A_GFP
4. pVAX1PB KM.CAR_8a_28z_2A_GFP 41BBz Endodomain_2A_GFP containing constructs:
1. pVAX1PB KM.CAR_h_28TM_41BBz_2A_GFP
2. pVAX1PB KM. CAR_8a_28TM_41BBz_2A_GFP
3. pVAX1PB KM.CAR_hCH2CH3mut_28TM_41BBz_2A_GFP Generation of KM.CAR T-cells with 4-1BB costimulatory domain.

Comparison was made between the preliminary KM.CAR_hCH2CH3_28z and the 4-1BB containing CARs. KM.CAR T-cells were generated by electroporation using the PiggyBac system as previously described herein and in the art (2). Four million peripheral blood mononuclear cells (PBMCs) from healthy donors were electroporated with the Neon electroporation system at 2400V for 20 ms, single pulse, in the presence of 5 ug each of PiggyBac transposase and PiggyBac Transposon plasmids. KMA.CAR constructs tested included KM.CAR_hCH2CH3_28z_2A_GFP; KM.CAR_h_28TM_41BBz_2A_GFP; KM.CAR_8a_28TM_41BBz_2A_GFP; or KM.CAR_hCH2CH3mut_28TM_41BBz_2A_GFP.

Electroporated PBMCs (CAR-PBMCs) were rested overnight in AIMV with 10% Fetal calf serum (AIM-V CM), harvested, washed and resuspended in AIM-V CM at 1×10$^6$/ml. CAR-PBMCs were cocultured with autologous irradiated PBMC feeder cells with or without irradiated KMA expressing JJN3 cells at a CAR-PBMC:JJN3 ratio of 5:1. Interleukin-15 (IL-15) was added at 10 ng/ml every 3 days. Cells were enumerated by trypan blue exclusion and fresh irradiated stimulator/feeder cells were added every 7 days.

Assessment of KM.CAR Expression

Figure 8A:
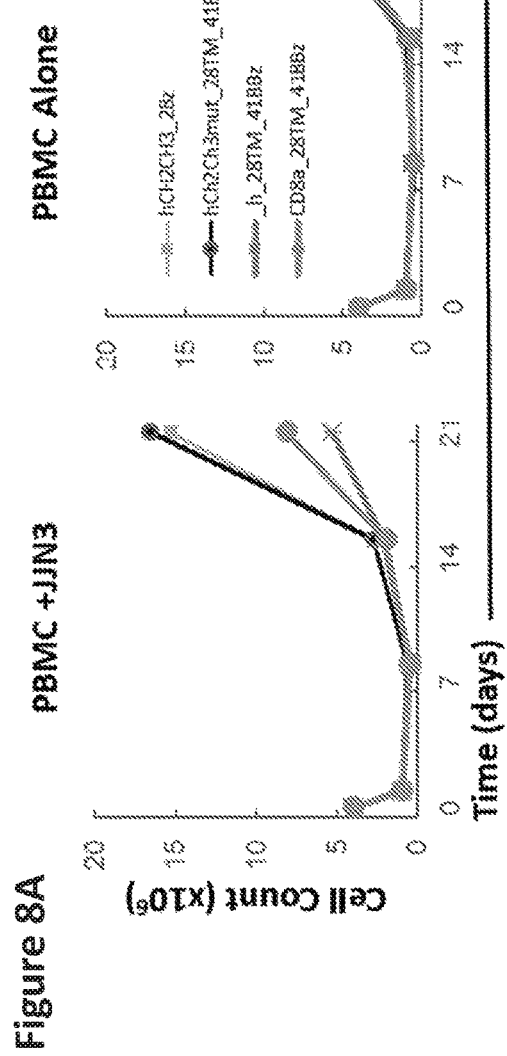
FIGS. 8A-8B shows KM. CAR T-cell expansion and CAR expression with constructs described in Example 3.
Figure 8B:
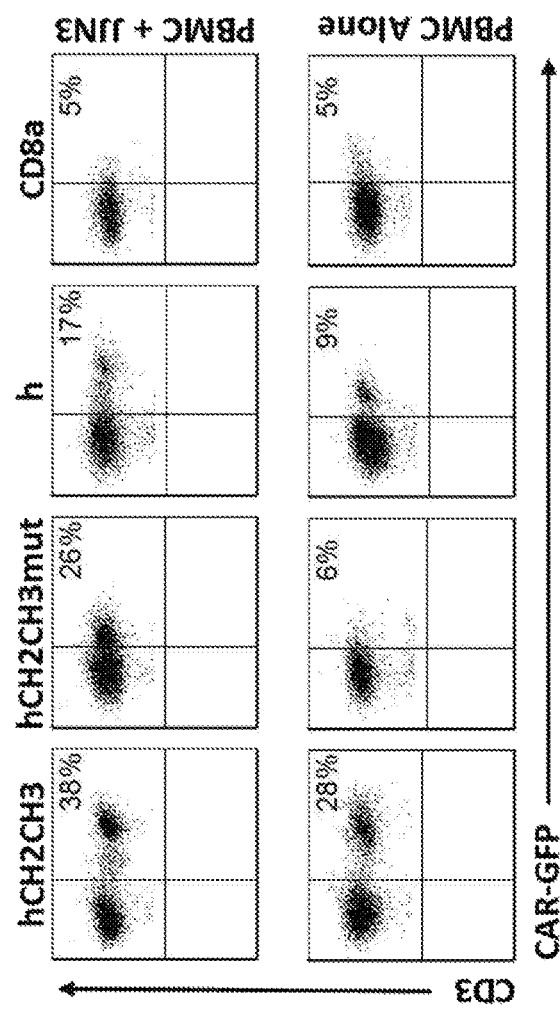

KM.CAR expression was assessed by flow cytometry at initiation of culture (Day 1), Day 15 and Day 21 (FIGS. 8A-8B). KM.CAR T-cell cultures were surface stained with anti-human-CD3 antibody and CAR expression assessed by GFP expression.

KM.CAR T-Cells Require Kappa Myeloma Antigen to Persist In-Vitro

Cultures containing the KMA expressing JJN3 cell line showed either greater total expansion, increased KM.CAR expression or both, compared to cultures with PBMC alone (FIGS. 8A-8B). Consistent with known interaction of the IgG constant region-CH2 domain with Fc-receptors, the KM.CAR_hCH2CH3_28z expressing T-cells were enriched in the presence of PBMC alone (28% of CD3$^+$ T-cells), but showed greater expansion and enrichment with addition of JJN3 cells (15-fold expansion with 38% CAR expression compared to 6-fold expansion with 29% CAR expression).

KM.CAR_hCH2CH3mut_28TM_41BBz expressing T-cells showed only low level CAR expression (6%) and expansion (6-fold) with PBMC alone compared to co-culture with JJN3 (26% CAR expression and 17-fold expansion). The KM.CAR T-cells containing the IgG1 hinge only spacer had similar expansion (5-fold with JJN3, 6 fold without JJN3) but increased CAR expression (17% with JJN3, 9% without). Only the KM.CAR T-cells containing the CD8alpha chain spacer did not show any enhanced expansion or enrichment in the presence of JJN3 cells (8-fold expansion and 5% CAR expression in the presence of JJN3, compared to 5-fold expansion and 5% CAR expression without JJN3).

Functional Assessment of KM.CAR T-Cells

KMA-specific interferon-gamma production and cytotoxicity of KM.CAR T-cells were assessed by intracellular cytokine flow cytometry and standard chromium release assay with KMA+ and KMA− cell lines using protocols previously described (2). KMA positive cell lines used included JJN3, Pfeiffer, NCI-H929. KMA negative cell lines included Nalm-6 and Molt (FIGS. 12A-12B).

For cytokine flow cytometry, 2×10$^5$ KM.CAR T-cells were stimulated with target cells at a ratio of 1:1 for 5 hours. Monensin (2 µM) (BD Biosciences) and Brefeldin A (1 µg/mL) (BD Biosciences) were added after 1 hour. CAR T-cells activated non-specifically with 50 ng/ml phorbol myristate acetate (PMA: Sigma-Aldrich) and 1 ug/ml ionomycin (Sigma-Aldrich) and unstimulated cells were used as positive and negative controls. CAR T-cells were then harvested, washed, surface stained for CD3, CD4 and CD8. CAR T-cells were fixed and permeabilised with cytofix and perm/wash buffer (BD Biosciences) and stained with anti-interferon gamma antibody (BD Biosciences) followed by further washing with perm/wash buffer. Stained cells were analysed using a FACSCanto™ II flow cytometer with acquisition of at least 30,000 events.

KMA-specific cytotoxicity was assessed using a standard chromium ($^{51}$Cr) release assay. Target cells were labelled with Sodium chromate (Na$_2$$^{51}$CrO$_4$) (Perkin-Elmer, Waltham, Mass., USA). KM.CAR T-cells were preincubated with the K562 cell line at a 1:1 ratio to absorb NK cell activity. Chromium labelled target cells were added to the KM.CAR T-cells in triplicate at effector:target ratios ranging from 40:1 to 1.25:1 and incubated at 37° C., 5% $CO_2$ for 4 hours. Triplicate targets were lysed with 10% sodium dodecyl sulphate to determine maximal release and triplicate targets with no effectors were used to assess spontaneous release. Supernatants were aspirated and read using a Micro-Beta2 Plate Counter (PerkinElmer). Percentage specific lysis was calculated using the standard formula-% Specific lysis= (test release−spontaneous release)/(maximal release−spontaneous release)×100]

Example 4

Generation of PiggyBac Transposon Plasmid with the Activation Inducible Promoter A single transposon cassette containing a constitutively active promoter (EF1alpha) and an activation inducible promoter (NFATpro) was designed and cloned. The activation inducible gene expression cassette was produced by designing the NFATpro using Clone Manage 9 (Sci-Ed Software), based on Fiering et al(8). This includes 6 copies of the 30 base pair DNA sequence (response element-RE) bound by the Nuclear Factor of Activated T-cells (NFAT-RE)-GGAGGAAAAACTGTTTCATACAGAAGGCGT (SEQ ID NO: 35) followed by the minimal IL-2 promoter-ACATTTTGACACCCCCATAATATTTTTCCAGAAT-TAACAGTATAAATTGCATCTCT TGTT-CAAGAGTTCCCTATCACTCTCTTTAATCACTACTCA CAGTAACCTCAACTCC TG (SEQ ID NO: 36) found on chromosome 4 (NCBI Reference Sequence: NG_016779.1).

To enable detection of activation induced gene expression, the enhanced green fluorescent protein (eGFP) DNA sequence followed by the bovine growth hormone (BGH) polyadenylation signal (9-11) was placed 3' of the NFATpro. The DNA sequence of this gene cassette is as follows

```
                                          (SEQ ID NO: 37)
GGAGGAAAAACTGTTTCATACAGAAGGCGTCAATTAGGAGGAAAA

ACTGTTTCATACAGAAGGCGTCAATTAGGAGGAAAAACTGTTTCATACAG

AAGGCGTCAATTGTCCCATCGAATTAGGAGGAAAAACTGTTTCATACAGA

AGGCGTCAATTAGGAGGAAAAACTGTTTCATACAGAAGGCGTCAATTAGG

AGGAAAAACTGTTTCATACAGAAGGCGTCAATTGTCCCGGGACATTTTGA

CACCCCCATAATATTTTTCCAGAATTAACAGTATAAATTGCATCTCTTGT

TCAAGAGTTCCCTATCACTCTCTTTAATCACTACTCACAGTAACCTCAAC

TCCTGAACTCCATGGATGGTGAGCAAGGGCGAGGAGCTGTTCACCGGGGT

GGTGCCCATCCTGGTCGAGCTGGACGGCGACGTAAACGGCCACAAGTTCA

GCGTGTCCGGCGAGGGCGAGGGCGATGCCACCTACGGCAAGCTGACCCTG

AAGTTCATCTGCACCACCGGCAAGCTGCCCGTGCCCTGGCCCACCCTCGT

GACCACCCTGACCTACGGCGTGCAGTGCTTCAGCCGCTACCCCGACCACA

TGAAGCAGCACGACTTCTTCAAGTCCGCCATGCCCGAAGGCTACGTCCAG

GAGCGCACCATCTTCTTCAAGGACGACGGCAACTACAAGACCCGCGCCGA

GGTGAAGTTCGAGGGCGACACCCTGGTGAACCGCATCGAGCTGAAGGGCA

TCGACTTCAAGGAGGACGGCAACATCCTGGGGCACAAGCTGGAGTACAAC

TACAACAGCCACAACGTCTATATCATGGCCGACAAGCAGAAGAACGGCAT

CAAGGTGAACTTCAAGATCCGCCACAACATCGAGGACGGCAGCGTGCAGC

TCGCCGACCACTACCAGCAGAACACCCCCATCGGATCCGGAGCCACGAAC

TTCTCTCTGTTAAAGCAAGCAGGAGACGTTGAAGAAAACCCCGGTCCTAT

TTAAATCCTCGACTGTGCCTTCTAGTTGCCAGCCATCTGTTGTTTGCCCC

TCCCCCGTGCCTTCCTTGACCCTGGAAGGTGCCACTCCCACTGTCCTTTC

CTAATAAAATGAGGAAATTGCATCGCATTGTCTGAGTAGGTGTCATTCTA

TTCTGGGGGGTGGGGTGGGGCAGGACAGCAAGGGGGAGGATTGGGAAGAC

AATAGCAGGCATGCTGGGGATGCGGTGGGCTCTATGGC.
```

From 5' to 3', this constructs contains the NFAT-RE, the IL-2 Minimal Promoter, the eGFP, and the BGH polyadenylation signal.

This cassette was synthesised commercially by Genscript and cloned into the pVAX1PB transposon plasmid between the 5' cHS4 Insulator (GenBank: U78775.2)(12) and the human elongation factor 1 promoter. To identify transduced T-cells in initial experiments, the chimeric RQR8 marker consisting of the epitope of CD34 recognised by the QBEnd10 monoclonal antibody and mimotopes of the CD20-specific monoclonal antibody Rituximab(13) was cloned into the transposon multicloning site to produce the transposon gene insert shown in FIG. 9 (pVAX1PB NFATGFP-RQR8 plasmid). Co-electroporation of the activation inducible gene cassette containing pVAX1PB NFATGFP-RQR8 transposon plasmid and the pVAX1 PBase transposase plasmid leads to permanent integration of the NFATGFP-RQR8 gene insert seen in FIG. 9.

Demonstration of Function of the Activation Inducible Gene Containing Transposon To demonstrate the function of the pVAX1PB NFATGFP-RQR8 transposon from Example 4 (see FIG. 9), $4 \times 10^6$ PBMCs were electroporated in the presence of 5 ug each of the transposon and transposase plasmids. Electroporated cells were rested for 24 hours and then stimulated non-specifically over-night with 50 ng/ml phorbol myristate acetate (PMA: Sigma-Aldrich) and 1ug/ml ionomycin (Sigma-Aldrich) and compared to unstimulated controls. Transduced cells were identified by QBEnd10 staining for RQR8 marker expression and activation induced gene expression (eGFP) was assessed at 19 hours. At that time point, 50% of transduced cells were seen to express eGFP (FIG. 10).

Example 5

Design of KM.CAR Controlled Biological Therapies

Expression plasmids containing IL-12 and/or the interleukin-6 receptor antagonist SANT7and also containing the optimized chimeric antigen receptor with the expression of IL-12 and/or SANT7 under control of an activation inducible promoter (Hooijberg et al. 2000) were also constructed. The SANT-7 sequence was provided by Prof Rocco Savino and was based on mutating the wildtype IL-6 gene sequence (NCBI Reference Sequence: NM_000600.4) provided as per Savino et al 1994 and Sporeno et al 1996(14-17). The sequence was imported into Clone Manage 9 (Sci-Ed Software) and a 6× His tag added for detection in supernatants by ELISA.

The nucleotide sequence of SANT-7 is provided with amino acid substitutions highlighted, underlined and listed below:

(SEQ ID NO: 38)
MNSFSTSAFGPVAFSLGLLLVLPAAFPAPVPPGEDSKDVAAPHRQPLTS

SERIDKQIRDILDFISALRKETCNKSNMCESSKEADAFWNLNLPKMAEK

DGCFYKGFNEETCLVKIITGLLEFEVYLEYLQNRFESSEEQARAVQMRT

KDLIQFLQKKAKNLDAITTPDPTTNASLLTKLQAQNQWLQDMTTHLILR

SFKEFLIRSLRALRAMHHHHHH.

The nucleotide substitutions correspond to Y31D, G35F, L57D, E59F, N60W, Q75Y, S76K, S118R, V121D. The sequence provided also contained a Q211A substitution not listed in the published sequence.

The DNA sequence corresponding to this amino acid sequence (i.e., SEQ ID NO: 38) is as follows:

(SEQ ID NO: 39)
ATGAACTCCTTCTCCACAAGCGCCTTCGGTCCAGTTGCCTTCTCCCT

GGGGCTGCTCCTGGTGTTGCCTGCTGCCTTCCCTGCCCCAGTACCCCCAG

GAGAAGATTCCAAAGATGTAGCCGCCCCACACAGACAGCCACTCACGAGC

TCAGAACGAATTGACAAACAAATTCGGGACATCCTCGACTTTATCTCAGC

CTTAAGAAAGGAGACATGTAACAAGAGTAACATGTGTGAGAGCTCCAAAG

AGGCAGACGCATTCTGGAACCTGAACCTTCCAAAGATGGCTGAAAAAGAT

GGATGCTTCTACAAAGGATTCAATGAGGAGACTTGCCTGGTGAAAATCAT

CACTGGTCTTCTCGAGTTTGAGGTATACCTAGAGTACCTCCAGAACAGAT

TTGAGAGTAGTGAGGAACAAGCCAGAGCTGTGCAGATGCGCACAAAAGAC

CTGATCCAGTTCCTGCAGAAAAAGGCAAAGAATCTAGATGCAATAACCAC

CCCTGACCCAACCACAAATGCCAGCCTGCTGACGAAGCTGCAGGCACAGA

ACCAGTGGCTGCAGGACATGACAACTCATCTCATTCTGAGATCTTTTAAG

GAGTTCCTGATCCGTAGCCTGAGGGCTCTTCGGGCTATGCATCATCACCA

TCACCACT.

A single chain interleukin-12 (Flexi-IL-12) construct was designed by joining the IL-12 p40 and p35 subunits (Uniprot P29459 and P29460) with a flexible $(G_4S)_3$ linker similar to Zhang et al and Chinnasamy et al (18, 19), which allows both subunits to be expressed as a single peptide chain that readily forms the bioactive p70 heterodimer was used. The Flexi-IL-12 construct was synthesized and constructs containing IL-12 and SANT7 were cloned into the activation inducible transposon cassette described herein and shown in FIG. 11.

Figure 7:
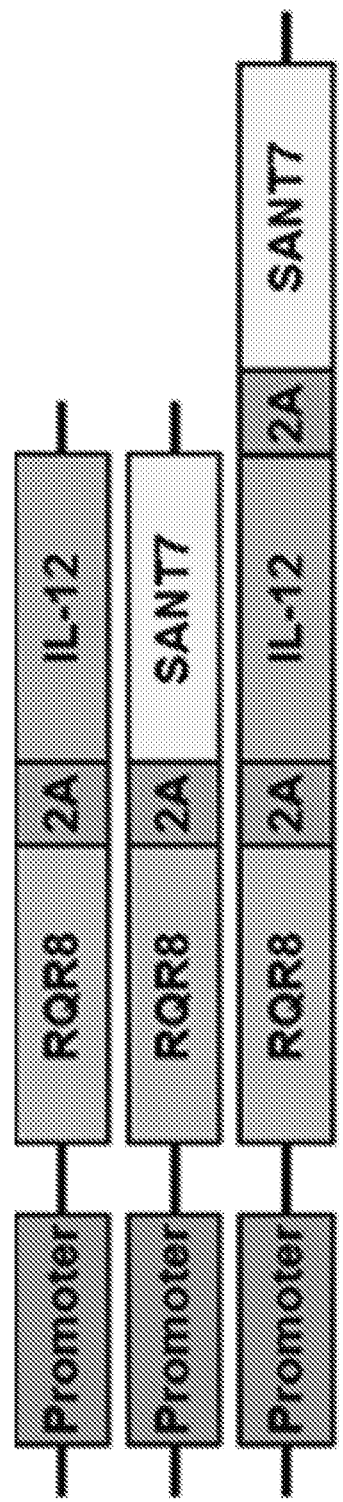
FIG. 7 shows the IL-12 and SANT7 vectors.

Additionally, the Flexi-IL-12 construct could be synthesized and constructs containing IL-12 and SANT7 separated by 2A ribosomal skip elements could be cloned into the PiggyBac plasmid described herein and shown in FIG. 7.

The amino acid sequence of Flexi-IL-12 is as follows:

(SEQ ID NO: 40)
MCHQQLVISWFSLVFLASPLVAIWELKKDVYVVELDWYPDAPGEM

VVLTCDTPEEDGITWTLDQSSEVLGSGKTLTIQVKEFGDAGQYTCHKGGE

VLSHSLLLLHKKEDGIWSTDILKDQKEPKNKTFLRCEAKNYSGRFTCWWL

TTISTDLTFSVKSSRGSSDPQGVTCGAATLSAERVRGDNKEYEYSVECQE

DSACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCSGGGGSGGGGSGGGGS

*RNLPVATPDPGMFPCLHHSQNLLRAVSNMLQKARQTL*

*EFYPCTSEEIDHEDITKDK*

*TSTVEACLPLELTKNESCLNSRETSFITNGSCLASRKTS*

*FMMALCLSSIYEDLKMYQVEFKTMNAKLLMDPKRQIFL*

*DQNMLAVIDELMQALNFNSETVPQKSSLEEPDFYKTK*

*IKLCILLHAFRIRAVTIDRVMSYLNAS*

From 5' to 3', the Flexi-IL-12 construct contains a leader peptide, the IL-12 p40 subunit, the $(G4S)_3$Linker, and the IL-12 p35 subunit.

The DNA sequence corresponding to the amino acid sequence above (i.e., SEQ ID NO: 40) is as follows:

(SEQ ID NO: 41)
ATGTGTCACCAGCAGTTGGTCATCTCTTGGTTTTCCCTGGTTTTTCT

GGCATCTCCCCTCGTGGCCATATGGGAACTGAAGAAAGATGTTTATGTCG

TAGAATTGGATTGGTATCCGGATGCCCCTGGAGAAATGGTGGTCCTCACC

TGTGACACCCCTGAAGAAGATGGTATCACCTGGACCTTGGACCAGAGCAG

TGAGGTCTTAGGCTCTGGCAAAACCCTGACCATCCAAGTCAAAGAGTTTG

GAGATGCTGGCCAGTACACCTGTCACAAAGGAGGCGAGGTTCTAAGCCAT

TCGCTCCTGCTGCTTCACAAAAAGGAAGATGGAATTTGGTCCACTGATAT

TTTAAAGGACCAGAAAGAACCCAAAAATAAGACCTTTCTAAGATGCGAGG

CCAAGAATTATTCTGGACGTTTCACCTGCTGGTGGCTGACGACAATCAGT

ACTGATTTGACATTCAGTGTCAAAAGCAGCAGAGGCTCTTCTGACCCCCA

AGGGGTGACGTGCGGAGCTGCTACACTCTCTGCAGAGAGAGTCAGAGGGG

ACAACAAGGAGTATGAGTACTCAGTGGAGTGCCAGGAGGACAGTGCCTGC

CCAGCTGCTGAGGAGAGTCTGCCCATTGAGGTCATGGTGGATGCCGTTCA

CAAGCTCAAGTATGAAAACTACACCAGCAGCTTCTTCATCAGGGACATCA

TCAAACCTGACCCACCCAAGAACTTGCAGCTGAAGCCATTAAAGAATTCT

CGGCAGGTGGAGGTCAGCTGGGAGTACCCTGACACCTGGAGTACTCCACA

TTCCTACTTCTCCCTGACATTCTGCGTTCAGGTCCAGGGCAAGAGCAAGA

GAGAAAAGAAAGATAGAGTCTTCACGGACAAGACCTCAGCCACGGTCATC

TGCCGCAAAAATGCCAGCATTAGCGTGCGGGCCCAGGACCGCTACTATAG

CTCATCTTGGAGCGAATGGGCATCTGTGCCCTGCAGTGGTGGCGGTGGAA

GCGGCGGTGGCGGAAGCGGCGGTGGCGGCAGCAGAAACCTCCCCGTGGCC

-continued
```
ACTCCAGACCCAGGAATGTTCCCATGCCTTCACCACTCCCAAAACCTGCT

GAGGGCCGTCAGCAACATGCTCCAGAAGGCCAGACAAACTCTAGAATTTT

ACCCTTGCACTTCTGAAGAGATTGATCATGAAGATATCACAAAAGATAAA

ACCAGCACAGTGGAGGCCTGTTTACCATTGGAATTAACCAAGAATGAGAG

TTGCCTAAATTCCAGAGAGACCTCTTTCATAACTAATGGGAGTTGCCTGG

CCTCCAGAAAGACCTCTTTTATGATGGCCCTGTGCCTTAGTAGTATTTAT

GAAGACTTGAAGATGTACCAGGTGGAGTTCAAGACCATGAATGCAAAGCT

TCTGATGGATCCTAAGAGGCAGATCTTTCTAGATCAAAACATGCTGGCAG

TTATTGATGAGCTGATGCAGGCCCTGAATTTCAACAGTGAGACTGTGCCA

CAAAAATCCTCCCTTGAAGAACCGGATTTTTATAAAACTAAAATCAAGCT

CTGCATACTTCTTCATGCTTTCAGAATTCGGGCAGTGACTATTGATAGAG

TGATGAGCTATCTGAATGCTTCC.
```

Additionally, expression plasmids containing the truncated dominant negative form of Galectin-3, GAL3C is also constructed. The construct contains a CD8-alpha leader peptide to direct secretion as well as a 6× His tag for detection. The amino acid sequence of GAL3C is listed here:

(SEQ ID NO: 42)
MEFGLSWLFLVAILKGVQCSRHHHHHHGAPAGPLIVPYNLPLPGGV

VPRMLITILGTVKPNANRIALDFQRGNDVAFHFNPRFNENNRRVIVCNTK

LDNNWGREERQSVFPFESGKPFKIQVLVEPDHFKVAVNDAHLLQYNHRVK

KLNEISKLGISGDIDLTSASYTMI

The corresponding DNA sequence for the GAL 3C construct is provided here:

(SEQ ID NO: 43)
```
ATGGAGTTTGGGCTGAGCTGGCTTTTTCTTGTGGCTATTTTAAAAGG

TGTCCAGTGCTCTAGACATCATCACCATCACCACGGCGCCCCTGCTGGGC

CACTGATTGTGCCTTATAACCTGCCTTTGCCTGGGGGAGTGGTGCCTCGC

ATGCTGATAACAATTCTGGGCACGGTGAAGCCCAATGCAAACAGAATTGC

TTTAGATTTCCAAAGAGGGAATGATGTTGCCTTCCACTTTAACCCACGCT

TCAATGAGAACAACAGGAGAGTCATTGTTTGCAATACAAAGCTGGATAAT

AACTGGGGAAGGGAAGAAAGACAGTCGGTTTTCCCATTTGAAAGTGGGAA

ACCATTCAAAATACAAGTACTGGTTGAACCTGACCACTTCAAGGTTGCAG

TGAATGATGCTCACTTGTTGCAGTACAATCATCGGGTTAAAAAACTCAAT

GAAATCAGCAAACTGGGAATTTCTGGTGACATAGACCTCACCAGTGCTTC

ATATACCATGATA
```

The CAR and 'biologicals' transposon plasmids will be nucleofected to generate CAR T-cells expressing either IL-12 alone, SANT7 alone, GAL3C alone or both IL-12 and SANT7 or both of IL12 and GAL3C or both of SANT7 and GAL3C or all three of IL-12. SANT7 and GAL3C. Cells successfully transduced with 'biologicals' constructs may be identified by selectable marker expression for example by flow cytometry. Levels of IL-12, SANT7. And or GAL3C will be measured intracellularly by cytokine flow cytometry and in supernatants of CAR T-cell cultures by ELISA using commercial kits and reagents and compared to control T-cells expressing CAR alone. CAR T-cells will be assessed for function by cytokine flow cytometry and cytotoxicity assays as above as well as co-culture assays with myeloma cell lines to assess inhibition of tumour growth. Experiments will be performed in triplicate and the 2 optimal CAR constructs identified will be chosen to be assessed in a murine model with and without IL-12, GAL3C and/or SANT7 expression.

Based on the previously established RPMI-Rag human myeloma murine xenograft model, RPMI-Rag-Luc (KMA-) and JJN3-Rag-Luc (KMA+) models will be developed to assess the function of our CAR T-cells in-vivo. JJN3 and RPMI8226 cells will be transfected with Luc-1 and then inoculated i.v. into Rag2-/-γc-/- (BALB/c) mice to form the JJN3-Rag-Luc and RPMI-Rag-Luc MM models. Engraftment and disease levels will be monitored by optical imaging following IP injection with luciferin and correlated with levels of levels of serum human kappa (JJN3) and lambda (RPMI) light chain. Optimal time for inoculation with candidate CAR T-cells will be established using Optical Imaging prior to the development of hind limb paralysis, usually from weeks 5-8. Cohorts of 6 JJN3-Rag-Luc and RPMI-Rag-Luc mice will be inoculated IV with increasing doses of CAR T-Cells (with and without IL-12/SANT7 expression) to establish the therapeutic dose starting at $1 \times 10^6$ total cells. Mice will be imaged on day 0, +1, +3, +8 and weekly thereafter until the development disease progression as determined by the development of hind limb paralysis, increasing serum free light chains (SFLC) or other institutional guidelines. Marrow and extramedullary tumors will be collected and examined histologically for distribution of MM cells and CAR T-cells. Efficacy will be determined by imaging response and survival compared with controls.

REFERENCES

1. Rossig C, Pscherer S, Landmeier S, Altvater B, Jurgens H, Vormoor J. Adoptive cellular immunotherapy with CD19-specific T cells. Klin Padiatr. 2005;217(6):351-6.
2. Ramanayake S, Bilmon I, Bishop D, Dubosq M C, Blyth E, Clancy L, et al. Low-cost generation of Good Manufacturing Practice-grade CD19-specific chimeric antigen receptor-expressing T cells using piggyBac gene transfer and patient-derived materials. Cytotherapy. 2015.
3. Hombach A, Hombach A A, Abken H. Adoptive immunotherapy with genetically engineered T cells: modification of the IgG1 Fc 'spacer' domain in the extracellular moiety of chimeric antigen receptors avoids 'off-target' activation and unintended initiation of an innate immune response. Gene Ther. 2010;17(10):1206-13.
4. Shields R L, Namenuk A K, Hong K, Meng YG, Rae J, Briggs J, et al. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001;276(9):6591-604.
5. Armour K L, van de Winkel J G, Williamson L M, Clark M R. Differential binding to human FcgammaRIIa and FcgammaRIIb receptors by human IgG wildtype and mutant antibodies. Mol Immunol. 2003;40(9):585-93.
6. Hudecek M, Sommermeyer D, Kosasih P L, Silva-Benedict A, Liu L, Rader C, et al. The nonsignaling extracellular spacer domain of chimeric antigen receptors is decisive for in vivo antitumor activity. Cancer immunology research. 2015;3(2):125-35.

7. Clemenceau B, Valsesia-Wittmann S, Jallas A C, Vivien R, Rousseau R, Marabelle A, et al. In Vitro and In Vivo Comparison of Lymphocytes Transduced with a Human CD16 or with a Chimeric Antigen Receptor Reveals Potential Off-Target Interactions due to the IgG2 CH2-CH3 CAR-Spacer. J Immunol Res. 2015;2015:482089.

8. Fiering S, Northrop J P, Nolan G P, Mattila P S, Crabtree G R, Herzenberg L A. Single cell assay of a transcription factor reveals a threshold in transcription activated by signals emanating from the T-cell antigen receptor. Genes Dev. 1990;4(10):1823-34.

9. Miller W L, Martial J A, Baxter J D. Molecular cloning of DNA complementary to bovine growth hormone mRNA. J Biol Chem. 1980;255(16):7521-4.

10. Miller W L, Thirion J P, Martial J A. Cloning of DNA complementary to bovine prolactin mRNA. Endocrinology. 1980;107(3):851-3.

11. Goodwin E C, Rottman F M. The 3'-flanking sequence of the bovine growth hormone gene contains novel elements required for efficient and accurate polyadenylation. J Biol Chem. 1992;267(23):16330-4.

12. Chung J H, Bell A C, Felsenfeld G. Characterization of the chicken beta-globin insulator. Proc Natl Acad Sci U S A. 1997;94(2):575-80.

13. Philip B, Thomas S, Marin V, Jathoul A, Kopec A, Linch D C, et al. A Highly Compact Epitope-Based Marker-Suicide Gene for More Convenient and Safer T-Cell Adoptive Immunotherapy. ASH Annual Meeting Abstracts. 2010; 116(21):1473-.

14. Demartis A, Bernassola F, Savino R, Melino G, Ciliberto G. Interleukin 6 receptor superantagonists are potent inducers of human multiple myeloma cell death. Cancer Res. 1996;56(18):4213-8.

15. Savino R, Ciapponi L, Lahm A, Demartis A, Cabibbo A, Toniatti C, et al. Rational design of a receptor super-antagonist of human interleukin-6. EMBO J. 1994;13(24): 5863-70.

16. Savino R, Lahm A, Salvati AL, Ciapponi L, Sporeno E, Altamura S, et al. Generation of interleukin-6 receptor antagonists by molecular-modeling guided mutagenesis of residues important for gp130 activation. EMBO J. 1994;13 (6):1357-67.

17. Sporeno E, Savino R, Ciapponi L, Paonessa G, Cabibbo A, Lahm A, et al. Human interleukin-6 receptor super-antagonists with high potency and wide spectrum on multiple myeloma cells. Blood. 1996;87(11):4510-9.

18. Zhang L, Kerkar S P, Yu Z, Zheng Z, Yang S, Restifo N P, et al. Improving adoptive T cell therapy by targeting and controlling IL-12 expression to the tumor environment. Mol Ther. 2011; 19(4): 751-9.

19. Chinnasamy D, Yu Z, Kerkar S P, Zhang L, Morgan R A, Restifo N P, et al. Local delivery of interleukin-12 using T cells targeting VEGF receptor-2 eradicates multiple vascularized tumors in mice. Clin Cancer Res. 2012;18(6): 1672-83.

What is claimed is:

1. A chimeric antigen receptor (CAR) comprising one or more intracellular signaling domains and an extracellular antigen binding domain, wherein the extracellular antigen binding domain comprises a single chain variable fragment (scFv) that specifically binds kappa myeloma antigen (KMA) and does not bind immunoglobulin (Ig) kappa light chain associated with an Ig heavy chain, wherein the scFv comprises the VL chain and VH chain from KappaMab, wherein the VL chain comprises the VL chain of SEQ ID NO: 2 and the VH chain comprises the VH chain of SEQ ID NO: 1.

2. A chimeric antigen receptor (CAR) comprising one or more intracellular signaling domains and an extracellular antigen binding domain, wherein the extracellular antigen binding domain specifically recognizes kappa myeloma antigen (KMA), wherein the extracellular binding domain comprises a single chain variable fragment (scFv) that specifically recognizes KMA, wherein the scFv comprises the VL chain and VH chain from KappaMab wherein the VL chain comprises the VL chain of SEQ ID NO: 2 and the VH chain comprises the VH chain of SEQ ID NO: 1.

3. The CAR of claim 2, wherein the one or more intracellular signaling domains comprises one or more co-stimulatory endodomains.

4. The CAR of claim 3, wherein the one or more co-stimulatory endodomains is one or more of a CD28 domain, a CD3ζ domain, a 4-1BB domain or OX-40 domain or combinations thereof.

5. The CAR of claim 2, wherein the VL chain and VH chain from KappaMab are attached via a glycine-serine linker.

6. The CAR of claim 5, wherein the glycine-serine linker is a 15-20 amino acid linker, wherein the glycine-serine linker comprises (Gly$_4$Ser)$_3$ (SEQ ID NO: 23).

7. The CAR of claim 2, wherein the scFv is attached to the one or more intracellular signaling domains via a spacer.

8. The CAR of claim 7, wherein the spacer is an immunoglobulin constant region or a CD8α chain.

9. The CAR of claim 8, wherein the immunoglobulin constant region comprises one or more of an IgG hinge domain, an IgG CH2 domain and an IgG CH3 domain.

10. The CAR of claim 8, wherein the spacer is attached to the scFV via a glycine-serine linker.

11. The CAR of claim 10, wherein the glycine-serine linker is a 15-20 amino acid linker, wherein the glycine-serine linker comprises (Gly$_4$Ser)$_3$ (SEQ ID NO: 23).

12. A genetically modified T cell engineered to express the CAR of claim 2.

13. The genetically modified T cell of claim 12, further engineered to express one or more additional biological molecules, and, optionally, a selectable marker.

14. The genetically modified T cell of claim 13, wherein the one or more additional biological molecules comprises one or more of an HGF Binding protein, IL-12, GAL3C or SANT7.

15. The genetically modified T cell of claim 13, wherein the one or more additional biological molecules is IL-12 and the IL-12 is expressed by a single chain polypeptide comprising one IL-12 p35 subunit and one IL-12 p40 subunit joined by a flexible linker.

16. A method for producing a genetically modified T cell comprising introducing into a T cell an expression vector encoding a CAR comprising one or more intracellular signaling domains and an extracellular antigen binding domain, wherein the extracellular antigen binding domain specifically recognizes kappa myeloma antigen (KMA), wherein the extracellular binding domain comprises a single chain variable fragment (scFv) that specifically recognizes KMA, wherein the scFv comprises the VL chain and VH chain from KappaMab wherein the VL chain comprises the VL chain of SEQ ID NO: 2 and the VH chain comprises the VH chain of SEQ ID NO: 1.

17. A method of treating a KMA-expressing malignancy in a subject in need thereof comprising administering genetically modified T cells engineered to express one or more intracellular signaling domains and an extracellular antigen binding domain, wherein the extracellular antigen binding domain specifically recognizes kappa myeloma antigen (KMA), wherein the extracellular binding domain comprises a single chain variable fragment (scFv) that specifically recognizes KMA, wherein the scFv comprises the VL chain and VH chain from KappaMab wherein the VL chain comprises the VL chain of SEQ ID NO: 2 and the VH chain comprises the VH chain of SEQ ID NO: 1.

18. The genetically modified T cell of claim 14, wherein the HGF binding protein is an HGF antibody or fragment thereof.

* * * * *

SEQUENCE LISTING

```
<160> NUMBER OF SEQ ID NOS: 43

<210> SEQ ID NO 1
<211> LENGTH: 449
<212> TYPE: PRT
<213> ORGANISM: Artificial Sequence
<220> FEATURE:
<223> OTHER INFORMATION: human monoclonal antibody heavy chain

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Ile Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Val Tyr His Asp Tyr Asp Gly Asp Tyr Trp Gly Gln Gly
            100                 105                 110

Thr Thr Leu Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                    165                 170                 175
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 214
<212> TYPE: PRT
<213> ORGANISM: Artificial Sequence
<220> FEATURE:
<223> OTHER INFORMATION: human monoclonal antibody light chain

<400> SEQUENCE: 2

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Thr Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80
```

-continued

```
Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 5
<212> TYPE: PRT
<213> ORGANISM: Artificial Sequence
<220> FEATURE:
<223> OTHER INFORMATION: human monoclonal antibody VH CDR

<400> SEQUENCE: 3

Asp Thr Tyr Met His
1               5

<210> SEQ ID NO 4
<211> LENGTH: 17
<212> TYPE: PRT
<213> ORGANISM: Artificial Sequence
<220> FEATURE:
<223> OTHER INFORMATION: human monoclonal antibody VH CDR

<400> SEQUENCE: 4

Arg Ile Asp Pro Ala Asn Gly Asn Thr Lys Tyr Asp Pro Lys Phe Gln
1               5                   10                  15

Gly

<210> SEQ ID NO 5
<211> LENGTH: 10
<212> TYPE: PRT
<213> ORGANISM: Artificial Sequence
<220> FEATURE:
<223> OTHER INFORMATION: human monoclonal antibody VH CDR

<400> SEQUENCE: 5

Gly Val Tyr His Asp Tyr Asp Gly Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: human monoclonal antibody VL CDR

<400> SEQUENCE: 6
```

Lys Ala Ser Gln Asn Val Gly Thr Asn Val Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: human monoclonal antibody VL CDR

<400> SEQUENCE: 7

Ser Thr Ser Tyr Arg Tyr Ser
1               5

<210> SEQ ID NO 8
<211> LENGTH: 9
<212> TYPE: PRT
<213> ORGANISM: Artificial Sequence
<220> FEATURE:
<223> OTHER INFORMATION: human monoclonal antibody VL CDR

<400> SEQUENCE: 8

Gln Gln Tyr Asn Ser Tyr Pro Tyr Thr
1               5

<210> SEQ ID NO 9
<211> LENGTH: 357
<212> TYPE: DNA
<213> ORGANISM: Artificial Sequence
<220> FEATURE:
<223> OTHER INFORMATION: human monoclonal antibody VH

<400> SEQUENCE: 9
gaggtgcagc tgcagcagtc aggggcggag cttgtgaagc caggggcctc agtcaagttg      60
tcctgtacag cttctggctt caacattaaa gacacctata tgcactgggt gaagcagagg     120
cctgaacagg gcctggagtg gattggaagg attgatcctg cgaatggtaa cactaaatat     180
gacccgaagt tccagggcaa ggccactata atagcagaca catcctccaa cacagcctac     240
ctgcagctca gcagcctgac atctgaggac actgccgtct attactgtgc taggggggtc     300
taccatgatt acgacgggga ctactggggc caaggaccac cgctcaccgt ctcctcc       357

<210> SEQ ID NO 10
<211> LENGTH: 321
<212> TYPE: DNA
<213> ORGANISM: Artificial Sequence
<220> FEATURE:
<223> OTHER INFORMATION: human monoclonal antibody VL

<400> SEQUENCE: 10
gacatcgtca tgacccagtc tcaaaaattc atgtccacat cagtaggaga cagggtcagc      60
gtcacctgca aggccagtca gaatgtgggt actaatgtag cctggtatca acagaaacca     120
gggcaatctc ctaaagcact gatttactcg acatcctacc ggtacagtgg agtccctgat     180
cgcttcacag gcagtggatc tgggacagat ttcactctca ccatcagcaa tgtgcagtct     240
gaagacttgg cagagtattt ctgtcagcaa tataacagct atccgtacac gttcggaggg     300
gggaccaagc tggaaataaa g                                               321

<210> SEQ ID NO 11
<211> LENGTH: 1200
<212> TYPE: DNA
<213> ORGANISM: Artificial Sequence
<220> FEATURE:

```
<223> OTHER INFORMATION: human monoclonal antibody VH DNA in pHCMV-
      Gamm1-neo expression vector
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (947)..(947)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1009)..(1009)
<223> OTHER INFORMATION: n is a, c, g, or t
<220> FEATURE:
<221> NAME/KEY: misc_feature
<222> LOCATION: (1027)..(1027)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1036)..(1036)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1099)..(1100)
<223> OTHER INFORMATION: n is a, c, g, or t
<220> FEATURE:
<221> NAME/KEY: misc_feature
<222> LOCATION: (1105)..(1105)
<223> OTHER INFORMATION: n is a, c, g, or t
<220> FEATURE:
<221> NAME/KEY: misc_feature
<222> LOCATION: (1108)..(1108)
<223> OTHER INFORMATION: n is a, c, g, or t
<220> FEATURE:
<221> NAME/KEY: misc_feature
<222> LOCATION: (1111)..(1111)
<223> OTHER INFORMATION: n is a, c, g, or t
<220> FEATURE:
<221> NAME/KEY: misc_feature
<222> LOCATION: (1127)..(1127)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1157)..(1157)
<223> OTHER INFORMATION: n is a, c, g, or t
<220> FEATURE:
```

<221> NAME/KEY: misc_feature
<222> LOCATION: (1168)..(1168)
<223> OTHER INFORMATION: n is a, c, g, or t
<220> FEATURE:
<221> NAME/KEY: misc_feature
<222> LOCATION: (1172)..(1172)
<223> OTHER INFORMATION: n is a, c, g, or t
<220> FEATURE:
<221> NAME/KEY: misc_feature
<222> LOCATION: (1190)..(1190)
<223> OTHER INFORMATION: n is a, c, g, or t

<400> SEQUENCE: 11

```
caggacgatc ngcctccgca agcttatgaa tatgcaaatc tctctgaatct acatggtaaa      60
tataggtttg tctataccac aaacagaaaa acatgagatc acagttctct ctacagttac     120
tgagcacaca ggacctcacc atgggatgga gctgtatcat cctcttcttg gtagcaacag     180
ctacaggtaa ggggctcaca gtagcaggct tgaggtctgg acatatatat gggtgacaat     240
gacatccact ttgcctttct ctccacaggt gtgcactccg aggtgcagct gcagcagtca     300
ggggcggagc ttgtgaagcc aggggcctca gtcaagttgt cctgtacagc ttctggcttc     360
aacattaaag acacctatat gcactgggtg aagcagaggc ctgaacaggg cctggagtgg     420
attggaagga ttgatcctgc gaatggtaac actaaatatg acccgaagtt ccagggcaag     480
gccactataa tagcagacac atcctccaac acagcctacc tgcagctcag cagcctgaca     540
tctgaggaca ctgccgtcta ttactgtgct agggggggtct accatgatta cgacggggac     600
tactggggcc aagggaccac gctcaccgtc tcctccggtg agtggatccc aagctagctt     660
tctggggcag gccaggcctg accttggctt tggggcaggg aggggctaa ggtgaggcag     720
gtggcgccag ccaggtgcac acccaatgcc catgagccca gacactggac gctgaacctc     780
gcggacagtt aagaacccag gggcctctgc gccctgggcc cagctctgtc ccacaccgcg     840
gtcacatggc accacctctc ttgcagcctc caccaagggc ccatcggtct tccccctggc     900
accccctcctc caagagcacc tctggggca cagcggccct gggctgncct ggtcaaggac     960
tacttccccc gaaccggtga cggtgtcgtg gaactcangc gccctgacna gcggggtgca    1020
caccttnccg gntgtnctac agtnctcagg actctactcc ctcancagcg tggtgaccgt    1080
gcccntcagc agctngggnn cccanacnta natttgcacg ggaatcnaag cccngnaacc    1140
caagggaaa aaaaaanttg gtgaaagncc cnccagggag ggaggggttn tgctggaaac    1200
```

<210> SEQ ID NO 12
<211> LENGTH: 1121
<212> TYPE: DNA
<213> ORGANISM: Artificial Sequence
<220> FEATURE:
<223> OTHER INFORMATION: human monoclonal antibody VL DNA in pHCMV-Gamm1-neo expression vector
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (983)..(983)
<223> OTHER INFORMATION: n is a, c, g, or t
<220> FEATURE:
<221> NAME/KEY: misc_feature
<222> LOCATION: (1002)..(1003)
<223> OTHER INFORMATION: n is a, c, g, or t
<220> FEATURE:

<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1055)..(1055)
<223> OTHER INFORMATION: n is a, c, g, or t
<220> FEATURE:
<221> NAME/KEY: misc_feature
<222> LOCATION: (1057)..(1057)
<223> OTHER INFORMATION: n is a, c, g, or t
<220> FEATURE:
<221> NAME/KEY: misc_feature
<222> LOCATION: (1084)..(1084)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1121)..(1121)
<223> OTHER INFORMATION: n is a, c, g, or t

<400> SEQUENCE: 12

```
ncagggcgat cngcctccgc aagcttatga atatgcaaat cctctgaatc tacatggtaa      60
atataggttt gtctatacca caaacagaaa aacatgagat cacagttctc tctacagtta     120
ctgagcacac aggacctcac catgggatgg agctgtatca tcctcttctt ggtagcaaca     180
gctacaggta aggggctcac agtagcaggc ttgaggtctg acatatata tgggtgacaa      240
tgacatccac tttgccttc tctccacagg tgtgcactcc gacatcgtca tgacccagtc     300
tcaaaaattc atgtccacat cagtaggaga cagggtcagc gtcacctgca aggccagtca     360
gaatgtgggt actaatgtag cctggtatca acagaaacca gggcaatctc ctaaagcact     420
gatttactcg acatcctacc ggtacagtgg agtccctgat cgcttcacag gcagtggatc     480
tgggacagat ttcactctca ccatcagcaa tgtgcagtct gaagacttgg cagagtattt     540
ctgtcagcaa tataacagct atccgtacac gttcggaggg gggaccaagc tggaaataaa     600
gggtgagtgg atcctagaat ctaaactct gaggggtcg gatgacgtgg ccattctttg      660
cctaaagcat tgagtttact gcaaggtcag aaaagcatgc aaagccctca gaatggctgc     720
aaagagctcc aacaaaacaa tttagaactt tattaaggaa tagggggaag ctaggaagaa     780
actcaaaaca tcaagatttt aaatacgctt cttggtctcc ttgctataat tatctgggat     840
aagcatgctg ttttctgtct gtccctaaca tgccctgtga ttatccgcaa acaacacacc     900
caagggcaga actttgttac ttaaacacca tcctgtttgc ttctttcctc aggaactgtg     960
gctgcaccat ctgtcttcat ctncccgcca tctgatgagc anntgaaatc tggnaactgc    1020
ctctgttgtg tgcctgctga aaaacttcta tcccnanagg ccaaagtaca gtggaagggg    1080
aaancccct cnatcggnaa ctcccggaan ggncccganc n                         1121
```

<210> SEQ ID NO 13
<211> LENGTH: 15
<212> TYPE: DNA
<213> ORGANISM: Artificial Sequence
<220> FEATURE:
<223> OTHER INFORMATION: human monoclonal antibody VH CDR

<400> SEQUENCE: 13
gacacctata tgcac                                                15

<210> SEQ ID NO 14
<211> LENGTH: 51
<212> TYPE: DNA
<213> ORGANISM: Artificial Sequence
<220> FEATURE:
<223> OTHER INFORMATION: human monoclonal antibody VH CDR

<400> SEQUENCE: 14
aggattgatc ctgcgaatgg taacactaaa tatgacccga agttccaggg c         51

<210> SEQ ID NO 15
<211> LENGTH: 30
<212> TYPE: DNA
<213> ORGANISM: Artificial Sequence
<220> FEATURE:
<223> OTHER INFORMATION: human monoclonal antibody VH CDR

<400> SEQUENCE: 15
ggggtctacc atgattacga cggggactac                                30

<210> SEQ ID NO 16
<211> LENGTH: 33
<212> TYPE: DNA
<213> ORGANISM: Artificial Sequence
<220> FEATURE:
<223> OTHER INFORMATION: human monoclonal antibody VL CDR

<400> SEQUENCE: 16
aaggccagtc agaatgtggg tactaatgta gcc                            33

<210> SEQ ID NO 17
<211> LENGTH: 21
<212> TYPE: DNA
<213> ORGANISM: Artificial Sequence
<220> FEATURE:
<223> OTHER INFORMATION: human monoclonal antibody VL CDR

<400> SEQUENCE: 17
tcgacatcct accggtacag t                                         21

<210> SEQ ID NO 18
<211> LENGTH: 27
<212> TYPE: DNA
<213> ORGANISM: Artificial Sequence
<220> FEATURE:
<223> OTHER INFORMATION: human monoclonal antibody VL CDR

<400> SEQUENCE: 18
cagcaatata acagctatcc gtacacg                                   27

<210> SEQ ID NO 19
<211> LENGTH: 530
<212> TYPE: PRT
<213> ORGANISM: Artificial Sequence
<220> FEATURE:

<223> OTHER INFORMATION: Flexi-IL12

<400> SEQUENCE: 19

```
Met Cys His Gln Gln Leu Val Ile Ser Trp Phe Ser Leu Val Phe Leu
 1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Ser Gly Gly Gly
                325                 330                 335

Gly Ser Gly Gly Gly Ser Arg Asn Leu Pro Val Ala Thr Pro Asp
            340                 345                 350

Pro Gly Met Phe Pro Cys Leu His His Ser Gln Asn Leu Leu Arg Ala
        355                 360                 365

Val Ser Asn Met Leu Gln Lys Ala Arg Gln Thr Leu Glu Phe Tyr Pro
    370                 375                 380

Cys Thr Ser Glu Glu Ile Asp His Glu Asp Ile Thr Lys Asp Lys Thr
385                 390                 395                 400
```

```
Ser Thr Val Glu Ala Cys Leu Pro Leu Glu Leu Thr Lys Asn Glu Ser
                405                 410                 415
Cys Leu Asn Ser Arg Glu Thr Ser Phe Ile Thr Asn Gly Ser Cys Leu
            420                 425                 430
Ala Ser Arg Lys Thr Ser Phe Met Met Ala Leu Cys Leu Ser Ser Ile
        435                 440                 445
Tyr Glu Asp Leu Lys Met Tyr Gln Val Glu Phe Lys Thr Met Asn Ala
    450                 455                 460
Lys Leu Leu Met Asp Pro Lys Arg Gln Ile Phe Leu Asp Gln Asn Met
465                 470                 475                 480
Leu Ala Val Ile Asp Glu Leu Met Gln Ala Leu Asn Phe Asn Ser Glu
                485                 490                 495
Thr Val Pro Gln Lys Ser Ser Leu Glu Glu Pro Asp Phe Tyr Lys Ala
            500                 505                 510
Phe Arg Ile Arg Ala Val Thr Ile Asp Arg Val Met Ser Tyr Leu Asn
        515                 520                 525
Ala Ser
    530

<210> SEQ ID NO 20
<211> LENGTH: 21
<212> TYPE: PRT
<213> ORGANISM: Artificial Sequence
<220> FEATURE:
<223> OTHER INFORMATION: IgG heavy chain leader component of KM.CAR-
      hCH2CH3-28z construct

<400> SEQUENCE: 20

Met Glu Phe Gly Leu Ser Trp Leu Phe Leu Val Ala Ile Leu Lys Gly
1               5                   10                  15
Val Gln Cys Ser Arg
            20

<210> SEQ ID NO 21
<211> LENGTH: 107
<212> TYPE: PRT
<213> ORGANISM: Artificial Sequence
<220> FEATURE:
<223> OTHER INFORMATION: KappaMab variable light chain component of
      KM.CAR-hCH2CH3-28z construct

<400> SEQUENCE: 21

Asp Ile Val Met Thr Gln Ser Gln Lys Phe Met Ser Thr Ser Val Gly
1               5                   10                  15
Asp Arg Val Ser Val Thr Cys Lys Ala Ser Gln Asn Val Gly Thr Asn
            20                  25                  30
Val Ala Trp Tyr Gln Gln Lys Pro Gly Gln Ser Pro Lys Ala Leu Ile
        35                  40                  45
Tyr Ser Thr Ser Tyr Arg Tyr Ser Gly Val Pro Asp Arg Phe Thr Gly
    50                  55                  60
Ser Gly Ser Gly Thr Asp Phe Thr Leu Thr Ile Ser Asn Val Gln Ser
65                  70                  75                  80
Glu Asp Leu Ala Glu Tyr Phe Cys Gln Gln Tyr Asn Ser Tyr Pro Tyr
                85                  90                  95
Thr Phe Gly Gly Gly Thr Lys Leu Glu Ile Lys
            100                 105

<210> SEQ ID NO 22
<211> LENGTH: 125
```

```
<212> TYPE: PRT
<213> ORGANISM: Artificial Sequence
<220> FEATURE:
<223> OTHER INFORMATION: KappaMab variable heavy chain component of
      KM.CAR-hCH2CH3-28z construct

<400> SEQUENCE: 22
```

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Ile Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Val Tyr His Asp Tyr Asp Gly Asp Tyr Trp Gly Gln Gly
            100                 105                 110

Thr Thr Leu Thr Val Ser Ser Tyr Val Thr Val Ser Ser
            115                 120                 125

```
<210> SEQ ID NO 23
<211> LENGTH: 15
<212> TYPE: PRT
<213> ORGANISM: Artificial Sequence
<220> FEATURE:
<223> OTHER INFORMATION: (G4S)3 flexible linker component of KM.CAR-
      hCH2CH3-28z construct

<400> SEQUENCE: 23
```

Gly Gly Gly Gly Ser Gly Gly Gly Gly Ser Gly Gly Gly Gly Ser
1               5                   10                  15

```
<210> SEQ ID NO 24
<211> LENGTH: 246
<212> TYPE: PRT
<213> ORGANISM: Artificial Sequence
<220> FEATURE:
<223> OTHER INFORMATION: Hinge, CH2 and CH3 components of KM.CAR-
      hCH2CH3-28z construct

<400> SEQUENCE: 24
```

Tyr Val Thr Val Ser Ser Gln Asp Pro Ala Glu Pro Lys Ser Pro Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu

```
            115                 120                 125
Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys Lys Asp Pro Lys
                245

<210> SEQ ID NO 25
<211> LENGTH: 68
<212> TYPE: PRT
<213> ORGANISM: Homo sapiens

<400> SEQUENCE: 25

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 26
<211> LENGTH: 112
<212> TYPE: PRT
<213> ORGANISM: Homo sapiens

<400> SEQUENCE: 26

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
        100                 105                 110
```

<210> SEQ ID NO 27
<211> LENGTH: 688
<212> TYPE: PRT
<213> ORGANISM: Artificial Sequence
<220> FEATURE:
<223> OTHER INFORMATION: Full length KM.CAR-hCH2CH3-28z amino acid construct

<400> SEQUENCE: 27

```
Met Glu Phe Gly Leu Ser Trp Leu Phe Leu Val Ala Ile Leu Lys Gly
1               5                   10                  15

Val Gln Cys Ser Arg Asp Ile Val Met Thr Gln Ser Gln Lys Phe Met
            20                  25                  30

Ser Thr Ser Val Gly Asp Arg Val Ser Val Thr Cys Lys Ala Ser Gln
        35                  40                  45

Asn Val Gly Thr Asn Val Ala Trp Tyr Gln Gln Lys Pro Gly Gln Ser
    50                  55                  60

Pro Lys Ala Leu Ile Tyr Ser Thr Ser Tyr Arg Tyr Ser Gly Val Pro
65                  70                  75                  80

Asp Arg Phe Thr Gly Ser Gly Ser Gly Thr Asp Phe Thr Leu Thr Ile
                85                  90                  95

Ser Asn Val Gln Ser Glu Asp Leu Ala Glu Tyr Phe Cys Gln Gln Tyr
            100                 105                 110

Asn Ser Tyr Pro Tyr Thr Phe Gly Gly Gly Thr Lys Leu Glu Ile Lys
        115                 120                 125

Gly Gly Gly Gly Ser Gly Gly Gly Gly Ser Gly Gly Gly Gly Ser Glu
    130                 135                 140

Val Gln Leu Gln Gln Ser Gly Ala Glu Leu Val Lys Pro Gly Ala Ser
145                 150                 155                 160

Val Lys Leu Ser Cys Thr Ala Ser Gly Phe Asn Ile Lys Asp Thr Tyr
                165                 170                 175

Met His Trp Val Lys Gln Arg Pro Glu Gln Gly Leu Glu Trp Ile Gly
            180                 185                 190

Arg Ile Asp Pro Ala Asn Gly Asn Thr Lys Tyr Asp Pro Lys Phe Gln
        195                 200                 205

Gly Lys Ala Thr Ile Ile Ala Asp Thr Ser Ser Asn Thr Ala Tyr Leu
    210                 215                 220

Gln Leu Ser Ser Leu Thr Ser Glu Asp Thr Ala Val Tyr Tyr Cys Ala
225                 230                 235                 240

Arg Gly Val Tyr His Asp Tyr Asp Gly Asp Tyr Trp Gly Gln Gly Thr
                245                 250                 255

Thr Leu Thr Val Ser Ser Tyr Val Thr Val Ser Ser Gln Asp Pro Ala
            260                 265                 270

Glu Pro Lys Ser Pro Asp Lys Thr His Thr Cys Pro Pro Cys Pro Ala
        275                 280                 285

Pro Glu Leu Leu Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365
```

| | | | | | | | | | | | |
|---|---|---|---|---|---|---|---|---|---|---|---|
|Asp|Trp|Leu|Asn|Gly|Lys|Glu|Tyr|Lys|Cys|Lys|Val|Ser|Asn|Lys|Ala|
| |370| | | |375| | | |380| | | | | | |

Asp Trp Leu Asn Gly Lys Glu Tyr Lys Cys Lys Val Ser Asn Lys Ala
    370             375             380

Leu Pro Ala Pro Ile Glu Lys Thr Ile Ser Lys Ala Lys Gly Gln Pro
385             390             395             400

Arg Glu Pro Gln Val Tyr Thr Leu Pro Pro Ser Arg Asp Glu Leu Thr
            405             410             415

Lys Asn Gln Val Ser Leu Thr Cys Leu Val Lys Gly Phe Tyr Pro Ser
        420             425             430

Asp Ile Ala Val Glu Trp Glu Ser Asn Gly Gln Pro Glu Asn Asn Tyr
            435             440             445

Lys Thr Thr Pro Pro Val Leu Asp Ser Asp Gly Ser Phe Phe Leu Tyr
450             455             460

Ser Lys Leu Thr Val Asp Lys Ser Arg Trp Gln Gln Gly Asn Val Phe
465             470             475             480

Ser Cys Ser Val Met His Glu Ala Leu His Asn His Tyr Thr Gln Lys
            485             490             495

Ser Leu Ser Leu Ser Pro Gly Lys Lys Asp Pro Lys Phe Trp Val Leu
        500             505             510

Val Val Val Gly Gly Val Leu Ala Cys Tyr Ser Leu Leu Val Thr Val
        515             520             525

Ala Phe Ile Ile Phe Trp Val Arg Ser Lys Arg Ser Arg Leu Leu His
530             535             540

Ser Asp Tyr Met Asn Met Thr Pro Arg Arg Pro Gly Pro Thr Arg Lys
545             550             555             560

His Tyr Gln Pro Tyr Ala Pro Pro Arg Asp Phe Ala Ala Tyr Arg Ser
            565             570             575

Arg Val Lys Phe Ser Arg Ser Ala Asp Ala Pro Ala Tyr Gln Gln Gly
        580             585             590

Gln Asn Gln Leu Tyr Asn Glu Leu Asn Leu Gly Arg Arg Glu Glu Tyr
        595             600             605

Asp Val Leu Asp Lys Arg Arg Gly Arg Asp Pro Glu Met Gly Gly Lys
    610             615             620

Pro Arg Arg Lys Asn Pro Gln Glu Gly Leu Tyr Asn Glu Leu Gln Lys
625             630             635             640

Asp Lys Met Ala Glu Ala Tyr Ser Glu Ile Gly Met Lys Gly Glu Arg
            645             650             655

Arg Arg Gly Lys Gly His Asp Gly Leu Tyr Gln Gly Leu Ser Thr Ala
        660             665             670

Thr Lys Asp Thr Tyr Asp Ala Leu His Met Gln Ala Leu Pro Pro Arg
    675             680             685

<210> SEQ ID NO 28
<211> LENGTH: 2064
<212> TYPE: DNA
<213> ORGANISM: Artificial Sequence
<220> FEATURE:
<223> OTHER INFORMATION: Full length KM.CAR-hCH2CH3-28z nucleic acid
      construct

<400> SEQUENCE: 28
atggagtttg ggctgagctg cttttttctt gtggctattt taaaaggtgt ccagtgctct      60
agagacatcg tcatgaccca gtctcaaaaa ttcatgtcca catcagtagg agacagggtc    120
agcgtcacct gcaaggccag tcagaatgtg gtactaatg tagcctggta tcaacagaaa    180
ccagggcaat ctcctaaagc actgatttac tcgacatcct accggtacag tggagtccct    240

```
gatcgcttca caggcagtgg atctgggaca gatttcactc tcaccatcag caatgtgcag      300
tctgaagact tggcagagta tttctgtcag caatataaca gctatccgta cacgttcgga      360
ggggggacca agctggaaat aaagggtggc ggtggctcgg gcggtggtgg gtcgggtggc      420
ggcggatctg aggtgcagct gcagcagtca ggggcggagc ttgtgaagcc agggggcctca     480 gtcaagttgt cctgtacagc ttctggcttc aacattaaag acacctatat gcactgggtg      540
aagcagaggc ctgaacaggg cctggagtgg attggaagga ttgatcctgc aatggtaac      600 actaaatatg acccgaagtt ccagggcaag gccactataa tagcagacac atcctccaac      660
acagcctacc tgcagctcag cagcctgaca tctgaggaca ctgccgtcta ttactgtgct      720 agggggtct accatgatta cgacggggac tactggggcc aagggaccac gctcaccgtc      780
tcctcctacg tcaccgtctc ttcacaggat cccgccgagc ccaaatctcc tgacaaaact      840
cacacatgcc caccgtgccc agcacctgaa ctcctggggg gaccgtcagt cttcctcttc      900
cccccaaaac ccaaggacac cctcatgatc tcccggaccc ctgaggtcac atgcgtggtg      960
gtggacgtga gccacgaaga ccctgaggtc aagttcaact ggtacgtgga cggcgtggag     1020
gtgcataatg ccaagacaaa gccgcgggag gagcagtaca acagcacgta ccgtgtggtc     1080
agcgtcctca ccgtcctgca ccaggactgg ctgaatggca aggagtacaa gtgcaaggtc     1140
tccaacaaag ccctcccagc ccccatcgag aaaaccatct ccaaagccaa agggcagccc     1200
cgagaaccac aggtgtacac cctgccccca tcccgggatg agctgaccaa gaaccaggtc     1260
agcctgacct gcctggtcaa aggcttctat cccagcgaca tcgccgtgga gtgggagagc     1320
aatgggcaac cggagaacaa ctacaagacc acgcctcccg tgctggactc cgacggctcc     1380
ttcttcctct acagcaagct caccgtggac aagagcaggt ggcagcaggg gaacgtcttc     1440
tcatgctccg tgatgcatga ggctctgcac aaccactaca cgcagaagag cctctccctg     1500
tctccgggta aaaaagatcc caaattttgg gtgctggtgg tggttggtgg agtcctggct     1560
tgctatagct tgctagtaac agtggccttt attattttct gggtgaggag taagaggagc     1620
aggctcctgc acagtgacta catgaacatg actccccgcc gccccgggcc cacccgcaag     1680
cattaccagc cctatgcccc accacgcgac ttcgcagcct atcgctccag agtgaagttc     1740
agcaggagcg cagacgcccc cgcgtaccag cagggccaga accagctcta taacgagctc     1800
aatctaggac gaagagagga gtacgatgtt ttggacaaga cgtggccg ggaccctgag      1860 atgggggaa agccgagaag gaagaaccct caggaaggcc tgtacaatga actgcagaaa     1920
gataagatgg cggaggccta cagtgagatt gggatgaaag cgagcgccg gaggggcaag     1980 gggcacgatg gcctttacca gggtctcagt acagccacca aggacaccta cgacgccctt     2040
cacatgcagg ccctgccccc tcgc                                            2064
```

<210> SEQ ID NO 29
<211> LENGTH: 1727
<212> TYPE: DNA
<213> ORGANISM: Artificial Sequence
<220> FEATURE:
<223> OTHER INFORMATION: Full length KM.CAR-hCH3-28z nucleic acid
      construct

<400> SEQUENCE: 29

```
tggagtttgg gctgagctgg cttttctctg tggctatttt aaaaggtgtc cagtgctcta       60
gagacatcgt catgacccag tctcaaaaat tcatgtccac atcagtagga gacagggtca      120
gcgtcacctg caaggccagt cagaatgtgg gtactaatgt agcctggtat caacagaaac      180
```

```
caggqcaatc tcctaaagca ctgatttact cgacatccta ccggtacagt ggagtccctg    240
atcgcttcac aggcagtgga tctgggacag atttcactct caccatcagc aatgtgcagt    300
ctgaagactt ggcagagtat ttctgtcagc aatataacag ctatccgtac acgttcggag    360
gggggaccaa gctggaaata aagggtggcg gtggctcggg cggtggtggg tcgggtggcg    420
gcggatctga ggtgcagctg cagcagtcag gggcggagct tgtgaagcca ggggcctcag    480
tcaagttgtc ctgtacagct tctggcttca acattaaaga cacctatatg cactgggtga    540
agcagaggcc tgaacagggc ctggagtgga ttggaaggat tgatcctgcg aatggtaaca    600
ctaaatatga cccgaagttc cagggcaagg ccactataat agcagacaca tcctccaaca    660
cagcctacct gcagctcagc agcctgacat ctgaggacac tgccgtctat tactgtgcta    720 gggggggtcta ccatgattac gacgggggact actggggcca aggaccacg ctcaccgtct    780 cctccggtgg aggcgggtct ggggggcggag gttcaggcgg gggtggttcc gagcccaaat    840
ctcctgacaa aactcacaca tgcccagggc agccccgaga accacaggtg tacaccctgc    900
ccccatcccg ggatgagctg accaagaacc aggtcagcct gacctgcctg gtcaaaggct    960
tctatcccag cgacatcgcc gtggagtggg agagcaatgg gcagccggag aacaactaca    1020
agaccacgcc tcccgtgctg gactccgacg gctccttctt cctctacagc aagctcaccg    1080
tggacaagag caggtggcag caggggaacg tcttctcatg ctccgtgatg catgaggctc    1140
tgcacaacca ctacacacag aagagcctct ccctgtctcc gggtaaattt tgggtgctgg    1200
tggtggttgg tggagtcctg gcttgctata gcttgctagt aacagtggcc tttattattt    1260
tctgggtgag gagtaagagg agcaggctcc tgcacagtga ctacatgaac atgactcccc    1320
gccgccccgg gcccacccgc aagcattacc agccctatgc cccaccacgc gacttcgcag    1380
cctatcgctc cagagtgaag ttcagcagga gcgcagacgc ccccgcgtac cagcagggcc    1440
agaaccagct ctataacgag ctcaatctag gacgaagaga ggagtacgat gttttggaca    1500
agagacgtgg ccgggaccct gagatggggg gaaagccgag aaggaagaac cctcaggaag    1560
gcctgtacaa tgaactgcag aaagataaga tggcggaggc ctacagtgag attgggatga    1620
aaggcgagcg ccggaggggc aaggggcacg atggccttta ccagggtctc agtacagcca    1680
ccaaggacac ctacgacgcc cttcacatgc aggccctgcc ccctcgc                 1727
```

<210> SEQ ID NO 30
<211> LENGTH: 1407
<212> TYPE: DNA
<213> ORGANISM: Artificial Sequence
<220> FEATURE:
<223> OTHER INFORMATION: Full length KM.CAR-h-28z nucleic acid construct

<400> SEQUENCE: 30

```
atggagtttg ggctgagctg gcttttctct gtggctattt taaaaggtgt ccagtgctct    60
agagacatcg tcatgaccca gtctcaaaaa ttcatgtcca catcagtagg agacagggtc    120
agcgtcacct gcaaggccag tcagaatgtg gtactaatg tagcctggta tcaacagaaa    180
ccagggcaat ctcctaaagc actgatttac tcgacatcct accggtacag tggagtccct    240
gatcgcttca caggcagtgg atctgggaca gatttcactc tcaccatcag caatgtgcag    300
tctgaagact tggcagagta tttctgtcag caatataaca gctatccgta cacgttcgga    360
ggggggacca agctggaaat aaagggtggc ggtggctcgg gcggtggtgg gtcgggtggc    420
ggcggatctg aggtgcagct gcagcagtca ggggcggagc ttgtgaagcc aggggcctca    480
gtcaagttgt cctgtacagc ttctggcttc aacattaaag cacctatat gcactgggtg    540
```

```
aagcagaggc ctgaacaggg cctggagtgg attggaagga ttgatcctgc gaatggtaac      600
actaaatatg acccgaagtt ccagggcaag gccactataa tagcagacac atcctccaac      660
acagcctacc tgcagctcag cagcctgaca tctgaggaca ctgccgtcta ttactgtgct      720 agggggtct accatgatta cgacggggac tactggggcc aagggaccac gctcaccgtc      780
tcctccggtg gaggcgggtc tggggcgga ggttcaggcg ggggtggttc cgagcccaaa      840
tctcctgaca aaactcacac atgcccattt ggggtgctgg tggtggttgg tggagtcctg      900
gcttgctata gcttgctagt aacagtggcc tttattattt tctgggtgag gagtaagagg      960
agcaggctcc tgcacagtga ctacatgaac atgactcccc gccgcccgg gcccacccgc     1020 aagcattacc agccctatgc cccaccacgc gacttcgcag cctatcgctc cagagtgaag     1080
ttcagcagga gcgcagacgc ccccgcgtac cagcagggcc agaaccagct ctataacgag     1140
ctcaatctag gacgaagaga ggagtacgat gttttggaca gagacgtggc cgggaccct     1200 gagatggggg gaaagccgag aaggaagaac cctcaggaag gcctgtacaa tgaactgcag     1260
aaagataaga tggcggaggc ctacagtgag attgggatga aggcgagcg ccggaggggc     1320 aaggggcacg atggccttta ccagggtctc agtacagcca ccaaggacac ctacgacgcc     1380
cttcacatgc aggccctgcc ccctcgc                                        1407

<210> SEQ ID NO 31
<211> LENGTH: 1461
<212> TYPE: DNA
<213> ORGANISM: Artificial Sequence
<220> FEATURE:
<223> OTHER INFORMATION: Full length KM.CAR-CD8a-28z nucleic acid
      construct

<400> SEQUENCE: 31
atggagtttg gctgagctg cttttctt gtggctattt taaaaggtgt ccagtgctct       60
agagacatcg tcatgaccca gtctcaaaaa ttcatgtcca catcagtagg agacagggtc      120
agcgtcacct gcaaggccag tcagaatgtg gtactaatg tagcctggta tcaacagaaa      180
ccagggcaat tcctaaagc actgatttac tcgacatcct accggtacag tggagtccct      240
gatcgcttca caggcagtgg atctgggaca gatttcactc tcaccatcag caatgtgcag      300
tctgaagact tggcagagta tttctgtcag caatataaca gctatccgta cacgttcgga      360 gggggacca agctggaaat aaagggtggc ggtggctcgg gcggtggtgg gtcgggtggc      420
ggcggatctg aggtgcagct gcagcagtca ggggcggagc ttgtgaagcc aggggcctca      480
gtcaagttgt cctgtacagc ttctggcttc aacattaaag acacctatat gcactgggtg      540
aagcagaggc ctgaacaggg cctggagtgg attggaagga ttgatcctgc gaatggtaac      600
actaaatatg acccgaagtt ccagggcaag gccactataa tagcagacac atcctccaac      660
acagcctacc tgcagctcag cagcctgaca tctgaggaca ctgccgtcta ttactgtgct      720 agggggtct accatgatta cgacggggac tactggggcc aagggaccac gctcaccgtc      780
tcctccacca cgacgccagc gccgcgacca ccaacaccgg cgcccaccat cgcgtcgcag      840
cccctgtccc tgcgcccaga ggcgtgccgg ccagcggcgg ggggcgcagt gcacacgagg      900
gggctggact tcgcctgtga tttttgggtg ctggtggtgg ttggtggagt cctggcttgc      960
tatagcttgc tagtaacagt ggcctttatt attttctggg tgaggagtaa gaggagcagg     1020
ctcctgcaca gtgactacat gaacatgact ccccgccgcc cgggcccac cgcaagcat      1080 taccagccct atgccccacc acgcgacttc gcagcctatc gctccagagt gaagttcagc     1140
```

```
aggagcgcag acgccccgc gtaccagcag ggccagaacc agctctataa cgagctcaat    1200
ctaggacgaa gagaggagta cgatgttttg acaagagagt gtggccggga ccctgagatg    1260
gggggaaagc cgagaaggaa gaaccctcag gaaggcctgt acaatgaact gcagaaagat    1320
aagatggcgg aggcctacag tgagattggg atgaaaggcg agcgccggag gggcaagggg    1380
cacgatggcc tttaccaggg tctcagtaca gccaccaagg acacctacga cgcccttcac    1440
atgcaggccc tgcccctcg c                                              1461
```

<210> SEQ ID NO 32
<211> LENGTH: 1410
<212> TYPE: DNA
<213> ORGANISM: Artificial Sequence
<220> FEATURE:
<223> OTHER INFORMATION: Full length KM.CAR-h-28TM-41BBz nucleic acid construct

<400> SEQUENCE: 32

```
atggagtttg gctgagctg gcttttctt gtggctattt taaaaggtgt ccagtgctct        60
agagacatcg tcatgaccca gtctcaaaaa ttcatgtcca catcagtagg agacagggtc     120
agcgtcacct gcaaggccag tcagaatgtg gtactaatg tagcctggta tcaacagaaa     180
ccagggcaat ctcctaaagc actgatttac tcgacatcct accggtacag tggagtccct     240
gatcgcttca caggcagtgg atctgggaca gatttcactc tcaccatcag caatgtgcag     300
tctgaagact tggcagagta tttctgtcag caatataaca gctatccgta cacgttcgga     360
ggggggacca agctggaaat aaagggtggc ggtggctcgg cggtggtgg gtcgggtggc     420 ggcggatctg aggtgcagct gcagcagtca ggggcggagc ttgtgaagcc aggggcctca     480
gtcaagttgt cctgtacagc ttctggcttc aacattaaag acacctatat gcactgggtg     540
aagcagaggc ctgaacaggg cctggagtgg attggaagga ttgatcctgc aaatggtaac     600
actaaatatg acccgaagtt ccagggcaag gccactataa tagcagacac atcctccaac     660
acagcctacc tgcagctcag cagcctgaca tctgaggaca ctgccgtcta ttactgtgct     720 agggggtct accatgatta cgacgggac tactggggcc aagggaccac gctcaccgtc     780
tcctccggtg gaggcgggtc tgggggcgga ggttcaggcg ggggtggttc cgagcccaaa     840
tctcctgaca aaactcacac atgcccattt tgggtgctgg tggtggttgg tggagtcctg     900
gcttgctata gcttgctagt aacagtggcc tttattattt tctgggtgaa acggggcaga     960
aagaaactcc tgtatatatt caaacaacca tttatgagac cagtacaaac tactcaagag    1020
gaagatggct gtagctgccg atttccagaa gaagaagaag aggatgtga actgagagtg    1080 aagttcagca ggagcgcaga cgccccgcg taccagcagg gccagaacca gctctataac    1140
gagctcaatc taggacgaag agaggagtac gatgttttgg acaagagacg tggccgggac    1200
cctgagatgg ggggaaagcc gagaaggaag aaccctcagg aaggcctgta caatgaactg    1260
cagaaagata gatggcgga ggcctacagt gagattggga tgaaaggcga gcgccggagg    1320 ggcaagggc acgatggcct ttaccagggt ctcagtacag ccaccaagga cacctacgac    1380
gcccttcaca tgcaggccct gcccctcgc                                    1410
```

<210> SEQ ID NO 33
<211> LENGTH: 1464
<212> TYPE: DNA
<213> ORGANISM: Artificial Sequence
<220> FEATURE:
<223> OTHER INFORMATION: Full length KM.CAR_8a_28TM_41BBz nucleic acid

<400> SEQUENCE: 33

| | |
|---|---|
| atggagtttg ggctgagctg gcttttctt gtggctattt taaaaggtgt ccagtgctct | 60 |
| agagacatcg tcatgaccca gtctcaaaaa ttcatgtcca catcagtagg agacagggtc | 120 |
| agcgtcacct gcaaggccag tcagaatgtg ggtactaatg tagcctggta tcaacagaaa | 180 |
| ccagggcaat ctcctaaagc actgatttac tcgacatcct accggtacag tggagtccct | 240 |
| gatcgcttca caggcagtgg atctgggaca gatttcactc tcaccatcag caatgtgcag | 300 |
| tctgaagact ggcagagta tttctgtcag caatataaca gctatccgta cacgttcgga | 360 |
| ggggggacca agctggaaat aaagggtggc ggtggctcgg gcggtggtgg gtcgggtggc | 420 |
| ggcggatctg aggtgcagct gcagcagtca ggggcggagc ttgtgaagcc aggggcctca | 480 |
| gtcaagttgt cctgtacagc ttctggcttc aacattaaag acacctatat gcactgggtg | 540 |
| aagcagaggc ctgaacaggg cctggagtgg attggaagga ttgatcctgc gaatggtaac | 600 |
| actaaatatg acccgaagtt ccaggcaag gccactataa tagcagacac atcctccaac | 660 |
| acagcctacc tgcagctcag cagcctgaca tctgaggaca ctgccgtcta ttactgtgct | 720 |
| agggggtct accatgatta cgacggggac tactggggcc aagggaccac gctcaccgtc | 780 |
| tcctccacca cgacgccagc gccgcgacca ccaacaccgg cgccaccat cgcgtcgcag | 840 |
| cccctgtccc tgcgcccaga ggcgtgccgg ccagcggcgg ggggcgcagt gcacacgagg | 900 |
| gggctggact cgcctgtga ttttgggtg ctggtggtgg ttggtggagt cctggcttgc | 960 |
| tatagcttgc tagtaacagt ggcctttatt attttctggg tgaaacgggg cagaaagaaa | 1020 |
| ctcctgtata tattcaaaca accatttatg agaccagtac aaactactca agaggaagat | 1080 |
| ggctgtagct gccgatttcc agaagaagaa gaaggaggat gtgaactgag agtgaagttc | 1140 |
| agcaggagcg cagacgcccc cgcgtaccag cagggccaga accagctcta taacgagctc | 1200 |
| aatctaggac gaagagagga gtacgatgtt ttggacaaga cgtggccg ggaccctgag | 1260 |
| atgggggaa agccgagaag gaagaaccct caggaaggcc tgtacaatga actgcagaaa | 1320 |
| gataagatgg cggaggccta cagtgagatt gggatgaaag cgagcgccg gaggggcaag | 1380 |
| gggcacgatg gcctttacca gggtctcagt acagccacca aggacaccta cgacgccctt | 1440 |
| cacatgcagg ccctgccccc tcgc | 1464 |

<210> SEQ ID NO 34
<211> LENGTH: 2067
<212> TYPE: DNA
<213> ORGANISM: Artificial Sequence
<220> FEATURE:
<223> OTHER INFORMATION: Full length KM.CAR_hCH2CH3mut_28TM_41BBz nucleic acid construct

<400> SEQUENCE: 34

| | |
|---|---|
| atggagtttg ggctgagctg gcttttctt gtggctattt taaaaggtgt ccagtgctct | 60 |
| agagacatcg tcatgaccca gtctcaaaaa ttcatgtcca catcagtagg agacagggtc | 120 |
| agcgtcacct gcaaggccag tcagaatgtg ggtactaatg tagcctggta tcaacagaaa | 180 |
| ccagggcaat ctcctaaagc actgatttac tcgacatcct accggtacag tggagtccct | 240 |
| gatcgcttca caggcagtgg atctgggaca gatttcactc tcaccatcag caatgtgcag | 300 |
| tctgaagact ggcagagta tttctgtcag caatataaca gctatccgta cacgttcgga | 360 |
| ggggggacca agctggaaat aaagggtggc ggtggctcgg gcggtggtgg gtcgggtggc | 420 |

```
ggcggatctg aggtgcagct gcagcagtca ggggcggagc ttgtgaagcc aggggcctca    480
gtcaagttgt cctgtacagc ttctggcttc aacattaaag acacctatat gcactgggtg    540
aagcagaggc ctgaacaggg cctggagtgg attggaagga ttgatcctgc gaatggtaac    600
actaaatatg acccgaagtt ccagggcaag gccactataa tagcagacac atcctccaac    660
acagcctacc tgcagctcag cagcctgaca tctgaggaca ctgccgtcta ttactgtgct    720 agggggtct accatgatta cgacggggac tactggggcc aagggaccac gctcaccgtc    780
tcctccggtg aggcgggtc tggggcgga ggttcaggcg ggggtggttc cgagcccaaa     840
tctcctgaca aaactcacac atgcccaccg tgcccagcac ctccagtcgc gggaccgtca    900
gtcttcctct tccccccaaa acccaaggac accctcatga tcgcccggac ccctgaggtc    960
acatgcgtgg tggtgaacgt gagccacgaa gaccctgagg tcaagttcaa ctggtacgtg   1020
gacggcgtgg aggtgcataa tgccaagaca aagccgcggg aggagcagta cgccagcacg   1080
taccgtgtgg tcagcgtcct caccgtcctg caccaggact ggctgaatgg caaggagtac   1140
aagtgcaagg tctccaacaa agccctccca gcccccatcg agaaaaccat ctccaaagcc   1200
aaagggcagc cccgagaacc acaggtgtac accctgcccc catcccggga tgagctgacc   1260
aagaaccagg tcagcctgac ctgcctggtc aaaggcttct atcccagcga catcgccgtg   1320
gagtgggaga gcaatgggca gccggagaac aactacaaga ccacgcctcc cgtgctggac   1380
tccgacggct ccttcttcct ctacagcaag ctcaccgtgg acaagagcag gtggcagcag   1440
gggaacgtct tctcatgctc cgtgatgcat gaggctctgc acaaccacta cacacagaag   1500
agcctctccc tgtctccggg taaattttgg gtgctggtgg tggttggtgg agtcctggct   1560
tgctatagct tgctagtaac agtggccttt attattttct gggtgaaacg gggcagaaag   1620 aaaactcctgt atatattcaa acaaccatt atgagaccag tacaaactac tcaagaggaa   1680
gatggctgta gctgccgatt ccagaagaa gaagaaggag gatgtgaact gagagtgaag   1740
ttcagcagga gcgcagacgc ccccgcgtac cagcagggcc agaaccagct ctataacgag   1800
ctcaatctag gacgaagaga ggagtacgat gttttggaca agagacgtgg ccgggaccct   1860
gagatggggg gaaagccgag aaggaagaac cctcaggaag gcctgtacaa tgaactgcag   1920
aaagataaga tggcggaggc ctacagtgag attgggatga aggcgagcg ccggaggggc   1980 aaggggcacg atggccttta ccagggtctc agtacagcca ccaaggacac ctacgacgcc   2040
cttcacatgc aggccctgcc ccctcgc                                       2067

<210> SEQ ID NO 35
<211> LENGTH: 30
<212> TYPE: DNA
<213> ORGANISM: Homo sapiens

<400> SEQUENCE: 35
ggaggaaaaa ctgtttcata cagaaggcgt                                      30

<210> SEQ ID NO 36
<211> LENGTH: 114
<212> TYPE: DNA
<213> ORGANISM: Homo sapiens

<400> SEQUENCE: 36
acattttgac cccccataa tattttttcca gaattaacag tataaattgc atctcttgtt     60
caagagttcc ctatcactct ctttaatcac tactcacagt aacctcaact cctg          114
```

<210> SEQ ID NO 37
<211> LENGTH: 1233
<212> TYPE: DNA
<213> ORGANISM: Artificial Sequence
<220> FEATURE:
<223> OTHER INFORMATION: Constructed nucleic acid sequence of transposon gene expression cassette

<400> SEQUENCE: 37

```
ggaggaaaaa ctgtttcata cagaaggcgt caattaggag gaaaaactgt ttcatacaga      60
aggcgtcaat taggaggaaa aactgtttca tacagaaggc gtcaattgtc ccatcgaatt     120
aggaggaaaa actgtttcat acagaaggcg tcaattagga ggaaaaactg tttcatacag     180
aaggcgtcaa ttaggaggaa aaactgtttc atacagaagg cgtcaattgt cccgggacat     240
tttgacaccc ccataatatt tttccagaat taacagtata aattgcatct cttgttcaag     300
agttccctat cactctcttt aatcactact cacagtaacc tcaactcctg aactccatgg     360
atggtgagca aggcgagga gctgttcacc ggggtggtgc ccatcctggt cgagctggac     420
ggcgacgtaa acggccacaa gttcagcgtg tccggcgagg gcgagggcga tgccacctac     480
ggcaagctga ccctgaagtt catctgcacc accggcaagc tgcccgtgcc ctggcccacc     540
ctcgtgacca ccctgaccta cggcgtgcag tgcttcagcc gctaccccga ccacatgaag     600
cagcacgact tcttcaagtc cgccatgccc gaaggctacg tccaggagcg caccatcttc     660
ttcaaggacg acggcaacta caagacccgc gccgaggtga agttcgaggg cgacaccctg     720
gtgaaccgca tcgagctgaa gggcatcgac ttcaaggagg acggcaacat cctggggcac     780
aagctggagt acaactacaa cagccacaac gtctatatca tggccgacaa gcagaagaac     840
ggcatcaagg tgaacttcaa gatccgccac aacatcgagg acggcagcgt gcagctcgcc     900
gaccactacc agcagaacac ccccatcgga tccggagcca cgaacttctc tctgttaaag     960
caagcaggag acgttgaaga aaaccccggt cctatttaaa tcctcgactg tgccttctag    1020
ttgccagcca tctgttgttt gcccctcccc cgtgccttcc ttgaccctgg aaggtgccac    1080
tcccactgtc ctttcctaat aaaatgagga aattgcatcg cattgtctga gtaggtgtca    1140
ttctattctg gggggtgggg tgggcagga cagcaagggg gaggattggg aagacaatag    1200
caggcatgct ggggatgcgg tgggctctat ggc                                 1233
```

<210> SEQ ID NO 38
<211> LENGTH: 218
<212> TYPE: PRT
<213> ORGANISM: Artificial Sequence
<220> FEATURE:
<223> OTHER INFORMATION: Mutated SANT-7 amino acid sequence

<400> SEQUENCE: 38

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Asp Ile Leu Asp Phe Ile
    50                  55                  60

Ser Ala Leu Arg Lys Glu Thr Cys Asn Lys Ser Asn Met Cys Glu Ser
65                  70                  75                  80

Ser Lys Glu Ala Asp Ala Phe Trp Asn Leu Asn Leu Pro Lys Met Ala
                85                  90                  95
```

Glu Lys Asp Gly Cys Phe Tyr Lys Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Arg Thr Lys Asp Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Ile Arg Ser Leu Arg Ala
        195                 200                 205

Leu Arg Ala Met His His His His His His
    210                 215

<210> SEQ ID NO 39
<211> LENGTH: 655
<212> TYPE: DNA
<213> ORGANISM: Artificial Sequence
<220> FEATURE:
<223> OTHER INFORMATION: Mutated SANT-7 nucleic acid sequence

<400> SEQUENCE: 39
atgaactcct tctccacaag cgccttcggt ccagttgcct ctccctggg gctgctcctg      60 gtgttgcctg ctgccttccc tgccccagta ccccccaggag aagattccaa agatgtagcc    120
gccccacaca gacagccact cacgagctca gaacgaattg acaaacaaat tcgggacatc    180 ctcgactttta tctcagcctt aagaaaggag acatgtaaca gagtaacat gtgtgagagc     240 tccaaagagg cagacgcatt ctggaacctg aaccttccaa agatggctga aaaagatgga    300
tgcttctaca aggattcaa tgaggagact tgcctggtga aatcatcac tggtcttctc      360 gagtttgagg tatacctaga gtacctccag aacagatttg agagtagtga ggaacaagcc    420
agagctgtgc agatgcgcac aaaagacctg atccagttcc tgcagaaaaa ggcaaagaat    480
ctagatgcaa taccacccc tgacccaacc acaaatgcca gcctgctgac gaagctgcag    540
gcacagaacc agtggctgca ggacatgaca actcatctca ttctgagatc ttttaaggag    600
ttcctgatcc gtagcctgag ggctcttcgg gctatgcatc atcaccatca ccact        655

<210> SEQ ID NO 40
<211> LENGTH: 540
<212> TYPE: PRT
<213> ORGANISM: Artificial Sequence
<220> FEATURE:
<223> OTHER INFORMATION: Flexi-IL-12 amino acid construct

<400> SEQUENCE: 40

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

```
Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
            290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Ser Gly Gly Gly
                325                 330                 335

Gly Ser Gly Gly Gly Gly Ser Arg Asn Leu Pro Val Ala Thr Pro Asp
            340                 345                 350

Pro Gly Met Phe Pro Cys Leu His His Ser Gln Asn Leu Leu Arg Ala
            355                 360                 365

Val Ser Asn Met Leu Gln Lys Ala Arg Gln Thr Leu Glu Phe Tyr Pro
            370                 375                 380

Cys Thr Ser Glu Glu Ile Asp His Glu Asp Ile Thr Lys Asp Lys Thr
385                 390                 395                 400

Ser Thr Val Glu Ala Cys Leu Pro Leu Glu Leu Thr Lys Asn Glu Ser
                405                 410                 415

Cys Leu Asn Ser Arg Glu Thr Ser Phe Ile Thr Asn Gly Ser Cys Leu
            420                 425                 430

Ala Ser Arg Lys Thr Ser Phe Met Met Ala Leu Cys Leu Ser Ser Ile
            435                 440                 445

Tyr Glu Asp Leu Lys Met Tyr Gln Val Glu Phe Lys Thr Met Asn Ala
            450                 455                 460

Lys Leu Leu Met Asp Pro Lys Arg Gln Ile Phe Leu Asp Gln Asn Met
465                 470                 475                 480

Leu Ala Val Ile Asp Glu Leu Met Gln Ala Leu Asn Phe Asn Ser Glu
```

|  | 485 |  |  |  | 490 |  |  |  | 495 |  |  |
|---|---|---|---|---|---|---|---|---|---|---|---|

Thr Val Pro Gln Lys Ser Ser Leu Glu Glu Pro Asp Phe Tyr Lys Thr
        500              505              510

Lys Ile Lys Leu Cys Ile Leu Leu His Ala Phe Arg Ile Arg Ala Val
        515              520              525

Thr Ile Asp Arg Val Met Ser Tyr Leu Asn Ala Ser
        530              535              540

<210> SEQ ID NO 41
<211> LENGTH: 1620
<212> TYPE: DNA
<213> ORGANISM: Artificial Sequence
<220> FEATURE:
<223> OTHER INFORMATION: Flexi-IL-12 nucleic acid construct

<400> SEQUENCE: 41

| | |
|---|---|
| atgtgtcacc agcagttggt catctcttgg ttttccctgg tttttctggc atctcccctc | 60 |
| gtggccatat ggaactgaa gaaagatgtt tatgtcgtag aattggattg gtatccggat | 120 |
| gccccctgga gaaatggtgg cctcacctgt gacacccctg aagaagatgg tatcacctgg | 180 |
| accttggacc agagcagtga ggtcttaggc tctggcaaaa ccctgaccat ccaagtcaaa | 240 |
| gagtttggag atgctggcca gtacacctgt cacaaggag gcgaggttct aagccattcg | 300 |
| ctcctgctgc ttcacaaaaa ggaagatgga atttggtcca ctgatatttt aaaggaccag | 360 |
| aaagaaccca aaaataagac ctttctaaga tgcgaggcca gaattattc tggacgtttc | 420 |
| acctgctggt ggctgacgac aatcagtact gatttgacat tcagtgtcaa agcagcaga | 480 |
| ggctcttctg acccccaagg ggtgacgtgc ggagctgcta cactctctgc agagagagtc | 540 |
| agagggaca caaggagta tgagtactca gtggagtgcc aggaggacag tgcctgccca | 600 |
| gctgctgagg agagtctgcc cattgaggtc atggtggatg ccgttcacaa gctcaagtat | 660 |
| gaaaactaca ccagcagctt cttcatcagg gacatcatca aacctgaccc acccaagaac | 720 |
| ttgcagctga agccattaaa gaattctcgg caggtggagg tcagctggga gtaccctgac | 780 |
| acctggagta ctccacattc ctacttctcc ctgacattct gcgttcaggt ccagggcaag | 840 |
| agcaagagag aaaagaaaga tagagtcttc acggacaaga cctcagccac ggtcatctgc | 900 |
| cgcaaaaatg ccagcattag cgtgcgggcc caggaccgct actatagctc atcttggagc | 960 |
| gaatgggcat ctgtgccctg cagtggtggc ggtggaagcg gcggtggcgg aagcggcggt | 1020 |
| ggcggcagca gaaacctccc cgtggccact ccagacccag gaatgttccc atgccttcac | 1080 |
| cactcccaaa acctgctgag ggccgtcagc aacatgctcc agaaggccag acaaactcta | 1140 |
| gaatttttacc cttgcacttc tgaagagatt gatcatgaag atatcacaaa agataaaacc | 1200 |
| agcacagtgg aggcctgttt accattggaa ttaaccaaga tgagagttg cctaaattcc | 1260 |
| agagagacct ctttcataac taatgggagt tgcctggcct ccagaaagac ctcttttatg | 1320 |
| atggcctgt gccttagtag tatttatgaa gacttgaaga tgtaccaggt ggagttcaag | 1380 |
| accatgaatg caaagcttct gatggatcct aagaggcaga tctttctaga tcaaaacatg | 1440 |
| ctggcagtta ttgatgagct gatgcaggcc tgaatttca acgtgagac tgtgccacaa | 1500 |
| aaatcctccc ttgaagaacc ggattttat aaaactaaaa tcaagctctg catacttctt | 1560 |
| catgctttca gaattcgggc agtgactatt gatagagtga tgagctatct gaatgcttcc | 1620 |

<210> SEQ ID NO 42
<211> LENGTH: 170
<212> TYPE: PRT

```
<213> ORGANISM: Artificial Sequence
<220> FEATURE:
<223> OTHER INFORMATION: GAL 3C amino acid construct

<400> SEQUENCE: 42

Met Glu Phe Gly Leu Ser Trp Leu Phe Leu Val Ala Ile Leu Lys Gly
1               5                   10                  15

Val Gln Cys Ser Arg His His His His His Gly Ala Pro Ala Gly
            20                  25                  30

Pro Leu Ile Val Pro Tyr Asn Leu Pro Leu Pro Gly Gly Val Val Pro
        35                  40                  45

Arg Met Leu Ile Thr Ile Leu Gly Thr Val Lys Pro Asn Ala Asn Arg
    50                  55                  60

Ile Ala Leu Asp Phe Gln Arg Gly Asn Asp Val Ala Phe His Phe Asn
65                  70                  75                  80

Pro Arg Phe Asn Glu Asn Asn Arg Arg Val Ile Val Cys Asn Thr Lys
                85                  90                  95

Leu Asp Asn Asn Trp Gly Arg Glu Glu Arg Gln Ser Val Phe Pro Phe
            100                 105                 110

Glu Ser Gly Lys Pro Phe Lys Ile Gln Val Leu Val Glu Pro Asp His
        115                 120                 125

Phe Lys Val Ala Val Asn Asp Ala His Leu Leu Gln Tyr Asn His Arg
    130                 135                 140

Val Lys Lys Leu Asn Glu Ile Ser Lys Leu Gly Ile Ser Gly Asp Ile
145                 150                 155                 160

Asp Leu Thr Ser Ala Ser Tyr Thr Met Ile
                165                 170

<210> SEQ ID NO 43
<211> LENGTH: 510
<212> TYPE: DNA
<213> ORGANISM: Artificial Sequence
<220> FEATURE:
<223> OTHER INFORMATION: GAL 3C nucleic acid construct

<400> SEQUENCE: 43
atggagtttg gctgagctg gcttttctt gtggctattt taaaaggtgt ccagtgctct       60
agacatcatc accatcacca cggcgcccct gctgggccac tgattgtgcc ttataacctg     120
cctttgcctg ggggagtggt gcctcgcatg ctgataacaa ttctgggcac ggtgaagccc     180
aatgcaaaca gaattgcttt agatttccaa agagggaatg atgttgcctt ccactttaac     240
ccacgcttca atgagaacaa caggagagtc attgtttgca atacaaagct ggataataac     300
tggggaaggg aagaaagaca gtcggttttc ccatttgaaa gtgggaaacc attcaaaata     360
caagtactgg ttgaacctga ccacttcaag gttgcagtga atgatgctca cttgttgcag     420
tacaatcatc gggttaaaaa actcaatgaa atcagcaaac tgggaatttc tggtgacata     480
gacctcacca gtgcttcata taccatgata                                      510
```